US012306132B2

(12) United States Patent
Claussen et al.

(10) Patent No.: US 12,306,132 B2
(45) Date of Patent: May 20, 2025

(54) AEROSOL JET PRINTED FLEXIBLE GRAPHENE CIRCUITS FOR ELECTROCHEMICAL SENSING AND BIOSENSING

(71) Applicants: Iowa State University Research Foundation, Inc., Ames, IA (US); Northwestern University, Evanston, IL (US)

(72) Inventors: Jonathan Claussen, Ames, IA (US); Kshama Parate, Ames, IA (US); Mark C. Hersam, Willmette, IL (US); Sonal V. Rangnekar, Chicago, IL (US)

(73) Assignees: Iowa State University Research Foundation, Inc., Ames, IA (US); NORTHWESTERN UNIVERSITY, Evanston, IL (US)

( * ) Notice: Subject to any disclaimer, the term of this patent is extended or adjusted under 35 U.S.C. 154(b) by 1088 days.

(21) Appl. No.: 17/248,211

(22) Filed: Jan. 14, 2021

(65) Prior Publication Data

US 2021/0215636 A1    Jul. 15, 2021

Related U.S. Application Data

(60) Provisional application No. 62/961,034, filed on Jan. 14, 2020.

(51) Int. Cl.
*G01N 27/414*    (2006.01)
*B29C 64/10*    (2017.01)
(Continued)

(52) U.S. Cl.
CPC ......... *G01N 27/4148* (2013.01); *B29C 64/10* (2017.08); *B29C 64/112* (2017.08);
(Continued)

(58) Field of Classification Search
CPC ........... B29K 2001/08; G01N 27/4148; G01N 33/5438; G01N 27/4145; B29C 61/112;
(Continued)

(56) References Cited

U.S. PATENT DOCUMENTS 5,348,593 A    9/1994 Bowe et al.
8,901,620 B2    12/2014 Lee et al.
(Continued)

FOREIGN PATENT DOCUMENTS

WO    2019005708 A2    1/2019
WO    WO-2019152648 A1 *    8/2019    ............. C09D 11/52

OTHER PUBLICATIONS

International Searching Authority in connection with PCT/US2021/013442, filed Jan. 14, 2021, "International Search Report and Written Opinion of the International Searching Authority, or the Declaration", 21 pages, mailed Aug. 12, 2021.
(Continued)

*Primary Examiner* — Alonzo Chambliss
(74) *Attorney, Agent, or Firm* — McKee, Voorhees & Sease, PLC

(57) ABSTRACT

Methods and systems of fabrication of high resolution, high-throughput electrochemical sensing circuits on a substrate. High resolution electrochemical sensing circuits are printed by an effective additive technique to the substrate. Optionally, post-print annealing converts electrochemically inactive printed graphene into one that is electrochemically active. The printing can be by aerosol jet printing, but is not necessarily limited thereto. An example is inkjet printing and then the post-print annealing. Ink formulation would be adjusted for effectiveness with inkjet printing. Optionally biorecognition agents can be covalently bonded to the printed graphene for the purpose of electrochemical biosensing. High throughput fabrication of high-resolution gra-
(Continued)

Figures 1A, 1B:
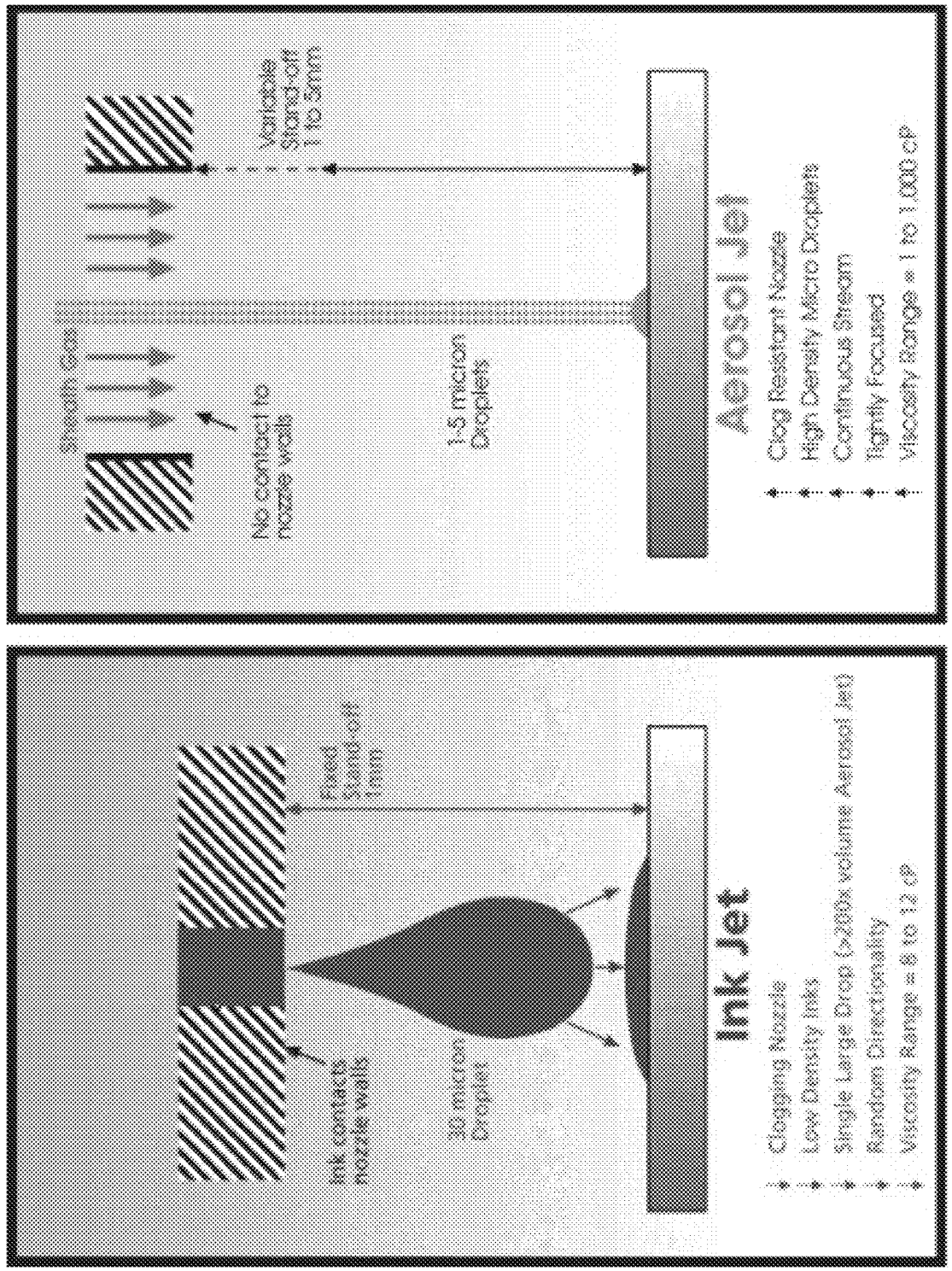

phene circuits (feature sizes in the tens of microns <50 μm) for electrochemical biosensing is possible by chemical functionalization of the graphene surface with a biological agent.

**41 Claims, 49 Drawing Sheets
(40 of 49 Drawing Sheet(s) Filed in Color)**

(51) Int. Cl.
| | |
|---|---|
| *B29C 64/112* | (2017.01) |
| *B33Y 10/00* | (2015.01) |
| *B33Y 40/20* | (2020.01) |
| *B33Y 80/00* | (2015.01) |
| *B41M 3/00* | (2006.01) |
| *B41M 5/00* | (2006.01) |
| *B41M 7/00* | (2006.01) |
| *G01N 33/543* | (2006.01) |
| *B29K 1/00* | (2006.01) |
| *B29L 31/00* | (2006.01) |
| *B33Y 40/00* | (2020.01) |
| *B33Y 70/00* | (2020.01) |

(52) U.S. Cl.
CPC ............... *B33Y 10/00* (2014.12); *B33Y 40/20* (2020.01); *B33Y 80/00* (2014.12); *B41M 3/006* (2013.01); *B41M 5/0023* (2013.01); *B41M 7/009* (2013.01); *G01N 27/4145* (2013.01); *G01N 33/5438* (2013.01); *B29K 2001/08* (2013.01); *B29L 2031/752* (2013.01); *B33Y 40/00* (2014.12); *B33Y 70/00* (2014.12)

(58) Field of Classification Search
CPC ..... B29C 64/10; B41M 3/006; B41M 5/0023; B41M 7/009; B33Y 10/00; B33Y 80/00; B33Y 40/20; B33Y 70/00; B33Y 40/00
See application file for complete search history.

(56) References Cited

U.S. PATENT DOCUMENTS

| | | | |
|---|---|---|---|
| 9,834,693 B2 | 12/2017 | Hersam et al. | |
| 9,902,866 B2 | 2/2018 | Hersam et al. | |
| 10,280,317 B2* | 5/2019 | Hersam | C09D 11/14 |
| 10,876,210 B1* | 12/2020 | Claussen | H05K 1/092 |
| 2009/0297574 A1 | 12/2009 | Ahn et al. | |
| 2012/0231576 A1 | 9/2012 | King et al. | |
| 2013/0248380 A1 | 9/2013 | Cui | |
| 2013/0323863 A1 | 12/2013 | Niyogi et al. | |
| 2014/0035995 A1 | 2/2014 | Chou et al. | |
| 2014/0103298 A1* | 4/2014 | Lee | G01N 33/48 257/29 |
| 2014/0322608 A1 | 10/2014 | Claussen et al. | |
| 2015/0140646 A1 | 5/2015 | Khattak et al. | |
| 2015/0307730 A1 | 10/2015 | Hersam et al. | |
| 2016/0134327 A1* | 5/2016 | Joshi | H04B 1/707 29/832 |
| 2016/0177387 A1 | 6/2016 | Roy et al. | |
| 2016/0262262 A1 | 9/2016 | Findley | |
| 2016/0326386 A1 | 11/2016 | Toyserkani et al. | |
| 2016/0341722 A1 | 11/2016 | Lim et al. | |
| 2017/0048975 A1 | 2/2017 | Johnson et al. | |
| 2017/0102348 A1 | 4/2017 | Neethirajan et al. | |
| 2017/0196513 A1 | 7/2017 | Longinotti-Buitoni et al. | |
| 2018/0010001 A1 | 1/2018 | Hersam et al. | |
| 2018/0328924 A1* | 11/2018 | Van Grinsven | G01N 25/20 |
| 2021/0017408 A1* | 1/2021 | Fujimoto | C01B 32/19 |
| 2023/0287226 A1* | 9/2023 | Panat | G01N 33/56983 |

OTHER PUBLICATIONS

Ahmed et al., "Toward the development of smart and low cost point-of-care biosensors based on screen printed electrodes", Critical Reviews in Biotechnology, vol. 36(3), pp. 495-505, 2016.

Costa et al., "A low cost, safe, disposable, rapid and self-sustainable paper-based platform for diagnostic testing: lab-on-paper", Nanotechnology, vol. 25, 13 pages, Feb. 12, 2014.

Fairchild et al., "A Label-free, Rapid Multimarker Protein Impedance-based Immunosensor", ICME International Conference on Complex Medical Engineering, Tempe, AZ, 5 pages, 2009.

Hondred et al., "Enhanced electrochemical biosensor and supercapacitor with 3D porous architectured graphene via salt impregnated inkjet maskless lithography", Nanoscale Horizons, vol. 4, pp. 735-746, Jan. 31, 2019.

Hong et al., "Aerosol Jet Printed p. and n-type Electrolyte-Gated Transistors with a Variety of Electrode Materials: Exploring Practical Routes to Printed Electronics", Applied Materials & Interfaces, vol. 6, pp. 18704-18711, Oct. 17, 2014.

Jabari et al., "Micro-scale aerosol-jet printing of graphene interconnects", Carbon, vol. 91, pp. 321-329, Apr. 30, 2015.

Liu et al., "All-carbon-based field effect transistors fabricated by aerosol jet printing on flexible substrates", Journal of Micromechanics and Microengineering. vol. 23, 7 pages, May 13, 2013.

Maattanen et al. "A low-cost paper-based inkjet-printed platform for electrochemical analyses", Sensors and Actuators B, vol. 177, pp. 153-162, 2013.

Min et al., "A simple and direct electrochemical detection of interferon-y using its RNA and DNA aptamers", Biosensors and Bioelectronics, vol. 23, pp. 1819-1824, Feb. 25, 2008.

Neethirajan et al., "Recent advancement in biosensors technology for animal and livestock health management", Biosensors and Bioelectronics, vol. 98, pp. 398-407, Jul. 5, 2017.

Parate et al., "Aerosol-jet-printed graphene immunosensor for label-free cytokine monitoring in serum", ACS Appl. Mater. Interfaces, vol. 12, No. 7, Appendix A1, 37 pages, Feb. 10, 2020.

Parate et al., "Aerosol-jet-printed graphene immunosensor for label-free cytokine monitoring in serum: Supplemental Information", ACS Appl. Mater. Interfaces, vol. 12, No. 7, Appendix A2, 14 pages, Feb. 10, 2020.

Rodriguez-Mozaz et al., "Analysis of bisphenol A in natural waters by means of an optical immunosensor", Water Research, vol. 39, pp. 5071-5079, 2005.

Secor et al., "Wiring up Liquid Metal: Stable and Robust Electrical Contacts Enabled by Printable Graphene Inks", Advanced Electronic Materials, vol. 4, 6 pages, 2018.

Seifert et al., "Additive Manufacturing Technologies Compared: Morphology of Deposits of Silver Ink Using Inkjet and Aerosol Jet Printing", I&EC Research, vol. 54, pp. 76-779, Jan. 8, 2015.

Shafiee et al., "Paper and Flexible Substrates as Materials for Biosensing Platforms to Detect Multiple Biotargets", Scientific Reports, vol. 5, 9 pages, Mar. 6, 2015.

Wang et al., " Pre-binding dynamic range and sensitivity enhancement for immuno-sensors using nanofluidic preconcentrator", Lab on a Chip, vol. 8, pp. 392-394, Mar. 2008.

Zhang et al., "Multiplexed cytokine detection on plasmonic gold substrates with enhanced near-infrared fluorescence", Nano Research, vol. 6(2), pp. 113-120, 2013.

Written Opinion of the International Preliminary Examining Authority in connection with PCT/US2021/013442, filed Jan. 14, 2021, 10 pages, mailed Feb. 17, 2022.

OPTOMEC 2014 Webinar, "Aerosol Jet Printing of Flexible Electronic Circuitry—Highlights from over 5 years of Research Conducted at the U of M", 59 Pages, Apr. 2, 2014.

* cited by examiner

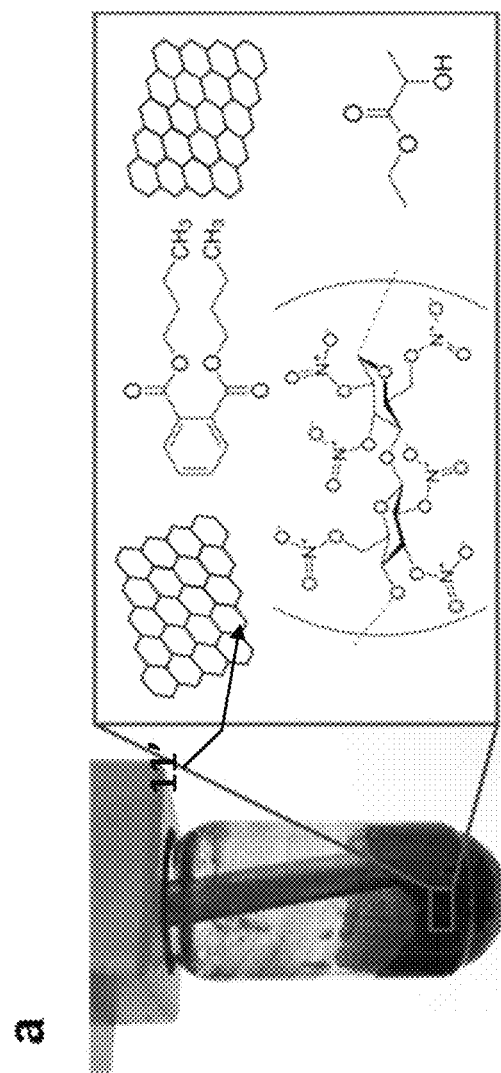
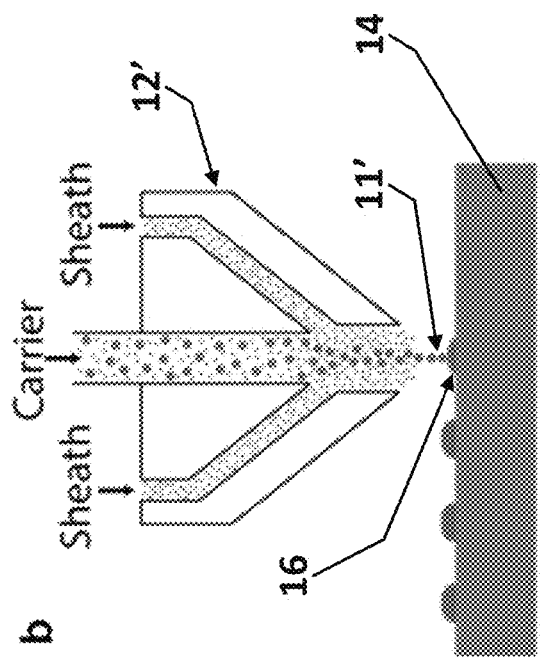
FIG. 3A
FIG. 3B

45° tilt

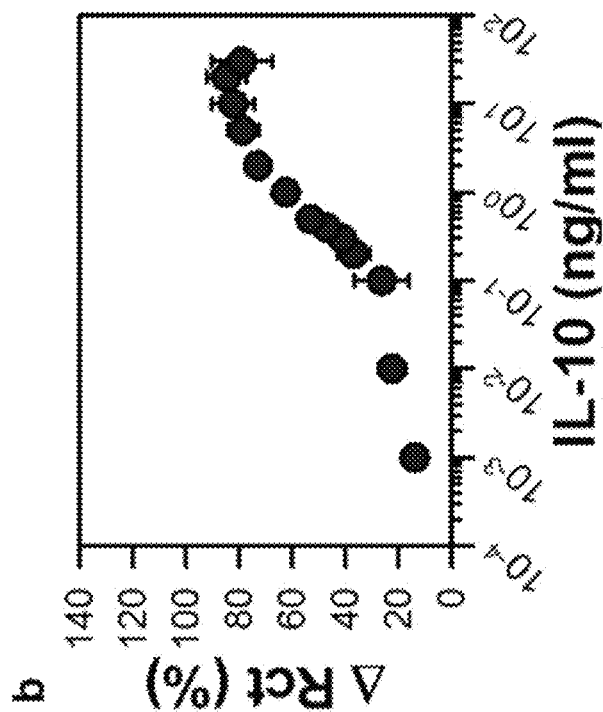
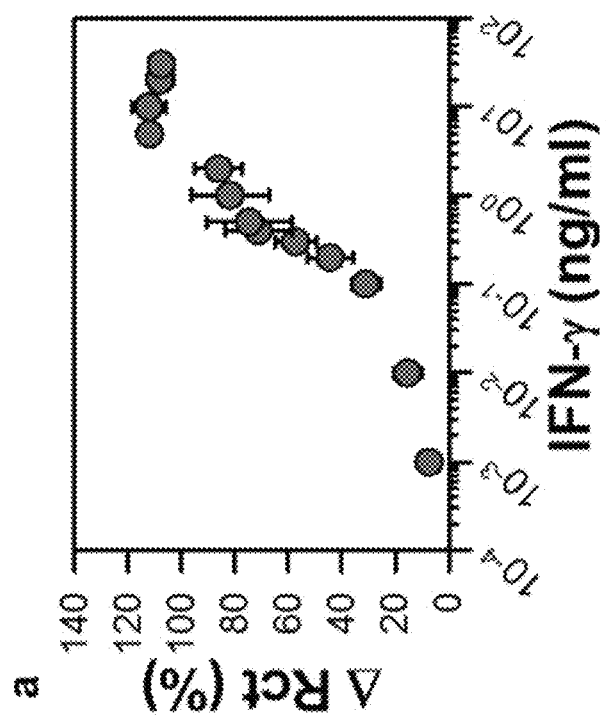
FIG. 7A
FIG. 7B

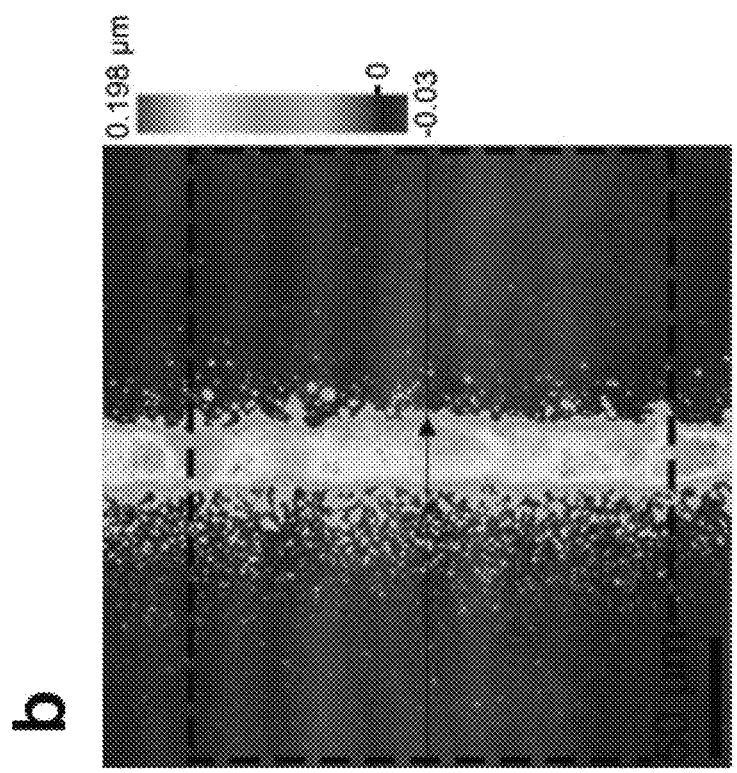
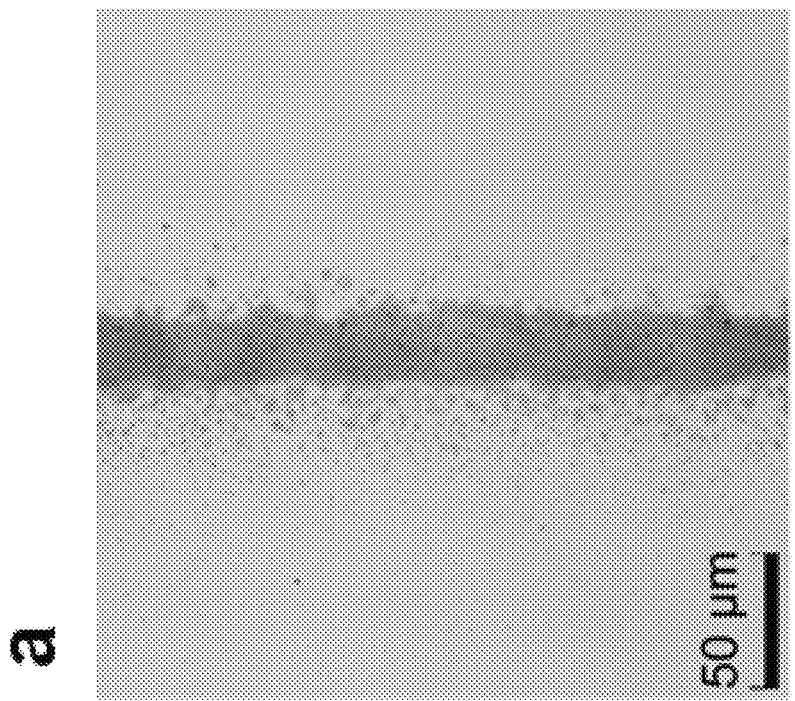
FIG. 9B
FIG. 9A

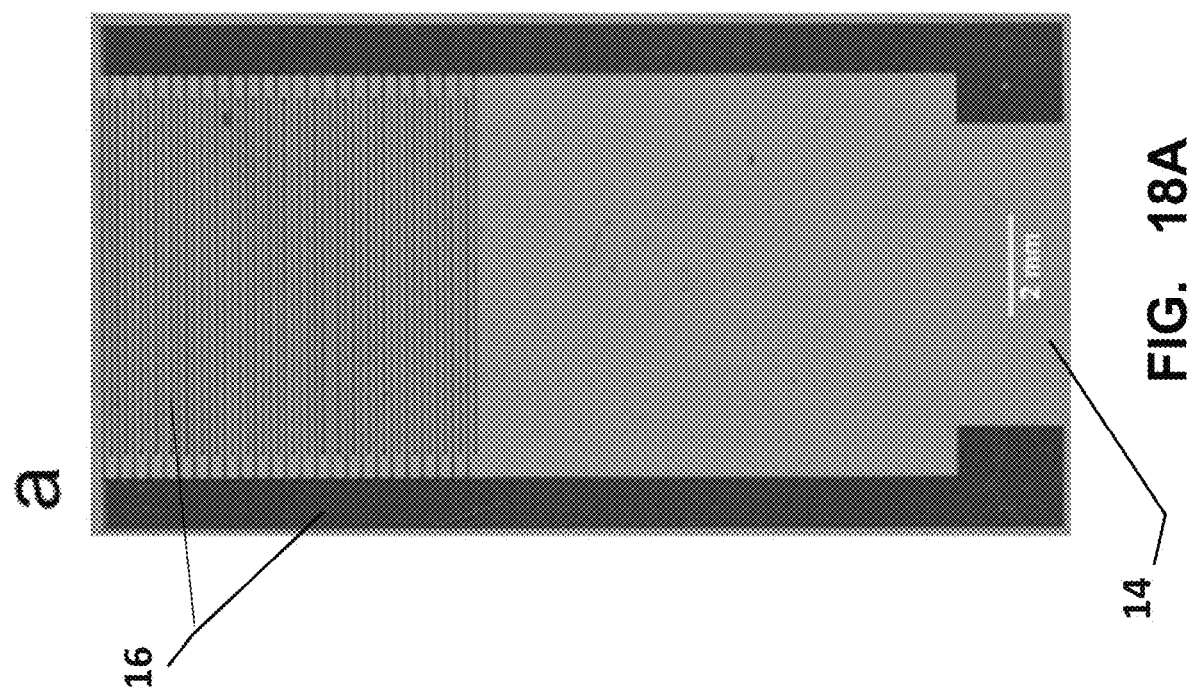

AEROSOL JET PRINTED FLEXIBLE GRAPHENE CIRCUITS FOR ELECTROCHEMICAL SENSING AND BIOSENSING

CROSS-REFERENCE TO RELATED APPLICATIONS

This application claims the benefit of Provisional Application U.S. Ser. No. 62/961,034 filed on Jan. 14, 2020, all of which is herein incorporated by reference in its entirety.

GRANT REFERENCE

Work for this invention was funded in part by grants from National Science Foundation Grant Nos. CBET-1706994, EECS-1841649 and DMR-1505849, and National Institute of Standards and Technology Grant Number 70NANB19H005. The United States government may have certain rights in this invention.

I. BACKGROUND OF THE INVENTION

A. Field of the Invention

This invention relates to electrochemical sensing and biosensing with high resolution, high-throughput graphene circuits and, in particular, to methods, systems, and compositions that facilitate the same.

B. Related Art

Printing low-cost and flexible electrical circuits from graphene-based inks is becoming increasingly attractive due to their high electrical conductivity, biocompatibility, and scalable fabrication. Conventional graphene printing techniques, such as screen and inkjet printing, are limited by requirements on ink rheological properties and large (~100 micron) as-printed line width, which impedes the performance of printed biosensors.

Methods to obtain graphene have included micromechanical (scotch-tape) exfoliation and chemical vapor deposition (CVD), which have limited scalability due to low amounts of graphene production and high energy/time costs. In comparison, solution-processing (e.g. liquid phase exfoliation or shear mixing) of graphene enables large volumes of graphene to be simultaneously produced and dispersed in solvent. These graphene dispersions are amenable to formulating inks for printing, and methods like screen printing and inkjet printing have been used to create biosensing graphene devices. However, these deposition methods are limited by ink requirements on viscosity and particle size and a technological inability to print line widths below 100 microns without pre- or post-patterning steps or ink formulation strategies that are material dependent. The thick line width is particularly problematic for obtaining high performance electrochemical biosensors that utilize interdigitated electrodes. Aerosol jet printing, which can produce line widths down to 10 microns and is compatible with inks with a wider range of viscosities and particle sizes, offers a more universal approach to fabricate highly sensitive and selective graphene-based biosensors. These biosensors can be produced in a cost-effective and scalable fashion that allows them to be used disposably for point-of-care diagnostics.

Point-of-care diagnostics requires biosensing devices that can be produced cheaply and scalably for use in rural medical clinics or in agricultural settings. Graphene is a semi metallic carbon nanomaterial that can be produced and dispersed in solvents at low cost, formulated into inks, and printed into electronic devices. Graphene-based electrochemical biosensing technology thus far has been limited by large printed feature sizes, which impede biosensing ability, or complicated/costly processing and fabrication to achieve small-feature sizes. The aerosol jet printing technology used in this invention is compatible with high-throughput, roll-to-roll manufacturing and can produce printed features that are an order of magnitude smaller than other printing methods, such as inkjet printing. Overall, aerosol jet printing of graphene-based inks enables the scalable, cost-effective production of high-performance biosensors.

Previously commercialized graphene biosensing products include AGILE-100 (sold by NanoMed) and Six™ Graphene Sensors (sold by Graphene Frontiers). While both platforms provide label-free sensing using graphene, the commercialized sensors are based on field-effect transistors (FETs), which are fabricated through relatively expensive photolithography techniques. Our printed graphene biosensors are significantly cheaper, as the graphene starting product can be obtained in large amounts through solution-processing and aerosol jet printing compatible with high-throughput, roll-to-roll manufacturing. The surface functionalization achieved by annealing the printed graphene in $CO_2$ allows compatibility with a wide range of sensing molecules, enabling sensing for diverse chemical or biological species.

Aerosol jet printing has been used to print high resolution devices, often with polymer materials such PEDOT:PSS (Hong, Kim et al. 2014) or silver ink (Seifelt, Sowade et al. 2015) or graphene oxide which is subsequently reduced to graphene (Liu, Shen et al. 2013). Such devices have been used for electronic applications such as transistors printed to replace traditional semiconductor materials. However, a direct aerosol printed graphene device that is applied for biosensing application has not been demonstrated.

This work demonstrates the fabrication of a high resolution (finger width of 40 µm), thin film (film thickness of 25 nm) aerosol printed graphene IDE on a flexible polyimide sheet and its application to create in-field electrochemical biosensors. One non-limiting application is detection of Johne's disease in cattle. Similar works to ours show deposition of much thicker material although the resolution might be higher (Jabari and Toyserkani 2015). Also, similar works demonstrate detection in buffer rather than in actual biological serum (Fairchild, McAfelty et al. 2009, Zhang, Price et al. 2013). On the other hand, some works show the use of preconcentration and pre-labelling the cytokines with redox probe or fluorescent label to improve the signal (Rodriguez-Mozaz, De Alda et al. 2005, Wang and Han 2008). These steps add complexity to the assay and render the technique difficult for point-of-care applications.

Both the use of metallic inks or need of pre-treatment of the sample (pre-labeling or pre-concentration) increase the cost of the biosensor, as compared to the aerosol printed immunosensor which can be used as a one-time, disposable biosensor (Maattanen, Vanamo et al. 2013, Costa, Veigas et al. 2014, Ahmed, Hossain et al. 2016). In this invention, we demonstrate that this device is capable of sensing both the cytokines of interest in the relevant concentration range where the cattle is deemed sick (0.1-10 ng/ml) (Min, Cho et al. 2008) without the need to pre-label or pre-concentrate the sample nor the need to immobilize metallic nanoparticles onto the graphene surface to increase its reactive surface area. We also demonstrate that the device is flexible and robust and hence could be used in real biological curvilinear environment such as a wearable biosensor (Ahn, Narayan et al. 2014, Shafiee, Asghar et al. 2015, Neethirajan, Tuteja et al. 2017), each of which is incorporated by reference herein.

Publications in the field of graphene biosensors as background include:

1) Novel electrochemical DNA biosensor using graphene biochip for species identification (2016), US20160177387A1 (incorporated by reference herein).
2) Electrochemical biosensor for metabolic disease of cattle (2017), US20170102348A1 (incorporated by reference herein).
3) Flexible graphene biosensor (2013), US20130248380A1 (incorporated by reference herein).
4) Biosensor comprising reduced graphene oxide layer (2014) U.S. Pat. No. 8,901,620B2 (incorporated by reference herein).
5) References in the bibliography at the end of the section entitled "Embodiment 1", infra.

As is evidenced by the wide range of attempts to create such graphene-based circuits, and the competing factors and parameters involved in effectively producing such circuits, this art is inherently unpredictable. For example, working at such small scales is unpredictable at least in terms of precision, accuracy, ability to economically fabricate and scale, ability to produce efficacy of functionality, etc. Another it the ability to produce effective graphene-based material that can then be adhered to a wide range of substrates and achieve desired functionality. All these factors can be competing, and sometimes antagonistic to one another. For example, there are techniques of high precision circuit deposition on substrates at this scale, but it may involve complex, high-cost machines. The same can be true for mass-production. Another example involves pre- or post-processing steps and materials. Some suggested graphene formulations require specific techniques and combination of materials.

The market for point-of-care diagnostics is projected to be $30.9 billion by 2024, and the availability of over-the-counter testing kits is anticipated to be a major driver for market growth. A limiting factor for providing cost-effective diagnostic kits has been the cost of producing and fabricating the biosensing materials and devices. Therefore, the inventors have identified room for improvement in this technical field.

II. SUMMARY OF THE INVENTION

A. Objects, Features, and Advantages

A primary object, feature, and/or advantage of the present invention is to provide methods, systems, and compositions which improve over or solve problems and deficiencies in the state of the art.

Further objects, features, and/or advantage of the present invention are methods, systems, and compositions which:

a. Configure aerosol jet printing of a graphene-based ink to fabricate a sensor or biosensor, which enables significant advances in large-scale commercial adoption of high-performance printed graphene immunosensors. From an economic perspective, our invention provides a pathway for scalable, cost-effective sensors, which can be used to detect a wide variety of chemical and biological species.
b. With aerosol jet printing, can produce line widths down to on the order of 10 microns and is compatible with inks with a wider range of viscosities and particle sizes, offers a more universal approach to fabricate highly sensitive and selective graphene-based biosensors, and can produce functional patterns (e.g. biosensors) in a cost-effective and scalable fashion that allows them to be used disposably for, inter alia, point-of-care diagnostics.
c. Features can include:
  i. Improved electrical signals—stronger electrochemical impedance signal.
  ii. Highly sensitive measurements or sensing.
  iii. Scalable, low-cost manufacturing.
d. Aerosol jet printing and biofunctionalization are also amenable to scalable, low-cost manufacturing.
e. At demonstrated versions of ~40 μm wide and ~30 nm thick, the printed graphene lines are the narrowest and thinnest obtained through graphene printing without additional lithography. This improved spatial resolution allows us to decrease the channel length of the interdigitated electrode, which enables a stronger electrochemical impedance (EIS) signal.
f. Post-print annealing process that enables both electrochemical sensing and electrochemical biosensing. The $CO_2$ annealing converts an electrochemically inactive printed graphene to one that is electrochemically active. The cyclic voltammograms and electrochemical impedance spectroscopy plots in FIGS. 6D and E show how unannealed graphene is electrochemically inactive then how $CO_2$ annealing converts the graphene into an electroactive material that could be used to detect electroactive species in solution (e.g., hydrogen peroxide, dopamine, uric acid, acetaminophen). The $CO_2$ annealing also substantially increases the amount of oxygen species on the surface of the graphene as exhibited in the x ray photoelectron spectroscopy plots in FIGS. 5A and B. These oxygen species are then needed to covalently bind antibody to the graphene surface for subsequent electrochemical biosensing. Hence the $CO_2$ annealing enables both electrochemical sensing (sensing of analytes in solution without a biorecognition agent immobilized on the surface) and biosensing (sensing of analytes in solution with a biorecognition agent) in solution.
g. While graphene-based biosensors and immunosensors have been used for electronic applications, all previous work deposited graphene oxide and then reduced it to yield reduced graphene oxide (some papers call this "functionalized graphene"). In contrast, our method can utilize pristine graphene, which is then uniformly functionalized with carboxyl groups using $CO_2$ annealing. The result is a well-defined chemical functionalization with improved electronic properties, both of which result in higher EIS signal.
h. Our sensors have achieved the best limit of detection and selectivity for an immunosensor that can monitor both bovine IL-10 and IFN-gamma in any fluid sample including actual bovine samples. In particular, this device detects the biomarkers in the sensing range (0.1-10 ng/mL) that is appropriate for the bovine disease paratuberculosis.
i. Many immunosensors need to label the antigen with a redox probe (e.g., metallic nanoparticle) or fluorescent label to improve the electrochemical signal sensitivity or visualize the biorecognition agent binding event. In addition, other biosensors require steps to preconcentrate the target analyte before the biosensor can make a readable measurement. Such labeling and preconcentration steps significantly increase assay complexity and are not amenable to point-of-care in vitro or in vivo experiments. In contrast, our invention overcomes these limitations.

j. Many immunosensors need to label the antigen with a redox probe (e.g., metallic nanoparticle) or fluorescent label to improve the electrochemical signal sensitivity or visualize the biorecognition agent binding event. Other biosensors require steps to preconcentrate the target analyte before the biosensor can make a readable measurement. Such labeling and preconcentration steps significantly increases assay complexity and are not amenable to in vitro or in vivo experiments and are generally difficult to perform at the point-of-care. This invention does not require these.

k. The printing and biofunctionalization are amenable to scalable manufacturing. This is primarily due to the lack of need for preconcentration and labeling steps makes the biosensor low-cost and well-suited for one-time, disposable biosensing.

l. The printing and biofunctionalization are amenable to scalable, low-cost manufacturing. Consequently, our biosensor is well-suited for one-time, disposable use.

m. Using techniques according to the invention, fabricated sensors can retain their electrical conductivity and biosensing capability even after repeated bending cycles. For example, the graphene ink and printing processes herein can allow for graphene circuits that do not crack during repeated bending. Also, functionalization with a biorecognition agent (antibody) is sufficiently robust so that the antibody can still remain attached and active on the graphene surface even after repeated bending. Both retaining electrical conductivity and biosensing capability after repeated bending is nontrivial. Such flexible capability is important as it opens the door to flexible electronics and applications such as wearable biosensors.

n. Can be implemented in a variety of sensing application. Non-limiting examples are electrochemical sensing and biosensing. Further non-limiting examples are high resolution electrical circuits such as interdigitated electrodes. A few non-limiting sensing applications are immunosensing and food safety monitoring, but can be generalized to a diverse range of sensing applications including environmental toxin detection, foodborne pathogen detection, wearable health monitoring, and health diagnostics.

B. Aspects of the Invention

In one aspect of the invention, fabrication of high resolution, high-throughput electrochemical sensing circuits on a substrate comprises aerosol jet printing pristine graphene flakes. The substrate could vary. For example, it could be flexible or not. It could be a variety of different materials for a variety of different applications. The substrate and printed circuits can be fabricated with additive manufacturing techniques. Because it does not require subtractive manufacturing the fabrication can be relatively economical. Specific ink formulations effective for aerosol jet printing are disclosed.

In another aspect of the invention, high resolution electrochemical sensing circuits are printed by an effective technique to the substrate. In one example, post-print $CO_2$ annealing converts electrochemically inactive printed graphene into one that is electrochemically active. The printing can be by aerosol jet printing, but is not necessarily limited thereto. An example is inkjet printing and then the post-print annealing. Ink formulation would be adjusted for effectiveness with inkjet printing. Annealing, such as with the example of $CO_2$ annealing process, converts an electrochemically inactive printed graphene to one that is electrochemically active. Cyclic voltammograms and electrochemical impedance spectroscopy plots from empirical testing have demonstrated how unannealed graphene is electrochemically inactive then how $CO_2$ annealing converts the graphene into an electroactive material that could be used to detect electroactive species in solution (e.g., hydrogen peroxide, dopamine, uric acid, acetaminophen).

Another aspect of the invention comprises a method of covalently binding biorecognition agents to aerosol printed graphene for the purpose of electrochemical biosensing. Post-print annealing, for example $CO_2$ annealing discussed above, can also substantially increases the amount of oxygen species on the surface of the graphene. X-ray photoelectron spectroscopy from empirical testing demonstrate this. These oxygen species are then used to covalently bind antibodies to the graphene surface for subsequent electrochemical biosensing. Therefore, the post-print annealing can enable both electrochemical sensing (sensing of analytes in solution without a biorecognition agent immobilized on the surface) and biosensing (sensing of analytes in solution with a biorecognition agent) in solution.

In one aspect of the invention, a method, means, and compositions are provided for electrochemical biosensing with high resolution, high-throughput graphene circuits. Our invention introduces the fabrication of high-resolution graphene circuits (feature sizes in the tens of microns <50 μm) for electrochemical biosensing. Herein, biosensing refers to chemical functionalization of the graphene surface with a biological agent (e.g., antibody, aptamer/DNA, enzyme, ionophore) for selective measurement of a chemical/biochemical analyte in solution. Electrochemical biosensing refers to transducing the chemical/biochemical analyte binding to the biological agent into an electrochemical measurement/signal (e.g., amperometry, cyclic voltammetry, potentiometry, electrochemical impedance spectroscopy). Our technology uses high-throughput methods to create these circuits without the need to perform low-throughput, expensive chemical vapor deposition (CVD) to synthesize the graphene and its respective circuits. We have shown the ability to create these high-throughput graphene circuits through a variety of methods including inkjet printing combined with inkjet maskless lithography (IML) and aerosol jet printing.

In another aspect of the invention, the foregoing method, means, and compositions can be combined with other steps or processes. For example, we have also shown how you can anneal and texture these graphene circuits even on chemically or thermally sensitive substrates (polymers or paper) through rapid-pulse laser annealing and Salt Impregnated Inkjet Maskless Lithography (SIIML).

It important to note that our technology is believed to be the first to use:
1. graphene or graphene oxide exfoliated from graphite (a bulk synthesis process that is low-cost) and
2. convert them into inks that can be inkjet or aerosol printed with resolutions on the tens of microns without the need to use stencils or photolithography.

Moreover, our technology is believed to be the first to:
3. convert high-resolution printed graphene circuits into electrochemical sensor and biosensors. Others have decorated metal electrode surfaces with graphene flakes (often with drop coating from a pipette tip—which is a manually intensive process) or have printed low-resolution (>50 μm line resolution) graphene sensors for electrochemical biosensing. Again, such techniques are not high-throughput and often require a metal electrode to support the graphene. Moreover, these techniques do not perform post-print annealing that increases the electrocatalytic nature of the graphene to enable electrochemical sensing nor do they increase the superficial oxygen groups needed to covalently bind biorecognition agents (e.g., antibodies) to robust electrochemical biosensing. One example of such conversion is by post-print annealing (e.g. $CO_2$ annealing).

Our graphene sensors are:
a. completely metal free (i.e., low-cost),
b. are only comprised of the carbon graphene,
c. are printed with high-resolution.
d. can be 3D micro/nanostructured with rapid-pulse laser annealing or salt porogens,
e. electrochemically active because of post-print $CO_2$ annealing,
f. amenable to covalent biofunctionalization with a biorecognition agent (e.g., antibody) because of annealing,
g. flexible, can retain their electrical conductivity and biosensing capability even after repeated bending cycles.

III. BRIEF DESCRIPTION OF THE DRAWINGS

In the following descriptions of exemplary embodiments, certain figures are included to illustrate certain concepts.

The patent or application file contains at least one drawing executed in color. Copies of this patent or patent application publication with color drawing(s) will be provided by the Office upon request and payment of the necessary fee.

Following are descriptions of the drawings that referenced herein. These drawings are incorporated by reference and a part of this disclosure.

FIG. 1A. Diagrammatic depiction of inkjet printing and its variables relative to high resolution printing.

FIG. 1B. Diagrammatic depiction of aerosol jet printing (AJP) and its variables related to high resolution printing.

Figure 2A:
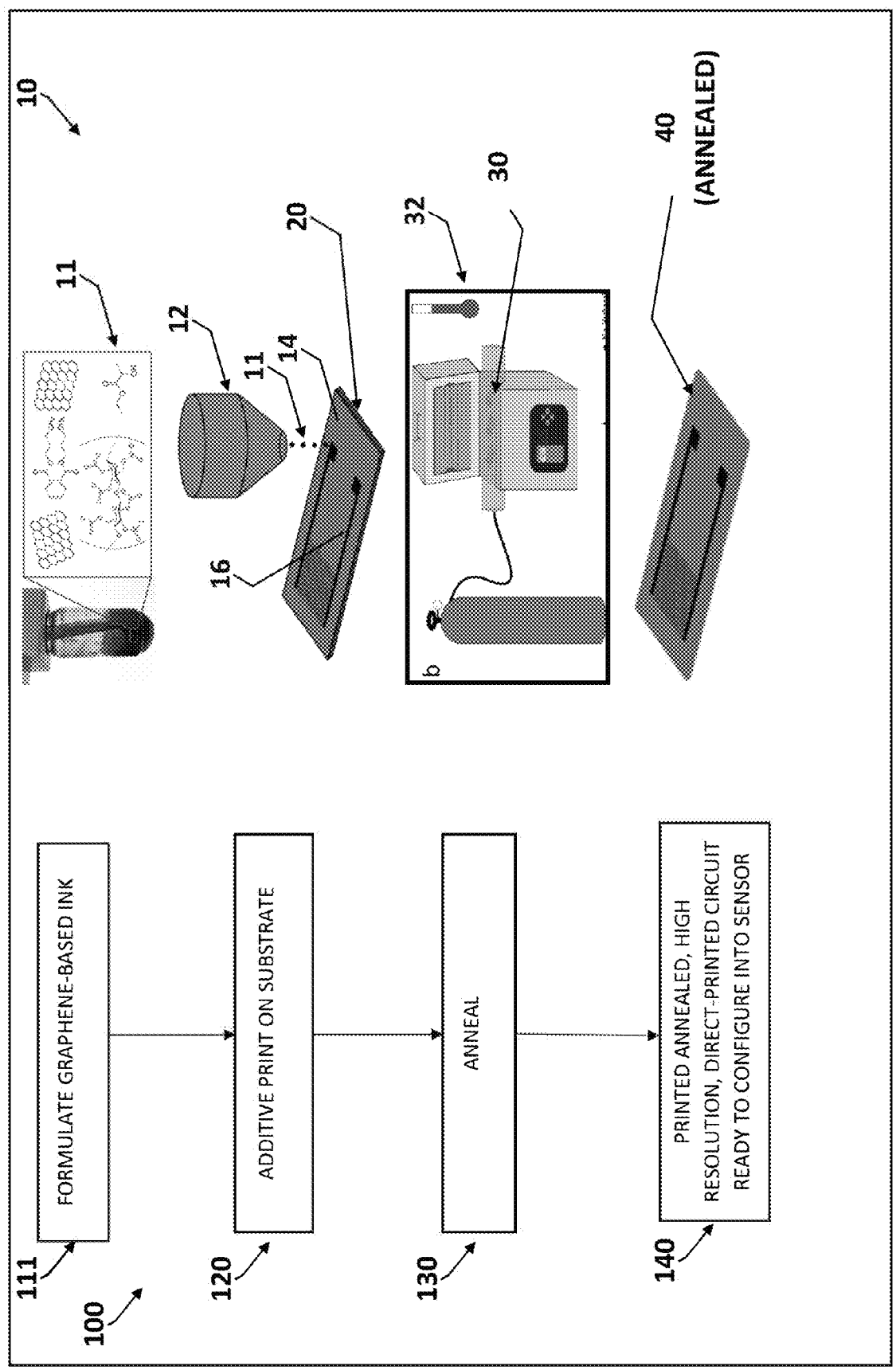

FIG. 2A. Diagrammatical depiction of a method and system according to a generalized embodiment of the invention.

Figure 2B:
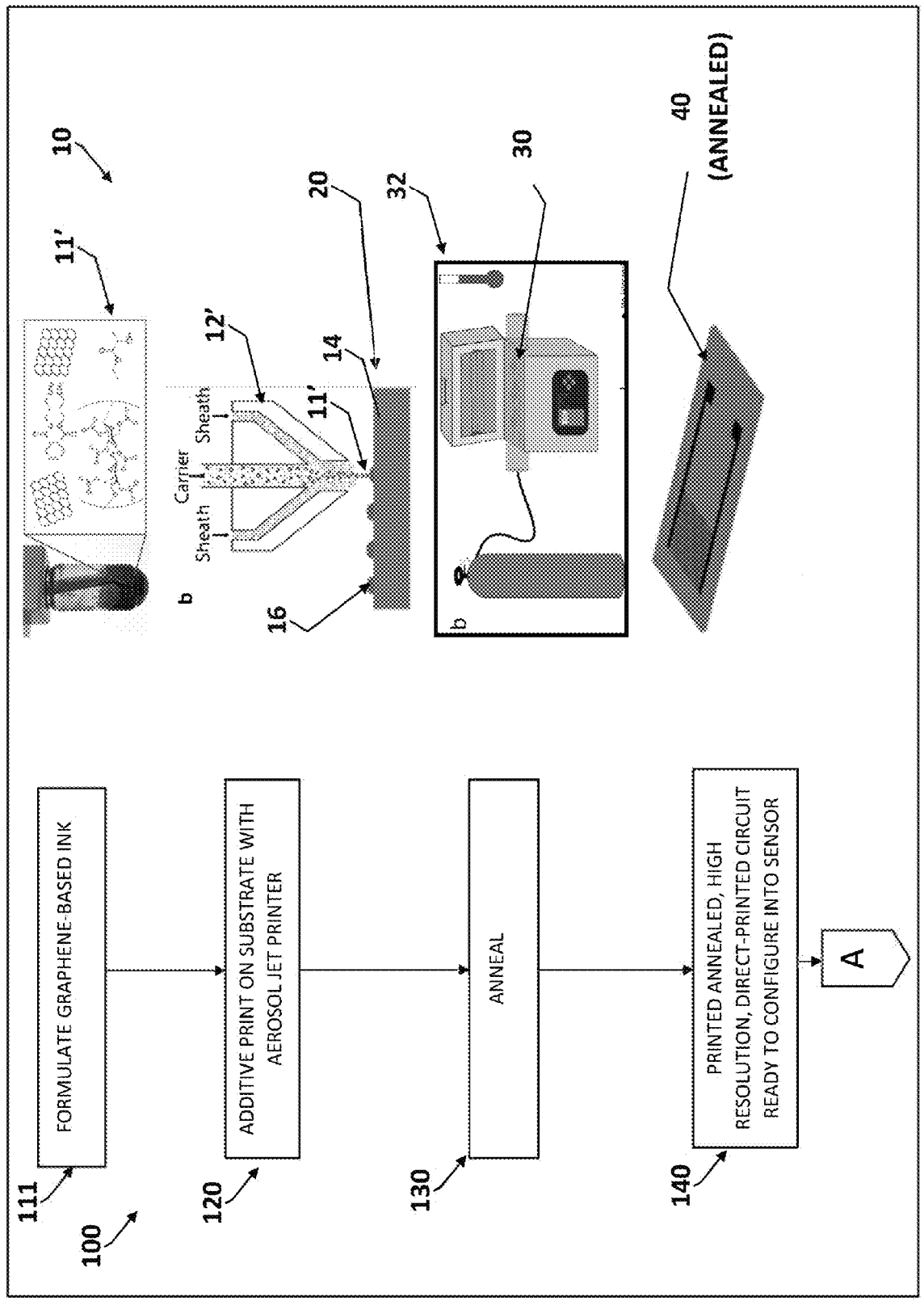

FIG. 2B. Diagrammatical depiction of a method and system according to a generalized embodiment of the invention.

Figure 2C:
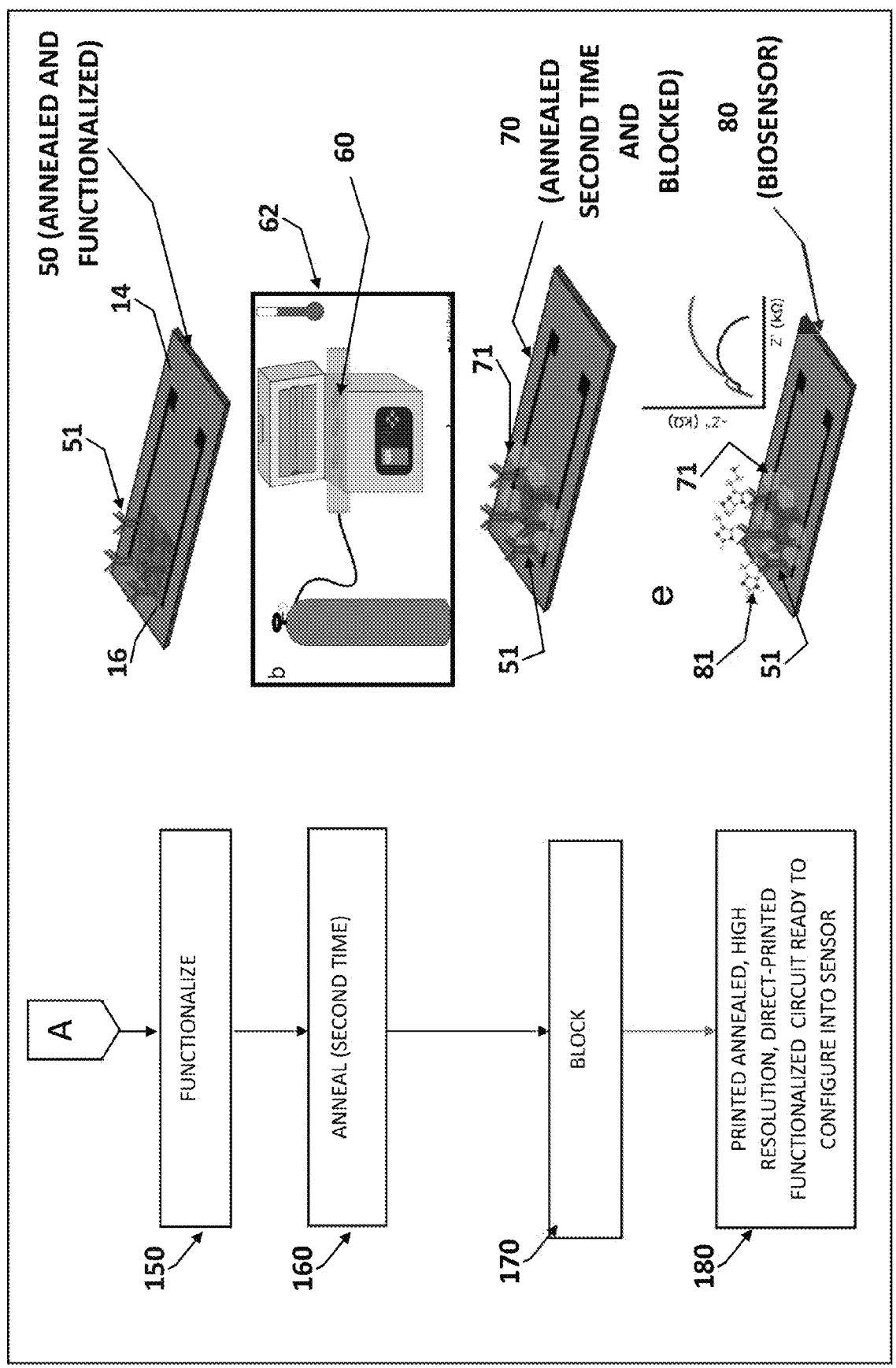

FIG. 2C. Diagrammatical depiction of additional method and system operations according to a generalized embodiment of the invention.

Figure 3C:
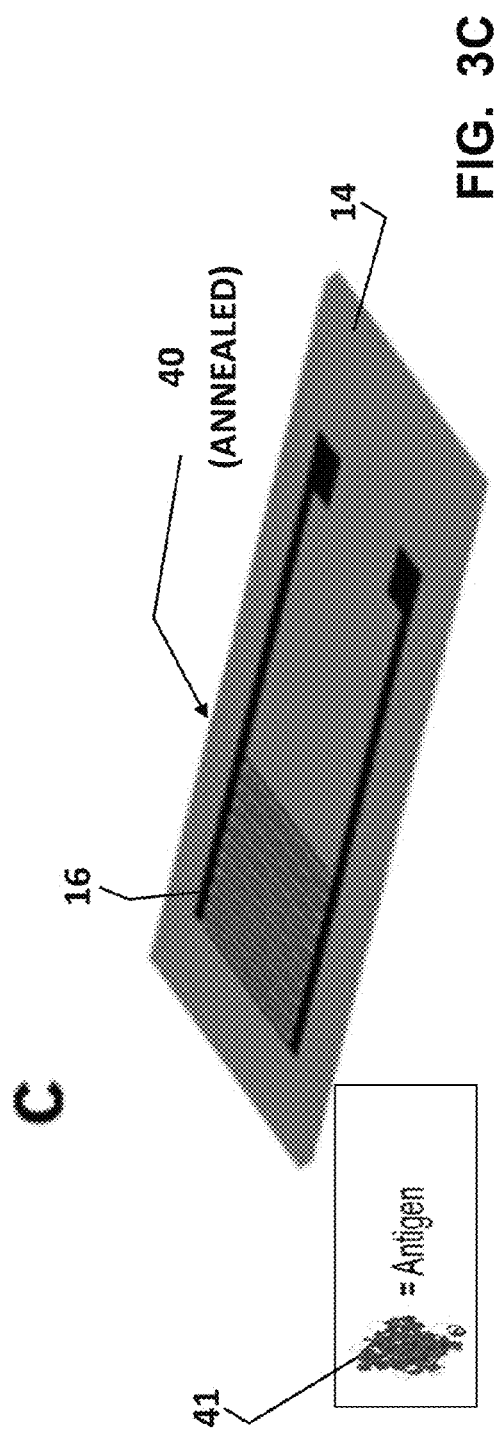
Figure 3D:
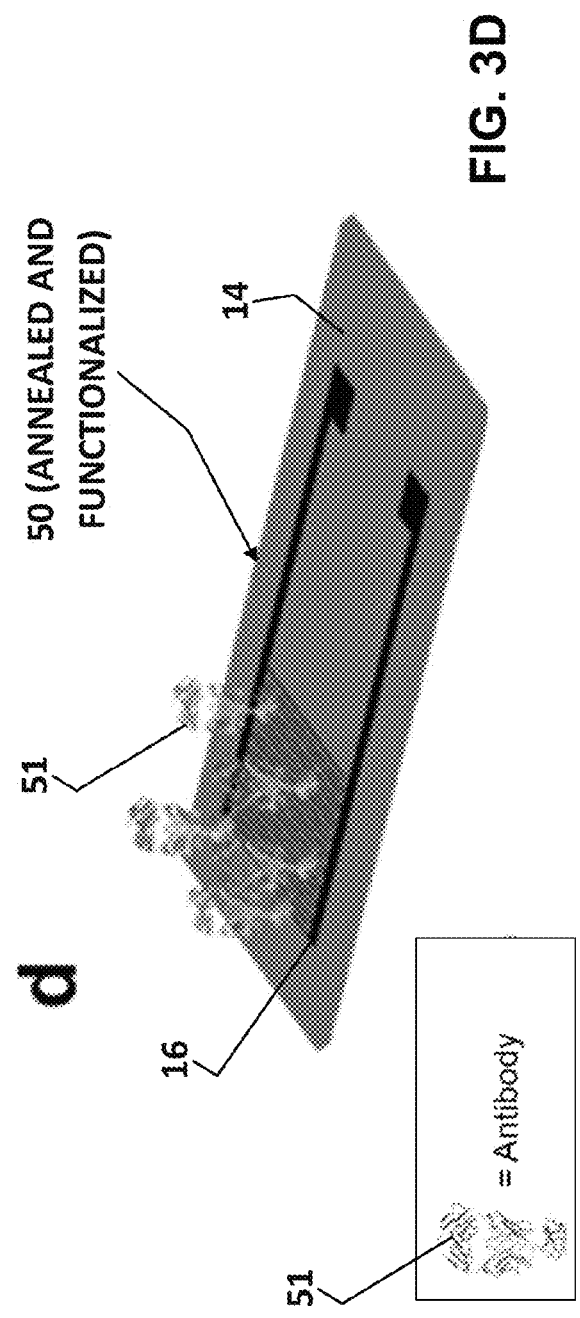
Figure 3E:
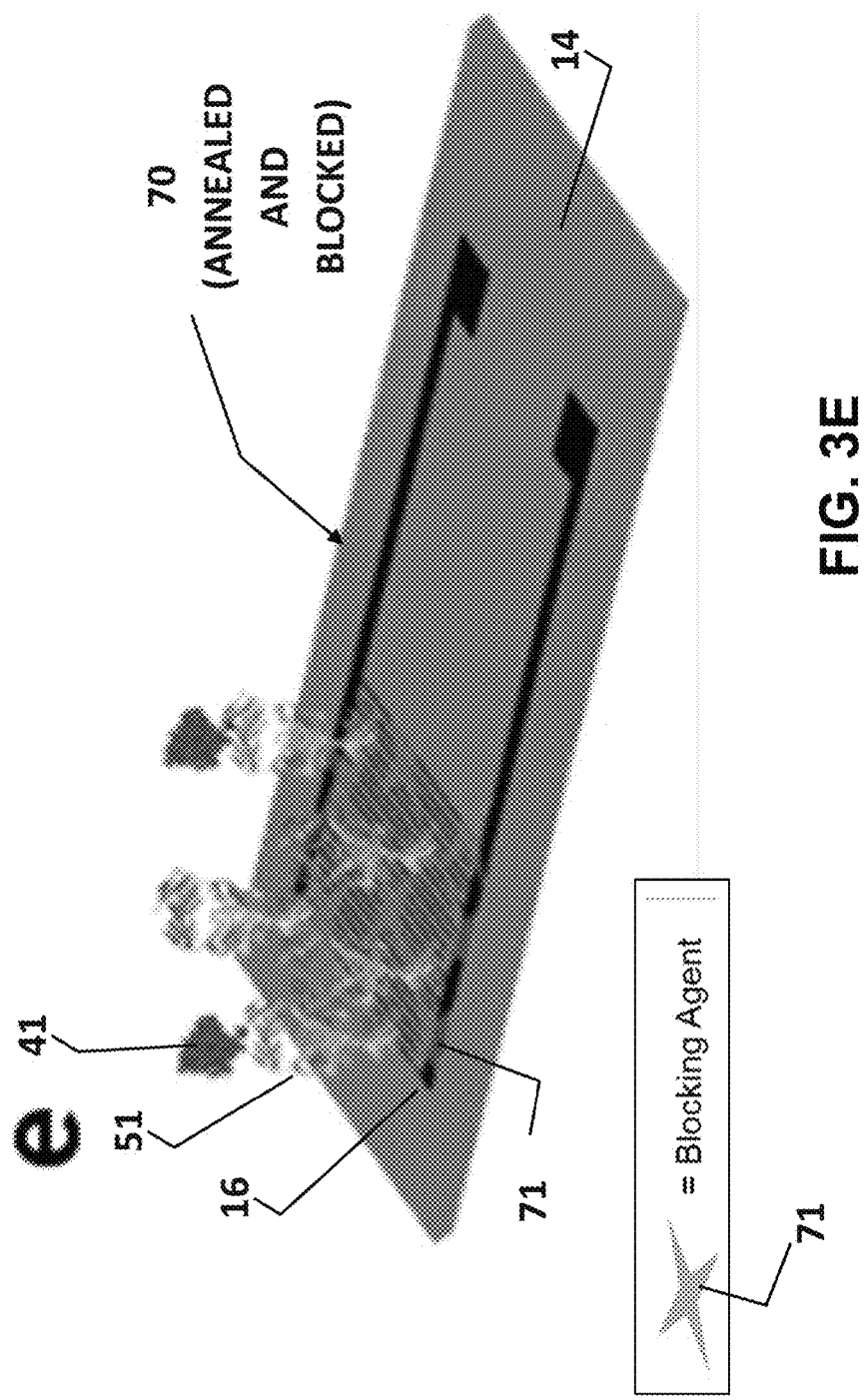

FIGS. 3A-E. Schematic representation of fabrication and biofunctionalization of the AJP graphene IDE. FIG. 3A. Schematic demonstrating the graphene ink formulation for aerosol printing. FIG. 3B: Aerosol jet printing mechanism of the graphene ink illustrating a sheath gas enveloping the carrier with aerosolized graphene ink particles for focusing the ink to a desired diameter. FIG. 3C: AJP graphene IDE on a polyimide (Kapton®) sheet. FIG. 3D: Antibodies selective to IL-10 or IFN-γ are immobilized on the carboxyl group functionalized graphene surface using N-(3-Dimethylaminopropyl)-N'-ethylcarbodiimide/N-hydroxy succinimide (EDC/NHS) chemistry. FIG. 3E: The remaining exposed surface of the graphene sensor is covered with the blocking agent (mixture of bovine serum albumin (BSA), fish gelatin, and tween) and incubated with antigen.

Figure 4A:
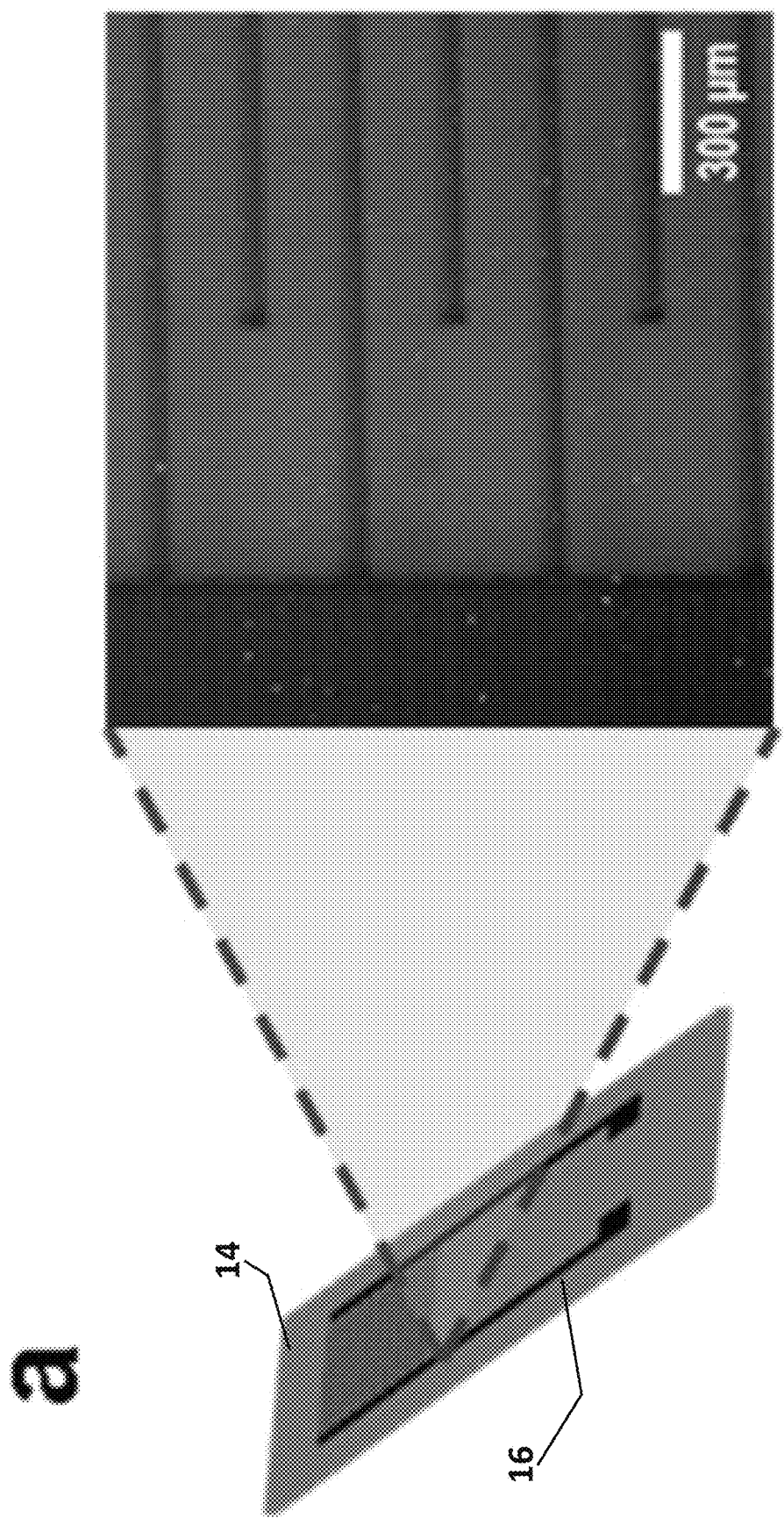
Figure 4C:
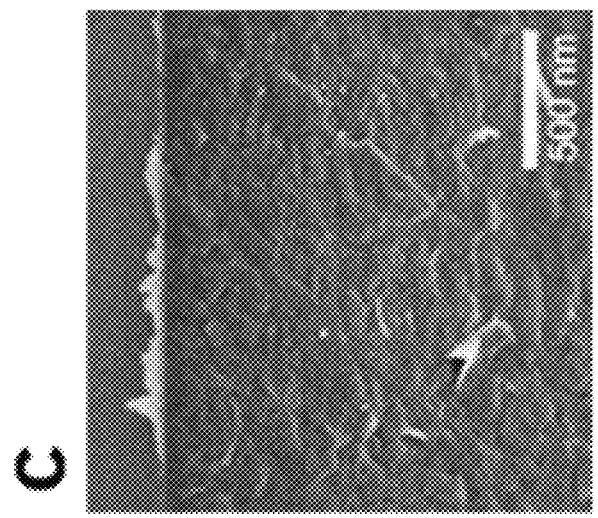
Figure 4B:
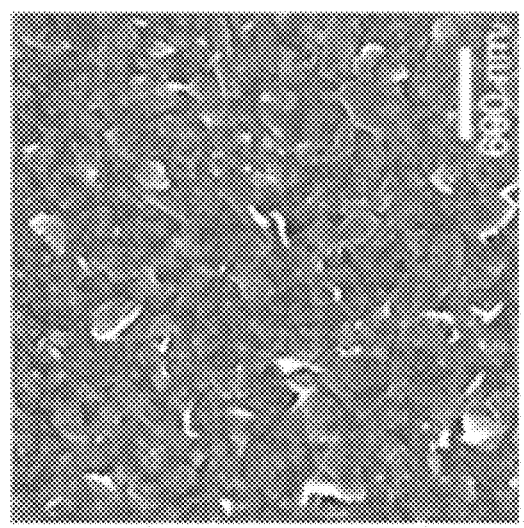
Figure 4D:
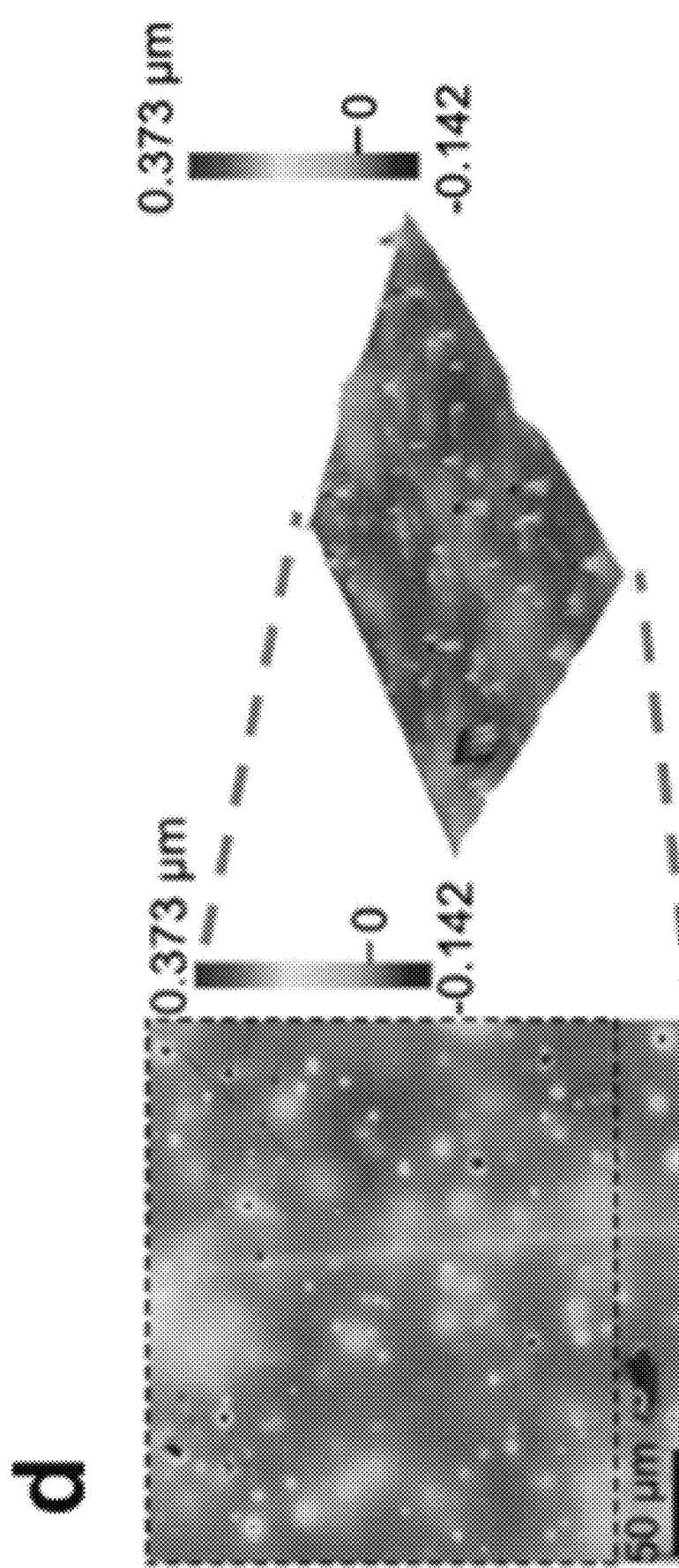
Figure 4F:
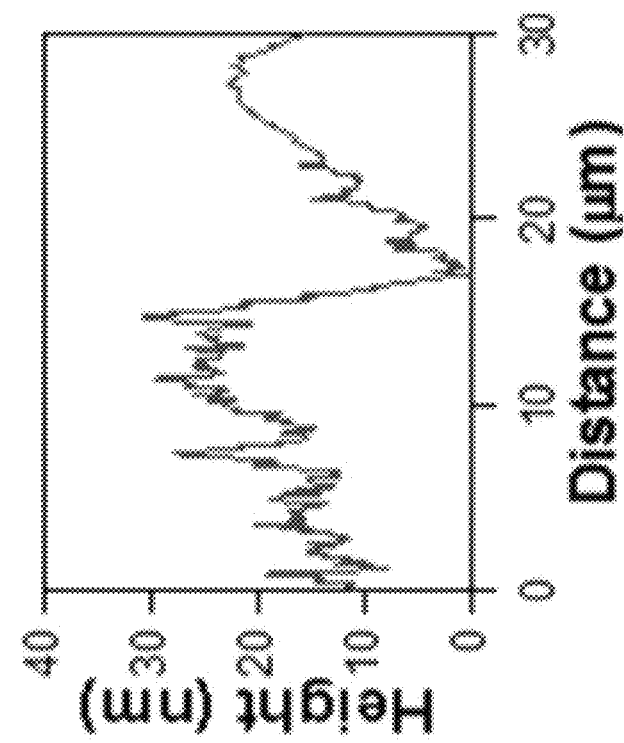
Figure 4E:
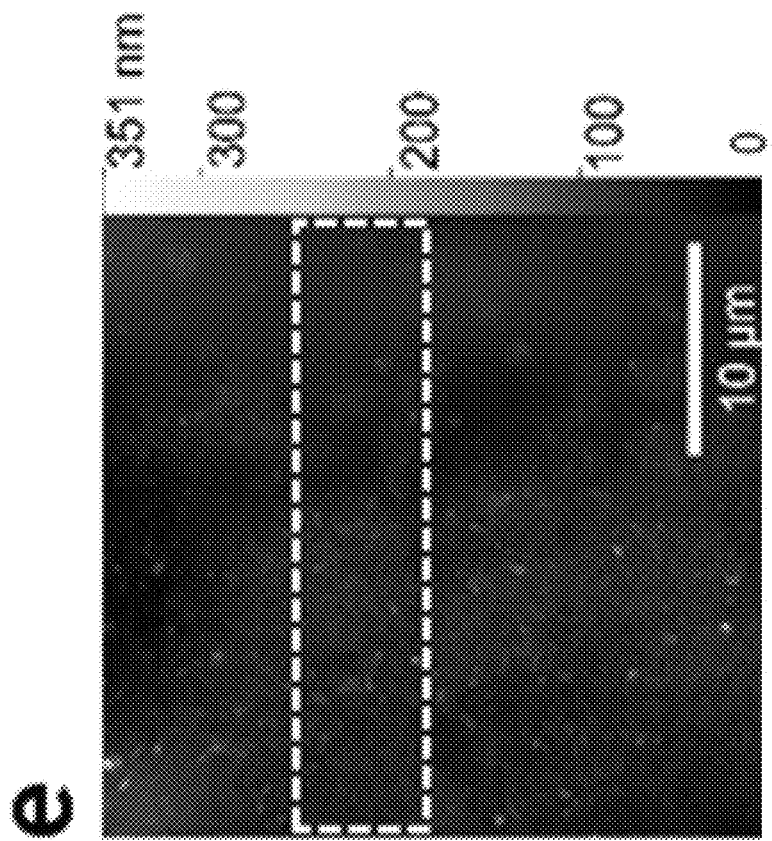

FIGS. 4A-F. Optical characterization of an AJP printed graphene IDE. FIG. 4A: Optical micrograph showing line resolution. SEM micrographs displaying: FIG. 4B: surface morphology of the graphene sheets on the polyimide substrate that is magnified 75,000 times. FIG. 4C: 45°-tilted (magnified 30,000 times) top down SEM micrograph of ultrathin (sub-100 nm thick) film printed on $SiO_2$. FIG. 4D: The surface irregularity and roughness of bare, as-received Kapton® film is observed in 2D and 3D height image. FIG. 4E: AFM image of the graphene IDE finger and FIG. 4F profile of the AFM micrograph showing the average film thickness of the printed graphene as 25 nm averaged across the boxed region in FIG. 4E.

Figure 5B:
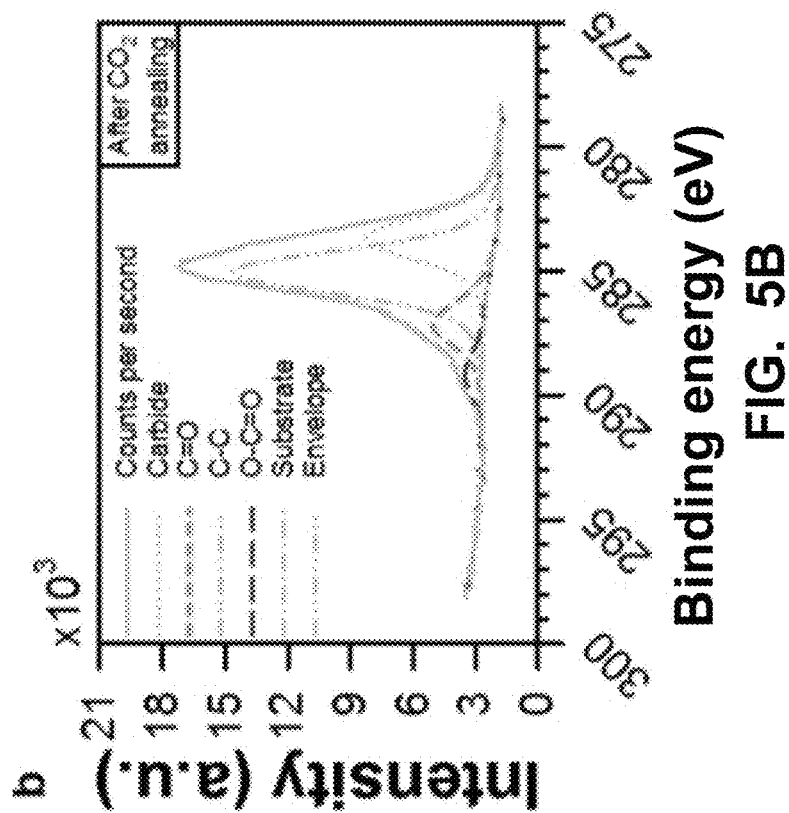
Figure 5A:
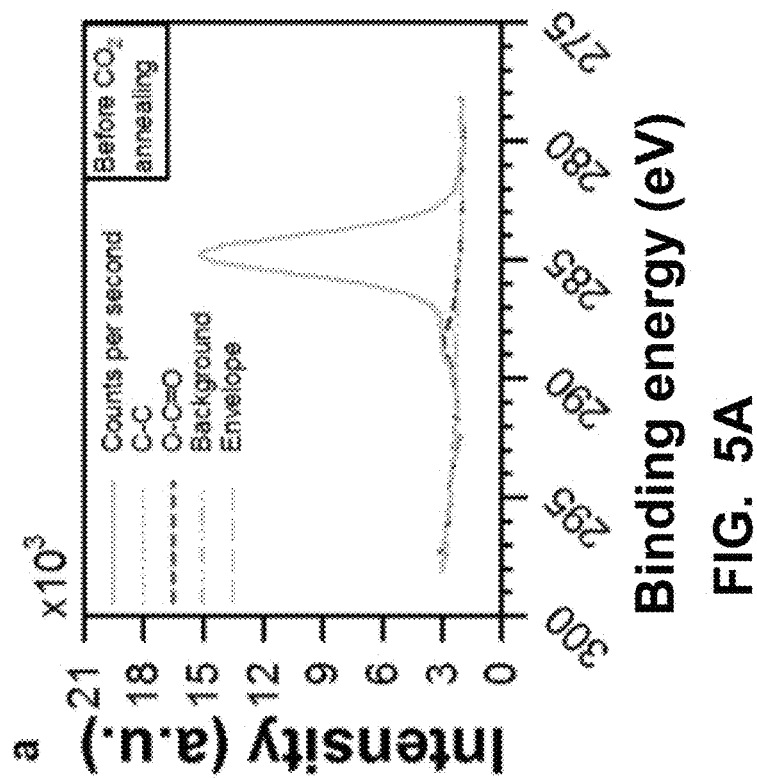
Figure 5C:
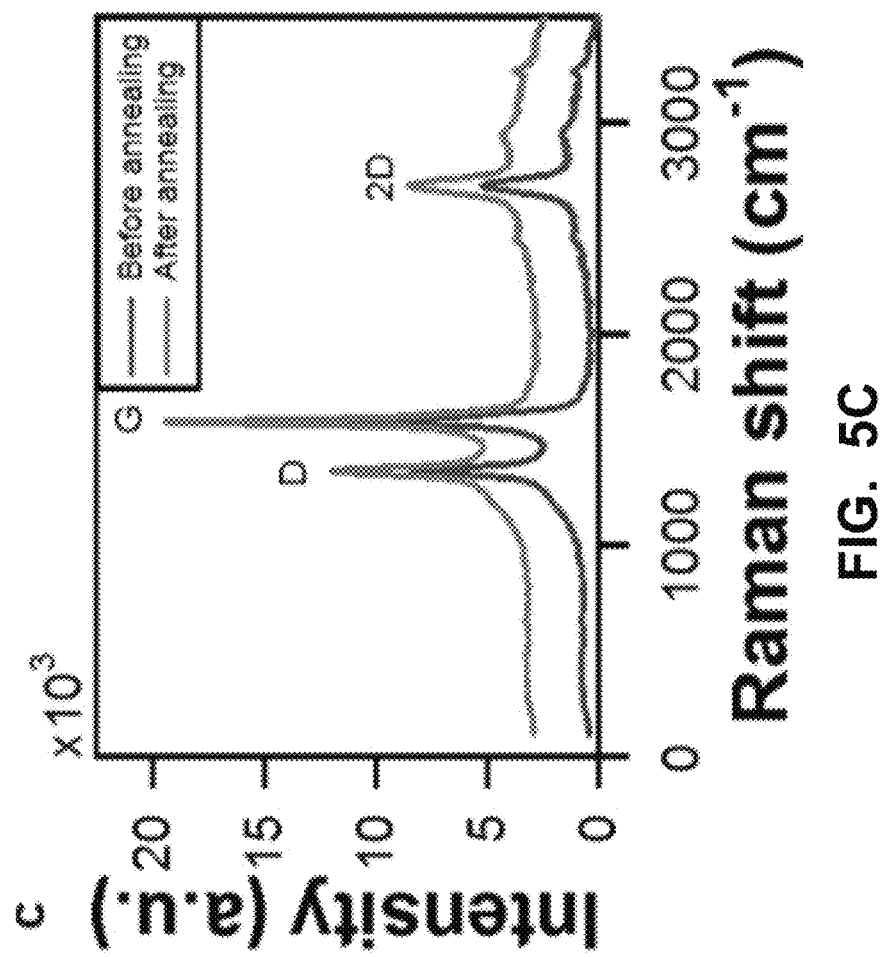

FIGS. 5A-C. Spectroscopy of the graphene IDE. Fig.: XPS of graphene IDE before $CO_2$ thermal annealing. FIG. 5B: XPS of graphene IDE after $CO_2$ thermal annealing. FIG. 5C: Raman spectroscopy of printed graphene IDE before and after $CO_2$ thermal annealing with D, G and 2D peaks displayed.

Figures 6A, 6B:
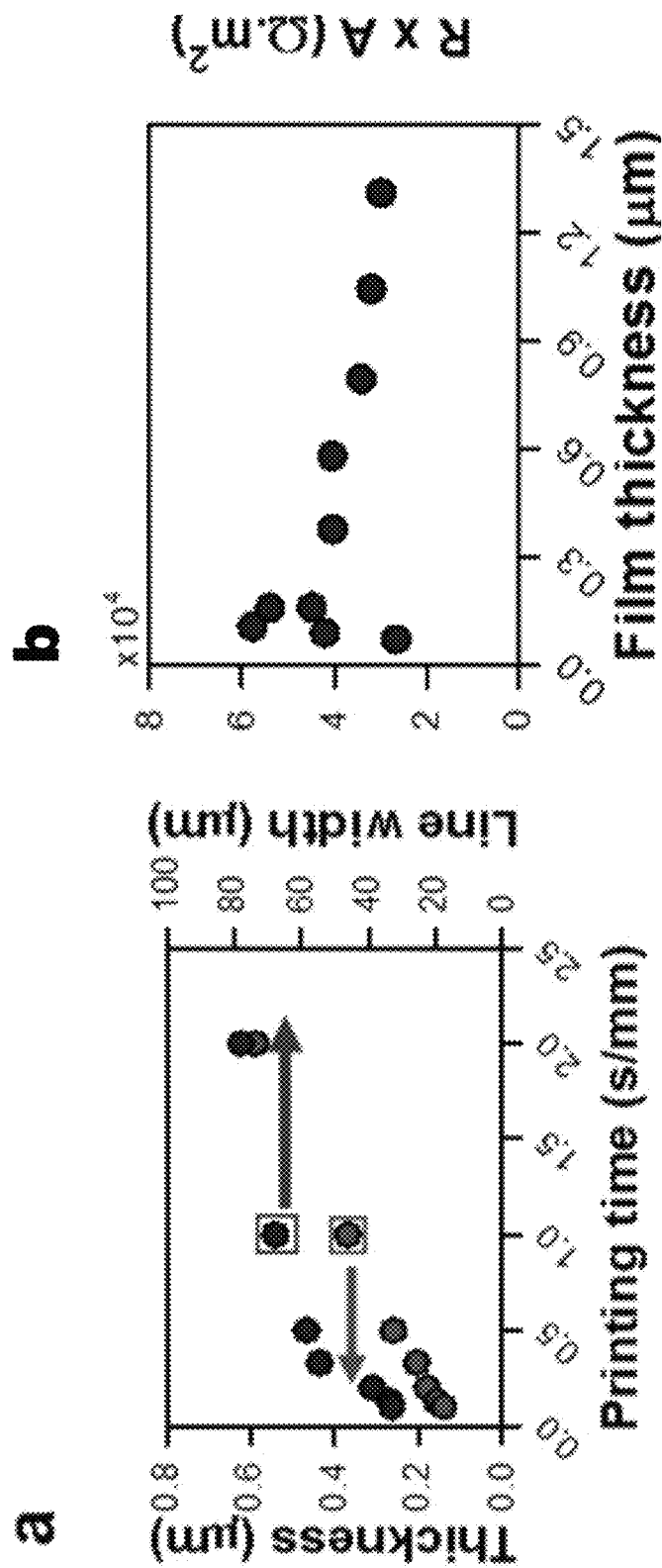
Figure 6D:
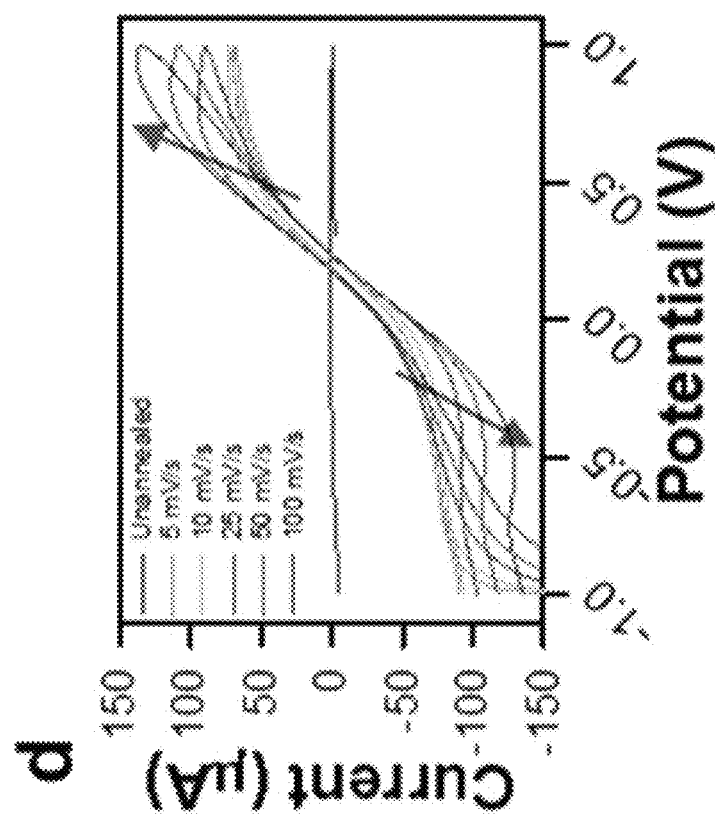
Figure 6C:
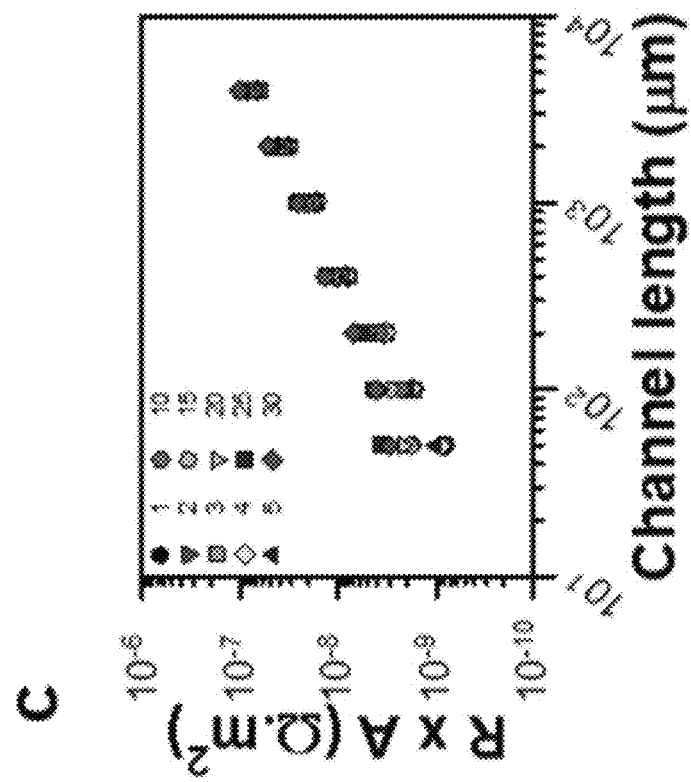
Figure 6F:
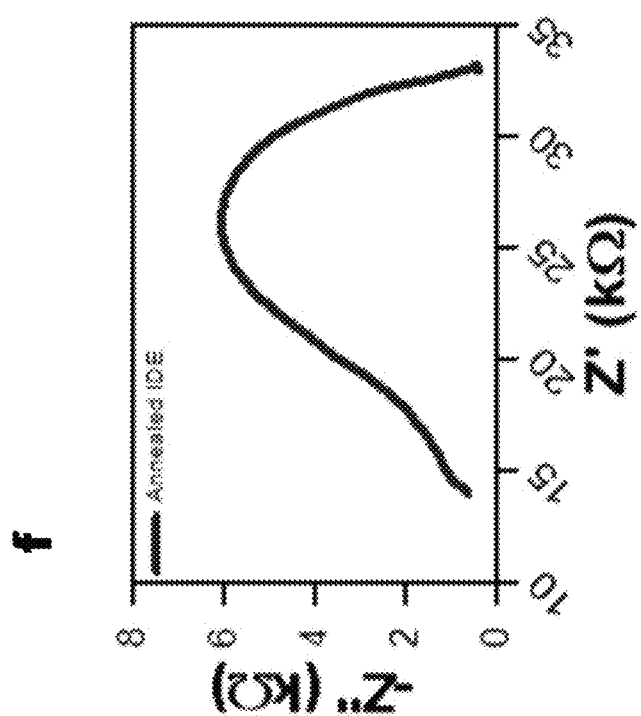
Figure 6E:
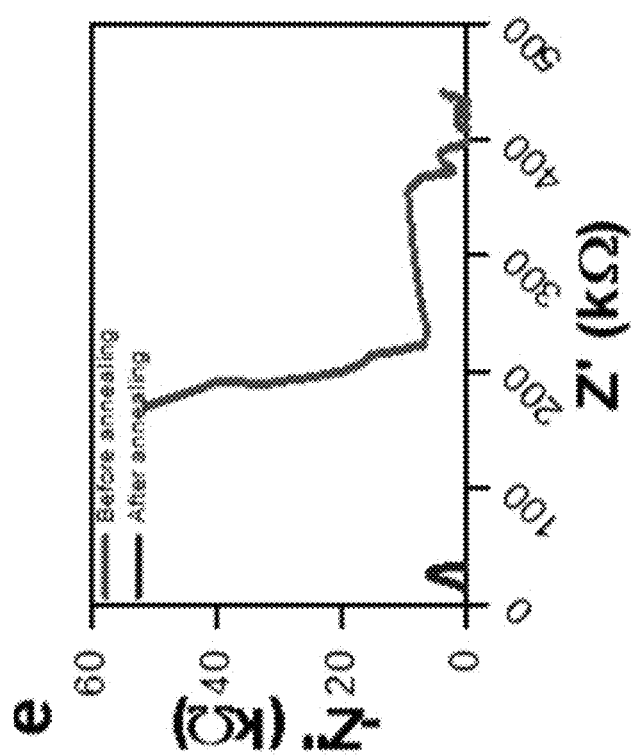

FIGS. 6A-F. FIG. 6A: Analysis of several lines printed at 55 sccm sheath flow, 35 sccm carrier flow, and various print speeds shows that the line thickness and line width both vary with printing time (s/mm), which is the inverse of printing speed (mm/s). FIG. 6B: A plot of conductivity vs. maximum film thickness for graphene lines printed on Kapton® shows that conductivity increases with film thickness up to about 200 nm before declining. FIG. 6C: Relationship of resistance multiplied by cross-section area vs. dimensions of the printed graphene line analogous to an IDE finger for various printing passes (indicated by the legend, i.e., 1, 2, 3, 4, 5, 10, 15, 20, 25, 30). The slope of the plot denotes resistivity of printed graphene. Electrochemical characterization of the graphene IDE showing FIG. 6D: cyclic voltammetry (CV) before $CO_2$ annealing and after $CO_2$ annealing at a scan rate of 5, 10, 25, 50 and 100 mV/s and FIG. 6E: Nyquist plot acquired from electrochemical impedance spectroscopy (EIS) before and after $CO_2$ thermal annealing. FIG. 6F: Magnified version of the Nyquist plot of the annealed IDE as shown in the lower left corner in FIG. 6E displays a characteristic semi-circular Nyquist plot.

Figure 7D:
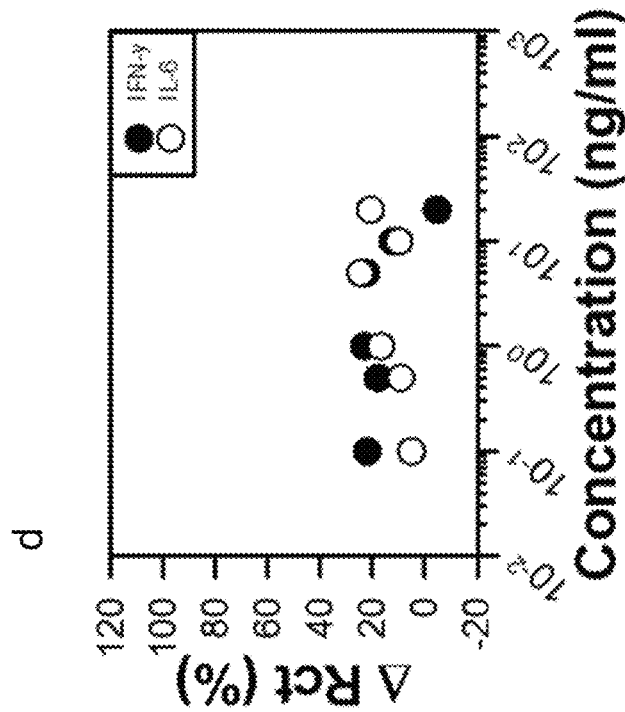
Figure 7C:
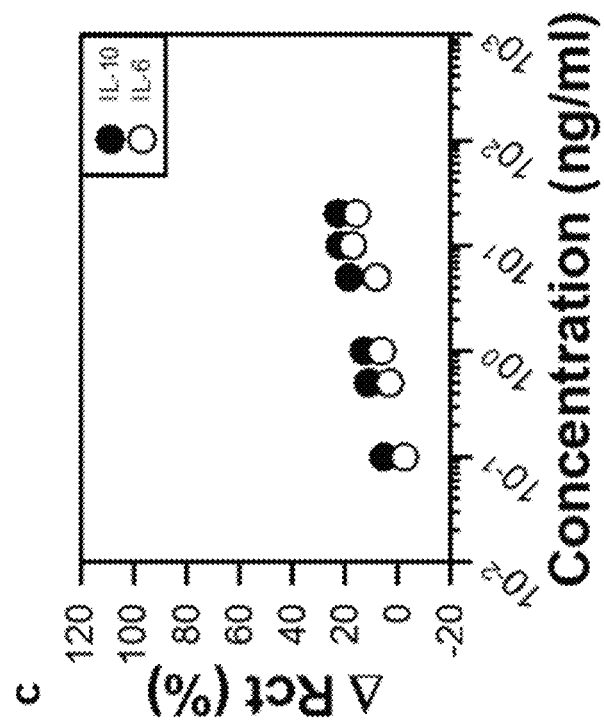

FIGS. 7A-D. FIGS. 7A-B: IFN-γ and IL-10 detection using graphene IDE sensors. Percentage change of charge transfer resistance ($R_{ct}$) with respect to the change of concentration of FIG. 7A: IFN-γ and FIG. 7B: IL-10. Error bars represent standard deviation of the mean calculated of three independently biofunctionalized electrodes with respective bovine monoclonal antibodies. FIGS. 7C-D. Selectivity test of FIG. 7C IFN-γ antibody with IL-10 and IL-6 antigen and (d) IL-10 antibody with IFN-γ and IL-6 antigen.

Figure 8A:
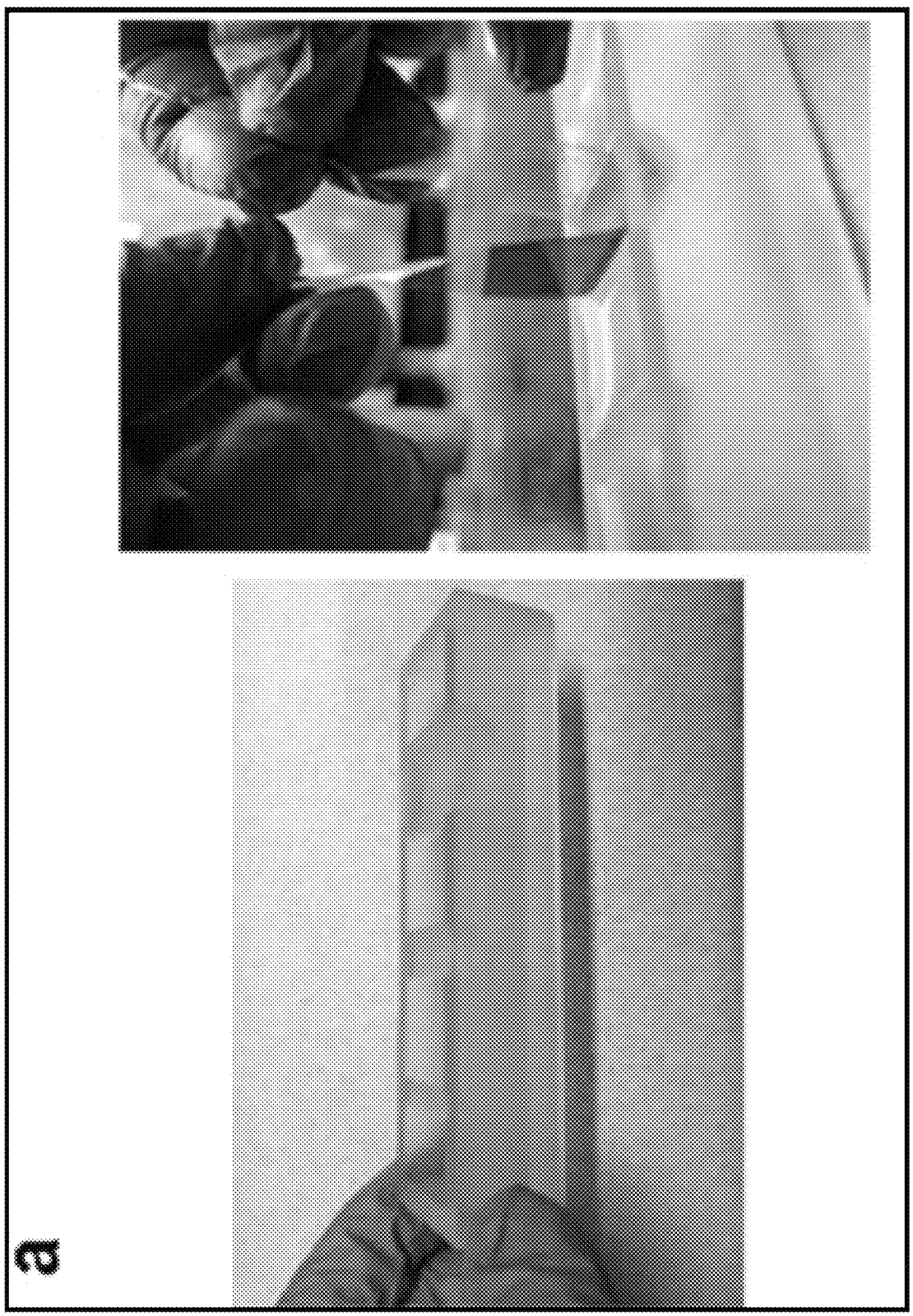
Figure 8C:
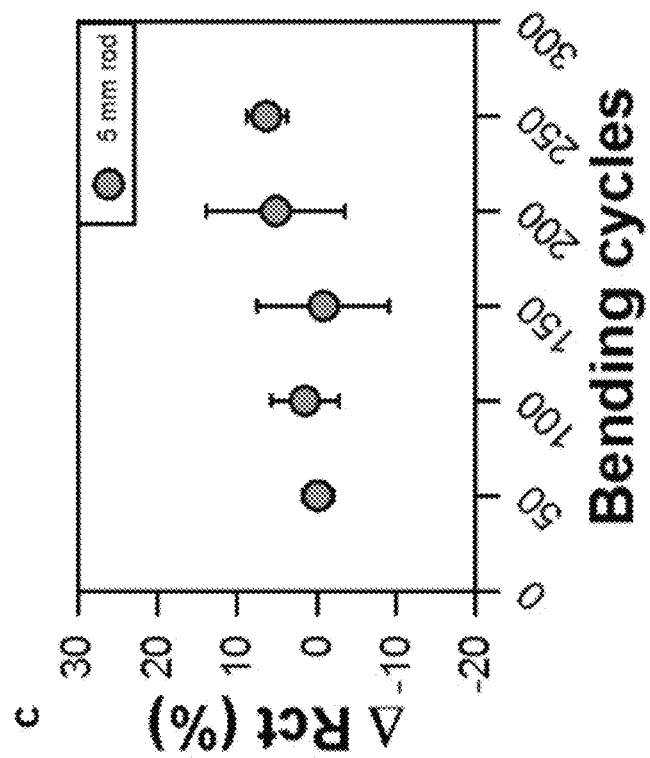
Figure 8B:
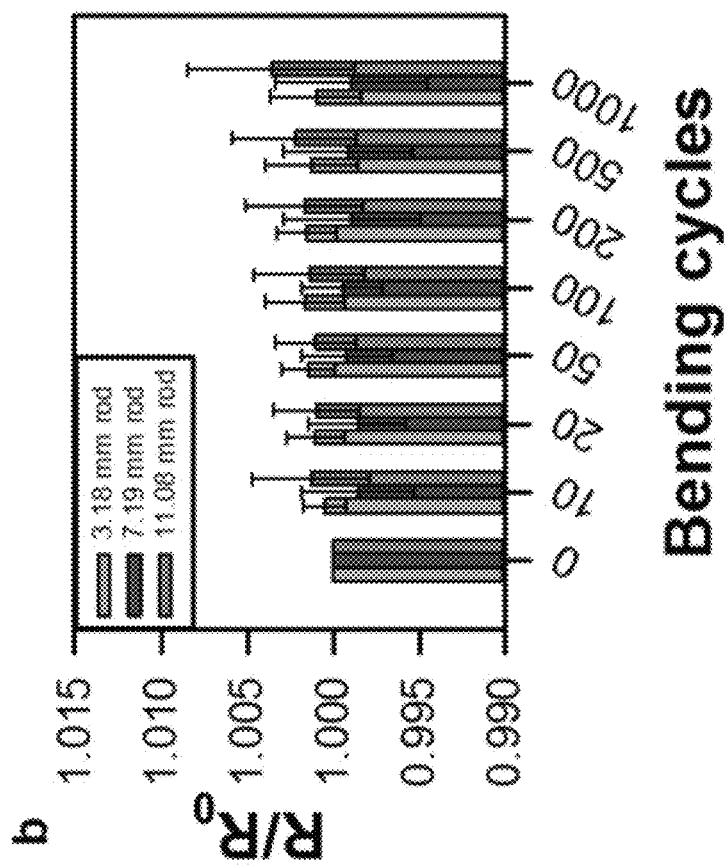

FIGS. 8A-C. Bending test experiments with the AJP graphene IDE. FIG. 8A: Photograph of the test set-up showing the IL-10 functionalized biosensor bending around a rod that is suspended within a 3D printed trough filled with PBS. FIG. 8B: Change in the resistance of AJP graphene IDE vs. the number of bending cycles without any biofunctionalization. FIG. 8C: $R_{ct}$ vs. the number of bending cycles of the biosensor around a rod (dia. 5 mm).

Figures 9C, 9D:
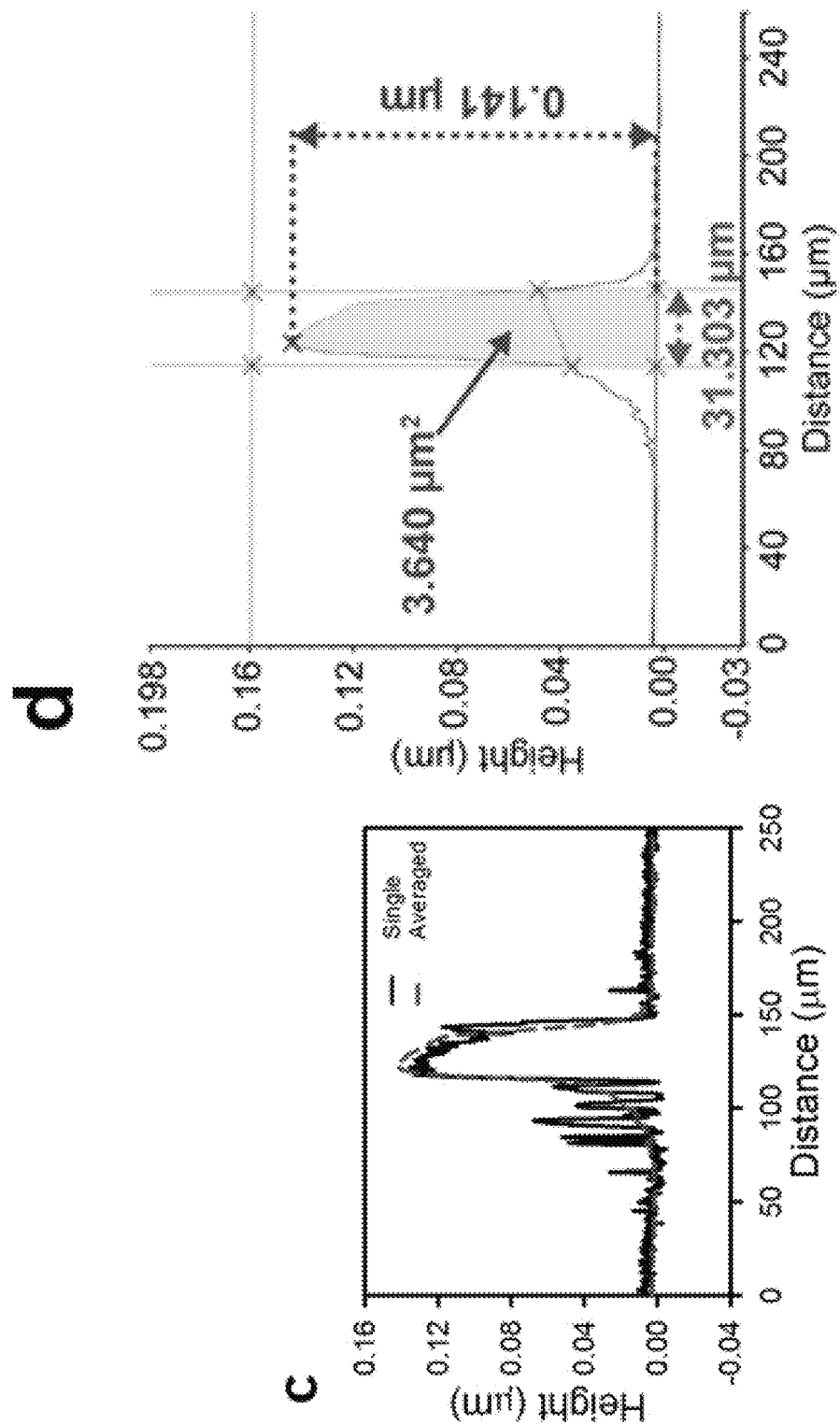
Figure 9F:
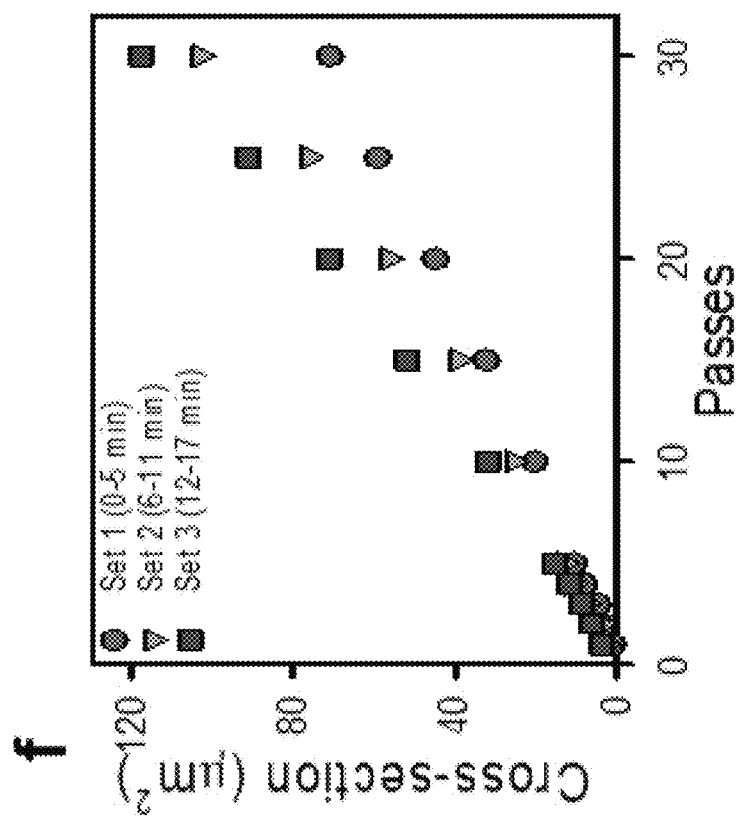
Figure 9E:
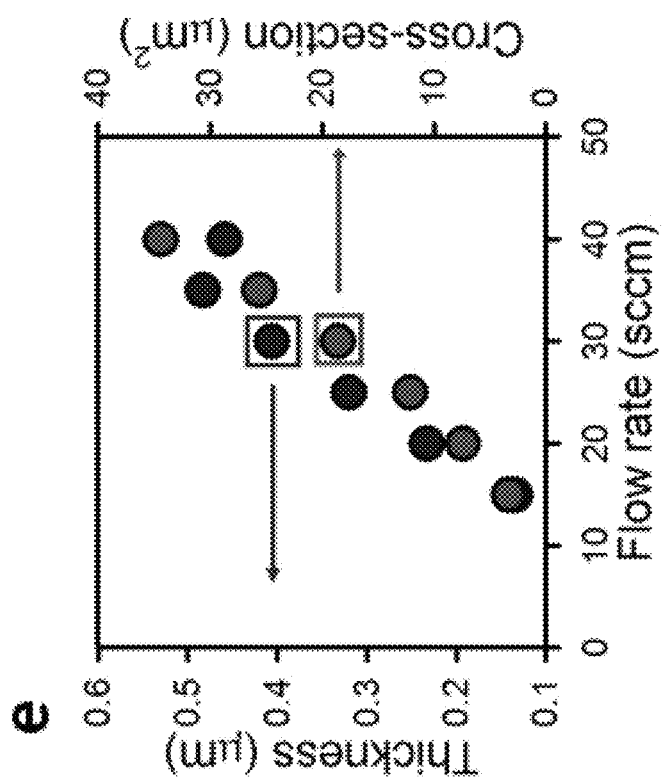

FIGS. 9A-F. Demonstration of tunable film thickness with printing parameters. FIG. 9A: Optical micrograph of printed graphene line on $SiO_2$. Line was printed at 55 sccm sheath flow, 35 sccm carrier flow, and 10 mm/s printing speed. FIG. 9B: 2D plot of the 3D profile of the printed graphene line. The horizontal line and boxed region represent the data sets used to generate the (FIG. 9C) single line profile and averaged line profiles, respectively. The averaged box region is 200 µm long. FIG. 9D: Measurement of average maximum line thickness, line width, and cross-sectional area can be extracted from the averaged line profile. FIG. 9E: Analysis of several lines printed at 1 mm/s with varying carrier flow rate and constant sheath flow of 55 sccm. FIG. 9F: Variation of the cross-section of printed graphene line with number of printing passes printed in sequential sets.

FIGS. 10A-D. Influence of printed graphene porosity on electrical properties. Cross-sectional and 45°-tilted top down SEM micrographs are shown for (FIGS. 10A-B) ultrathin (sub-100 nm thick) films and (FIGS. 10C-D) thicker films that are printed on $SiO_2$. Porosity is only observed in the thick limit.

Figure 11B:
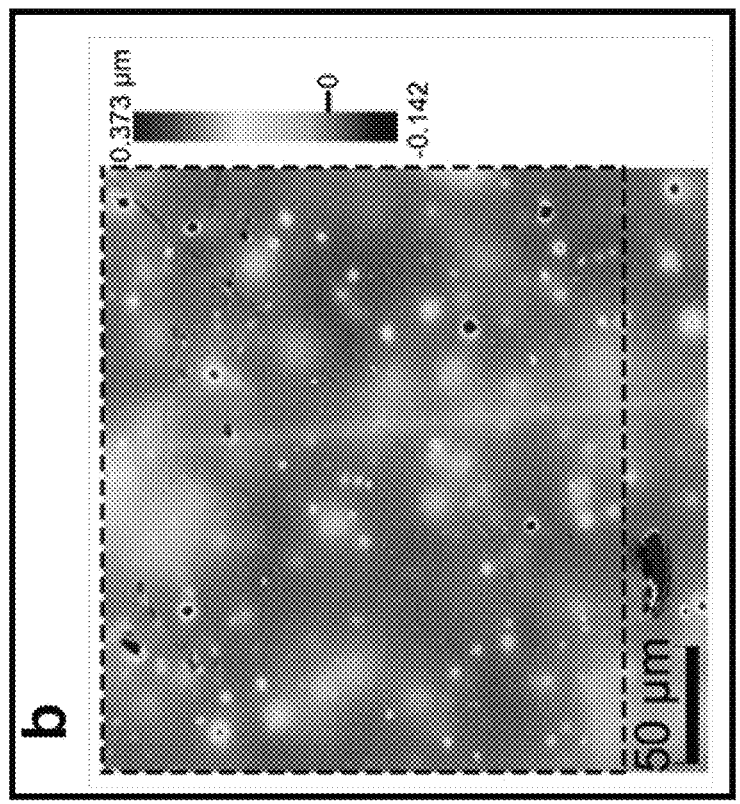
Figure 11A:
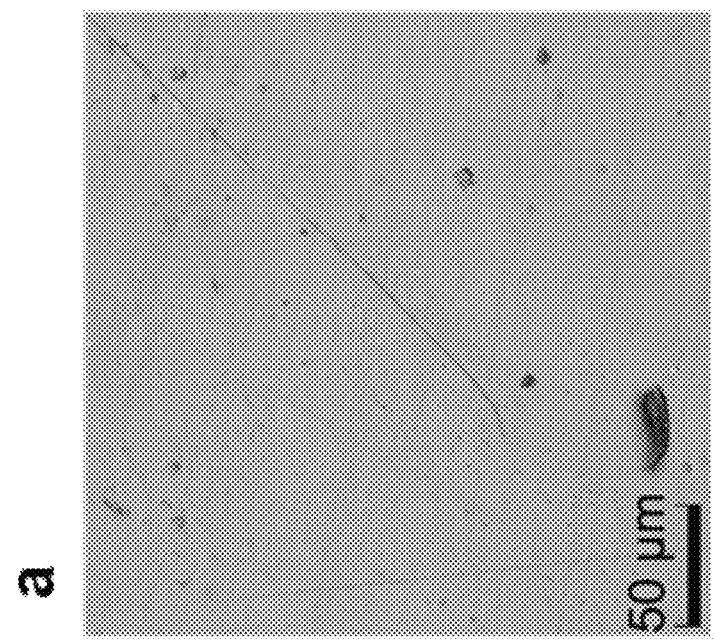
Figure 11D:
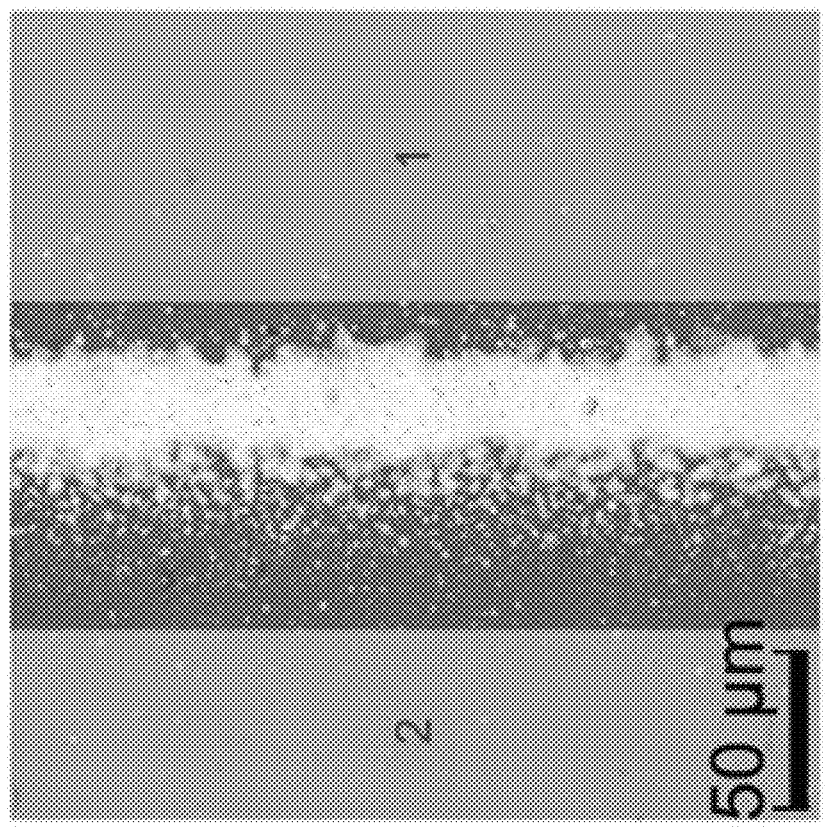
Figure 11C:
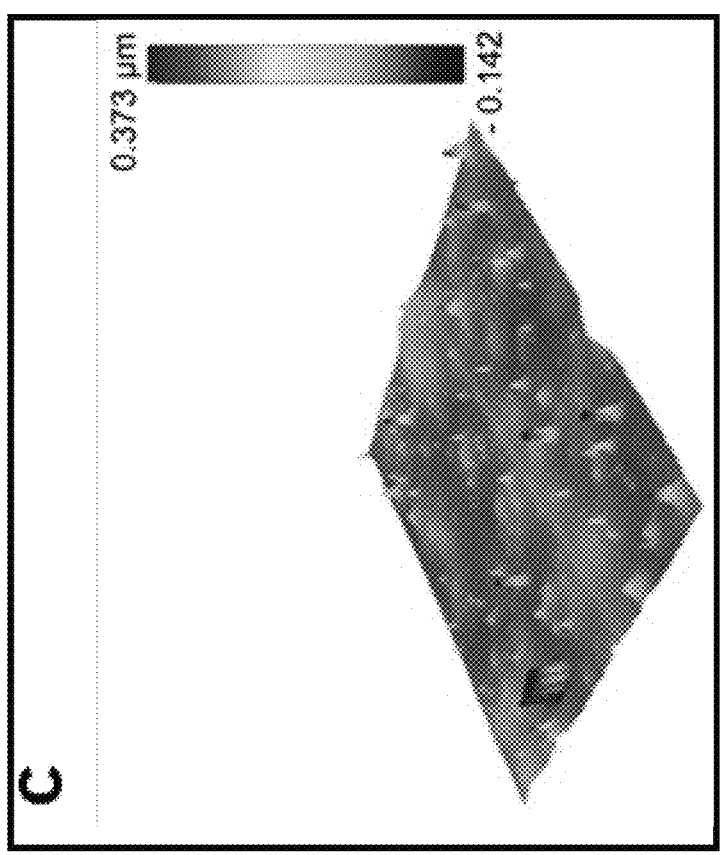
Figure 11F:
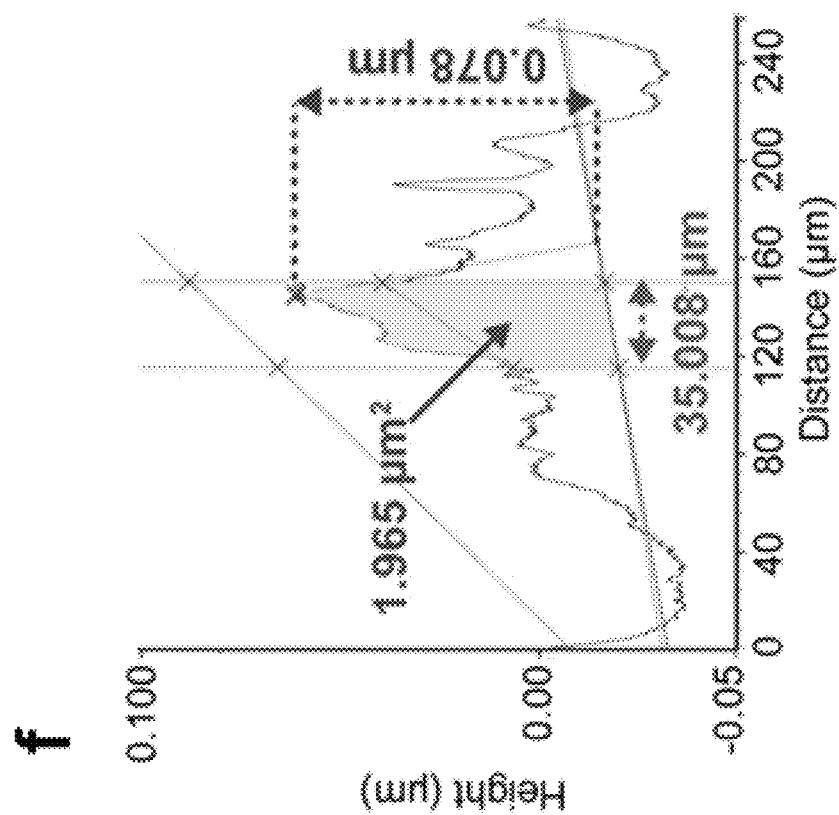
Figure 11E:
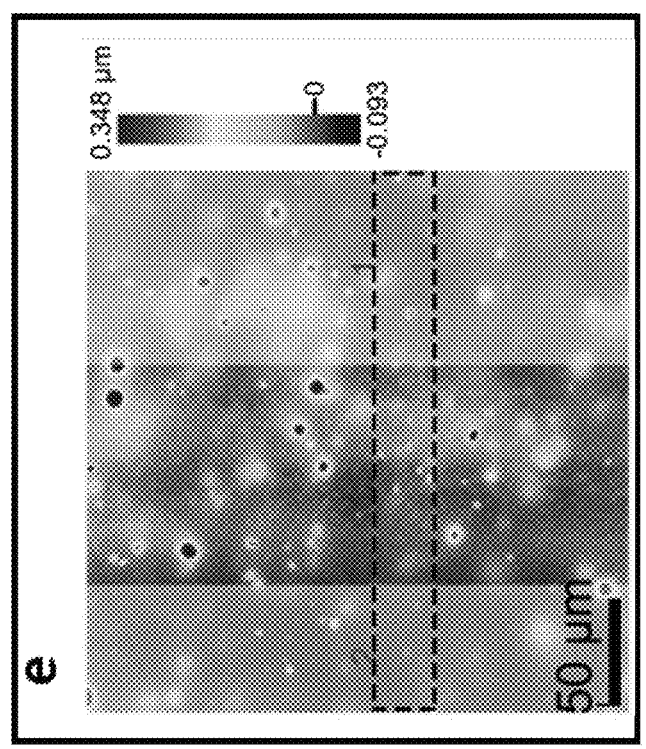

FIGS. 11A-F. Printed graphene line morphology on Kapton® film. The surface irregularity and roughness of bare, as-received Kapton® film is observed in (FIG. 11A) an optical micrograph, (FIG. 11B) 2D height image, and (FIG. 11C) 3D height image. The root-mean-square (rms) areal roughness in this film is 37 nm, which is similar to the rms areal roughness of regions of interest 1 and 2 observed in (FIG. 11D) an optical micrograph of an ultrathin (sub-100 nm) printed line. FIG. 11E: The 2D height profile of the printed line shows minimal distinction between the substrate and the printed line. FIG. 11F: An averaged line profile of the boxed region in (FIG. 11E) shows peaks that do not correspond to the printed line, indicating that printed line height data cannot be extracted easily using previous methods of measuring line thickness. A printed region that measures ~78 nm thick is probably closer to 38 nm of printed graphene line thickness.

Figure 12:
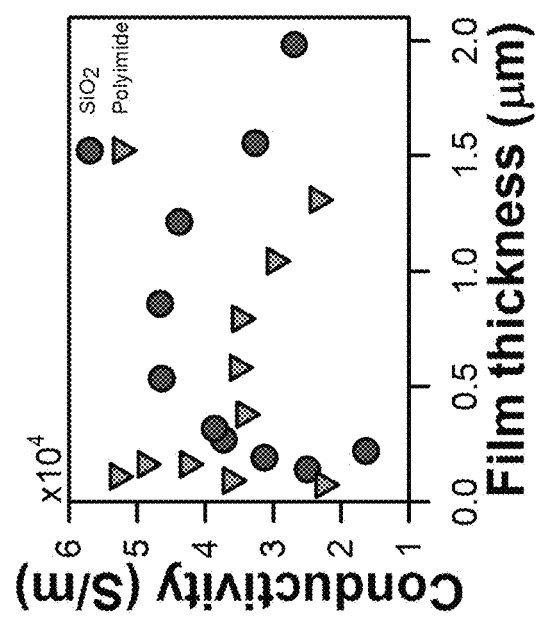

FIG. 12. Electrical conductivity measurement performed on graphene lines on $SiO_2$ and Kapton® substrate.

Figure 13A:
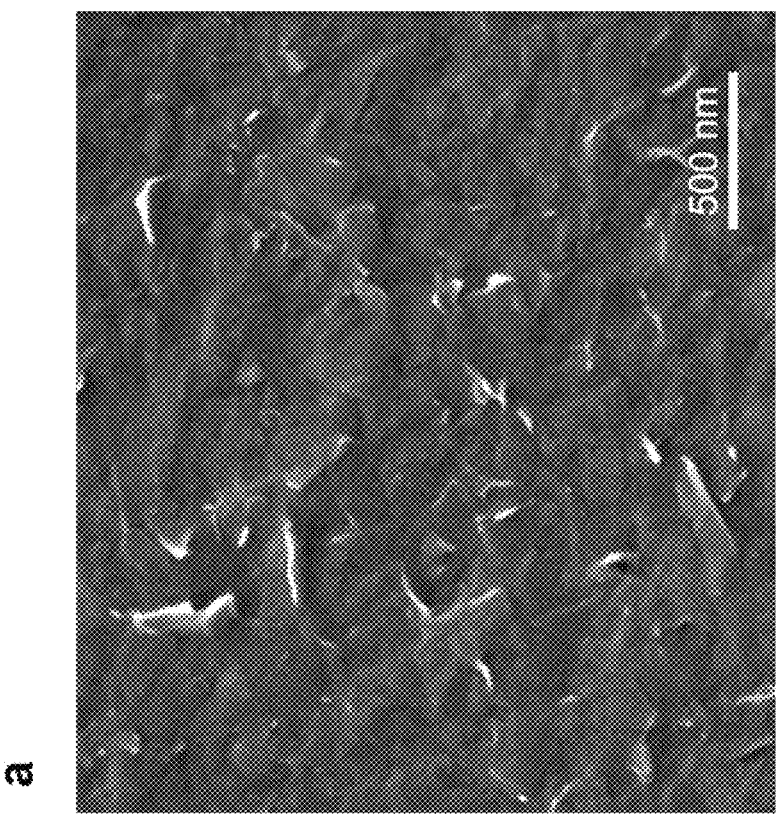
Figure 13B:
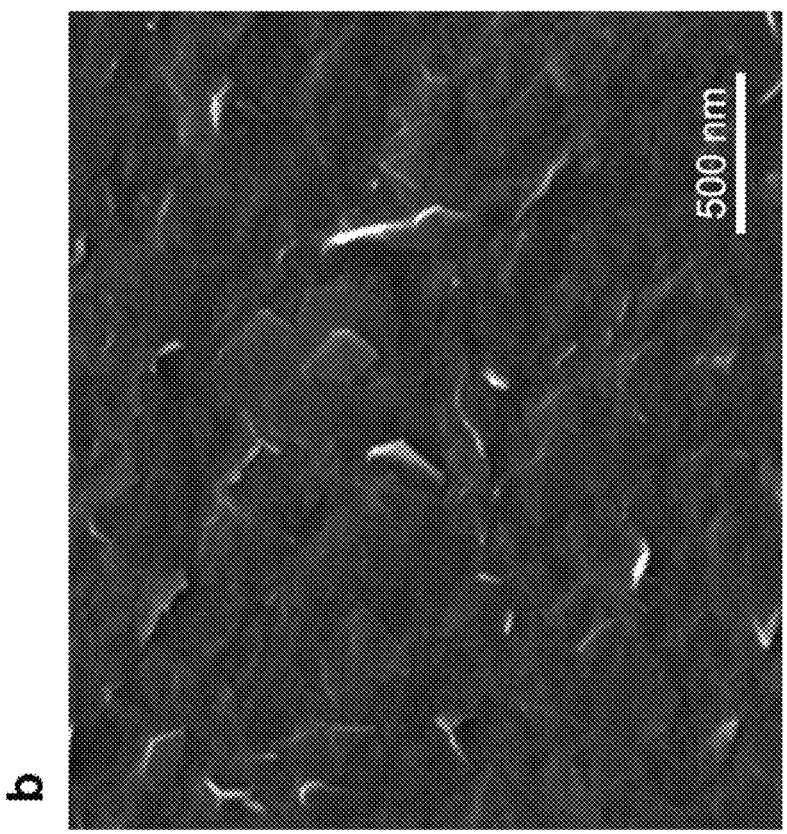

FIGS. 13A-B. Scanning electron microscopy images of AJP IDE (FIG. 13A) before $CO_2$ annealing, and (FIG. 13B) after $CO_2$ annealing.

Figure 14A:
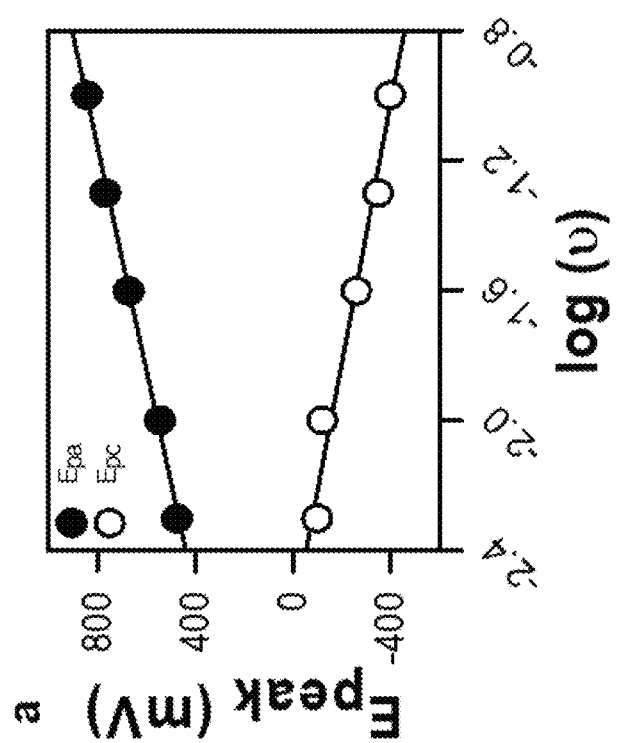
Figure 14B:
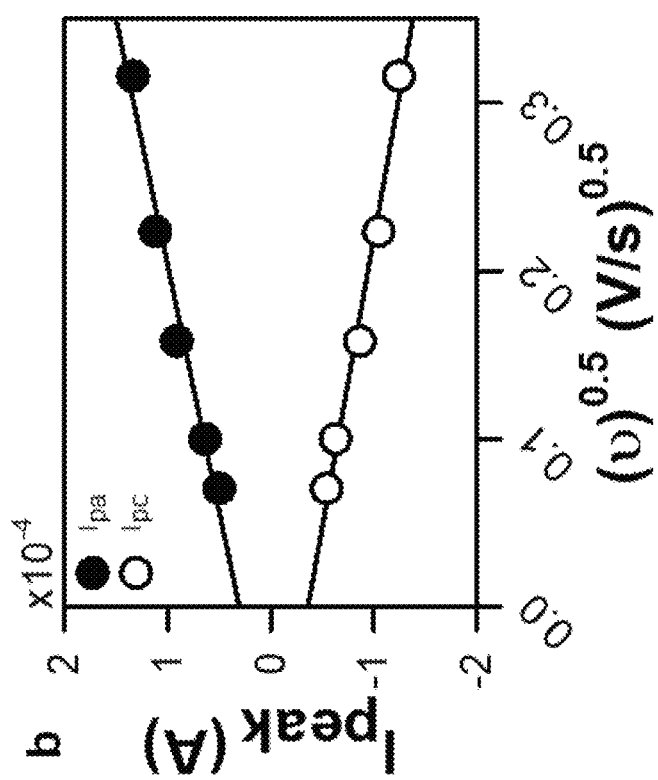
Figure 15C:
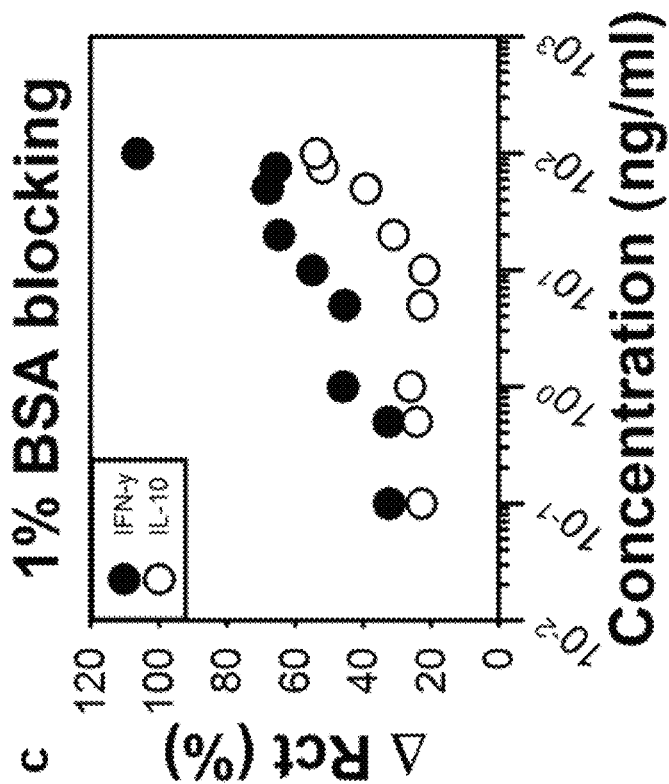
Figure 15B:
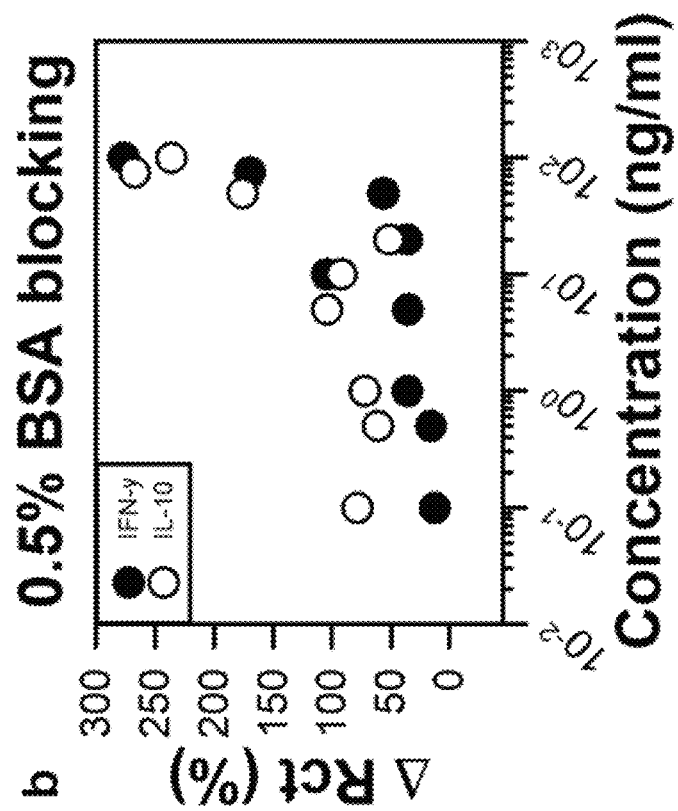

FIGS. 14A-B. Analysis for the calculation of electrochemical surface area. FIG. 14A: Plot of peak voltages versus logarithmic value of scan rate to calculate the charge transfer coefficient, $\alpha$; and (FIG. 14B) Randles-Sevcik plot depicting the variation of peak current versus square root of scan rate to determine the electrochemical surface area of the AJP IDE.

Figure 15A:
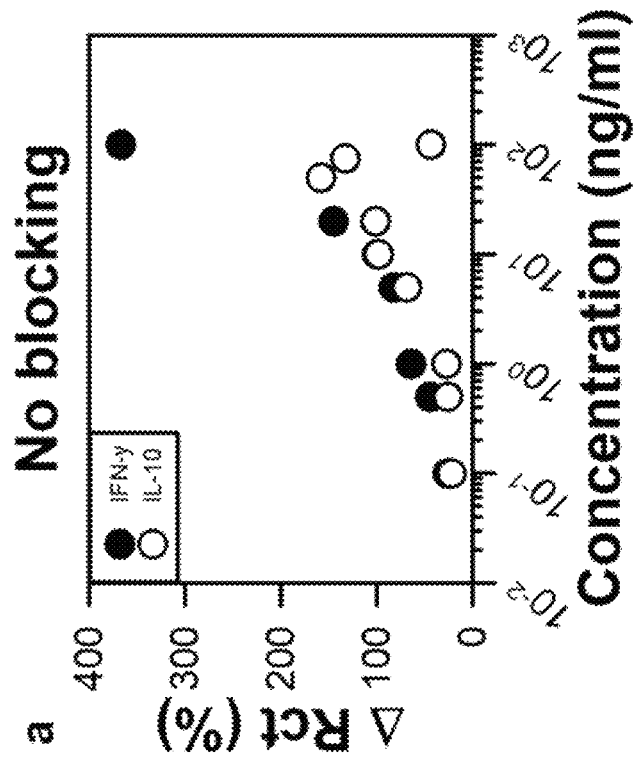

FIGS. 15A-D. Optimization of blocking buffer by testing the interference of IL-10 with IFN-γ antibody. FIG. 15A: Without blocking the IDE surface, (FIG. 15B) blocking with 0.5% BSA, (FIG. 15C) blocking with 1% BSA, and (FIG. 15D) blocking with 2% BSA. In all cases, IL-10 is showing non-specific binding and therefore has a high signal. Switching to a mixture of 1% BSA, 0.1% tween-20, and 0.1% fish gelatin reduces the interference from IL-10, and there is a distinguishable signal for IFN-γ.

Figure 16:
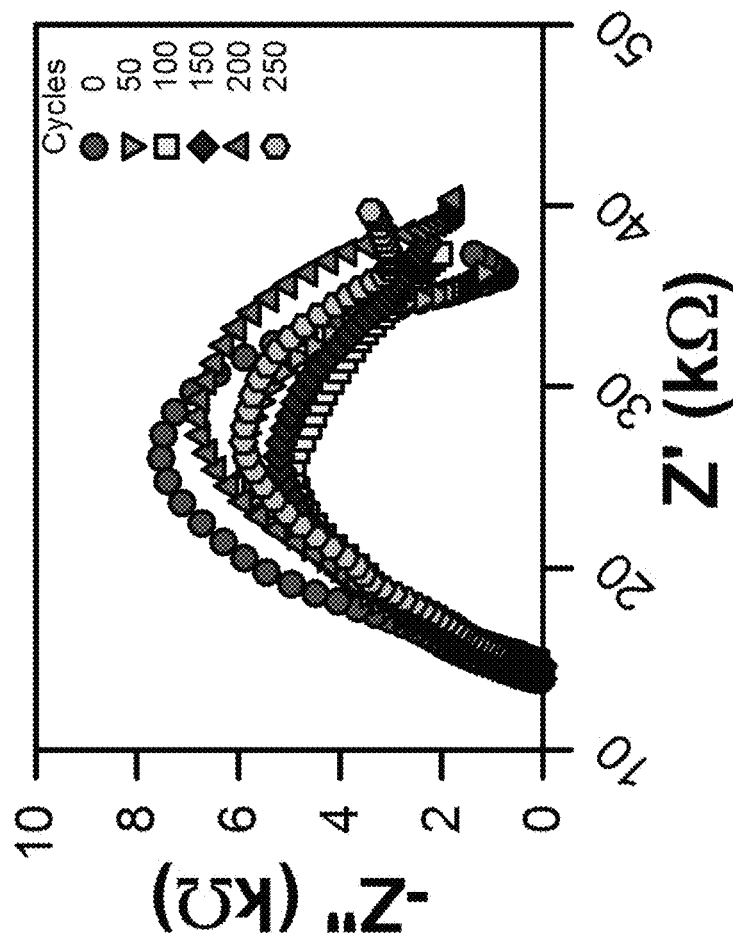
Figure 15D:
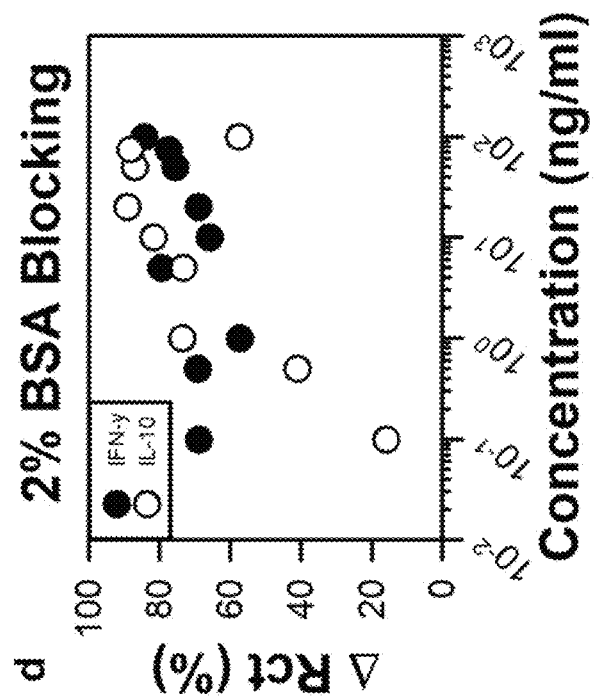

FIG. 16. A representative Nyquist plot for the bending test experiment with AJP graphene IDE performed with a rod of diameter 5 mm. The legend represents number of cycles for which a sensor was bent around the rod. The Nyquist plot was used for calculating the percentage change in $R_{ct}$ for different number of bending cycles w.r.t. $R_{ct}$ for a cytokine incubated biosensor that was not bent.

FIGS. 17A-E. Fabrication and biofunctionalization scheme of the AJP graphene biosensor including: (FIG. 17A) direct-write printing of graphene in an IDE pattern on a polyimide (Kapton®) sheet; (FIG. 17B) $CO_2$ thermal annealing to increase oxygenated species on the printed graphene surface; (FIG. 17C) immobilization of histamine antibodies on the IDE via carbodiimide cross-linking chemistry; (FIG. 17D) blocking the remaining unfunctionalized areas of the IDE with Superblock™ buffer to prevent non-specific adsorption during consequent biosensing; (FIG. 17E) histamine binding to the IDE and resulting Nyquist plot generated during electrochemical biosensing.

Figure 18C:
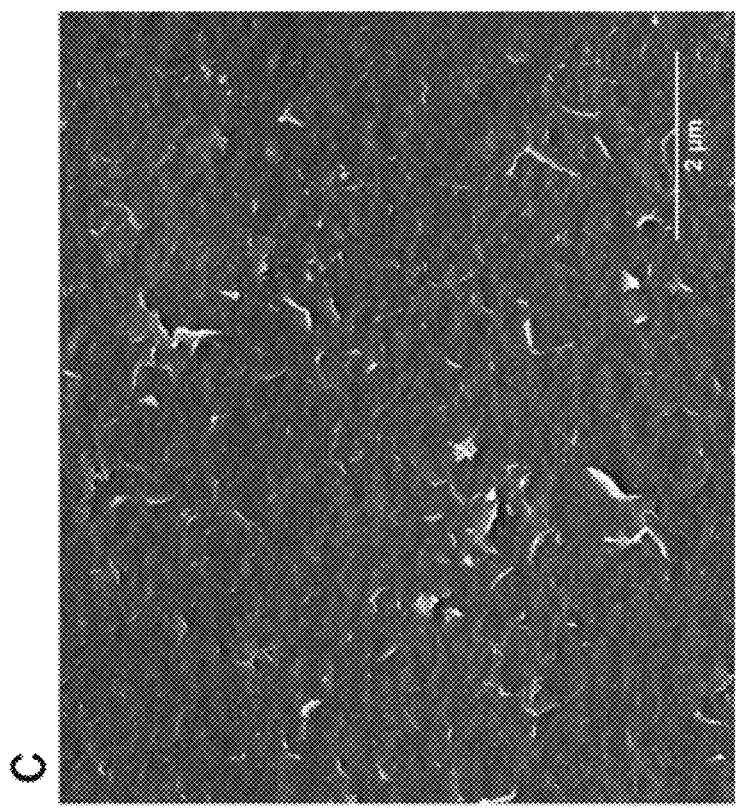
Figure 18B:
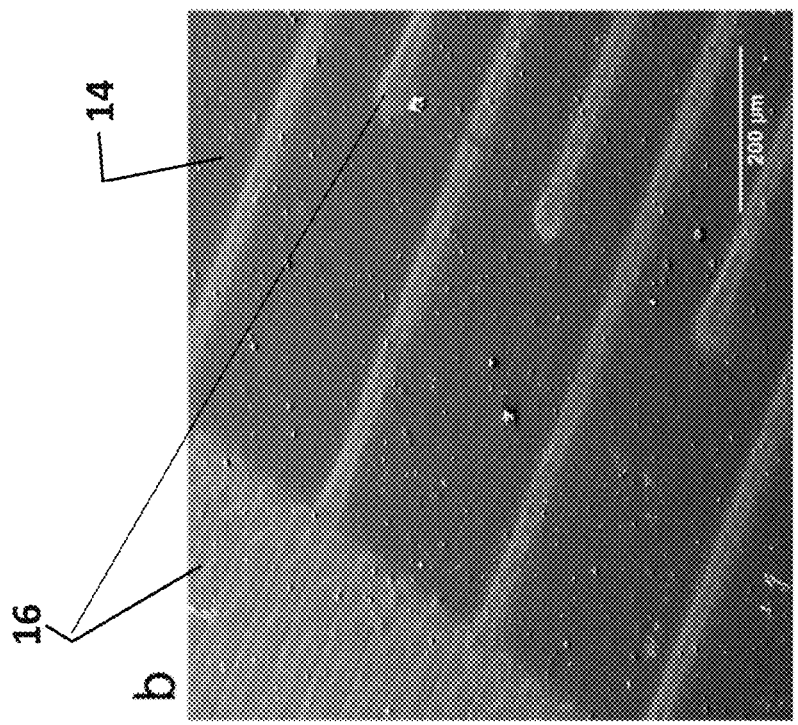
Figure 18E:
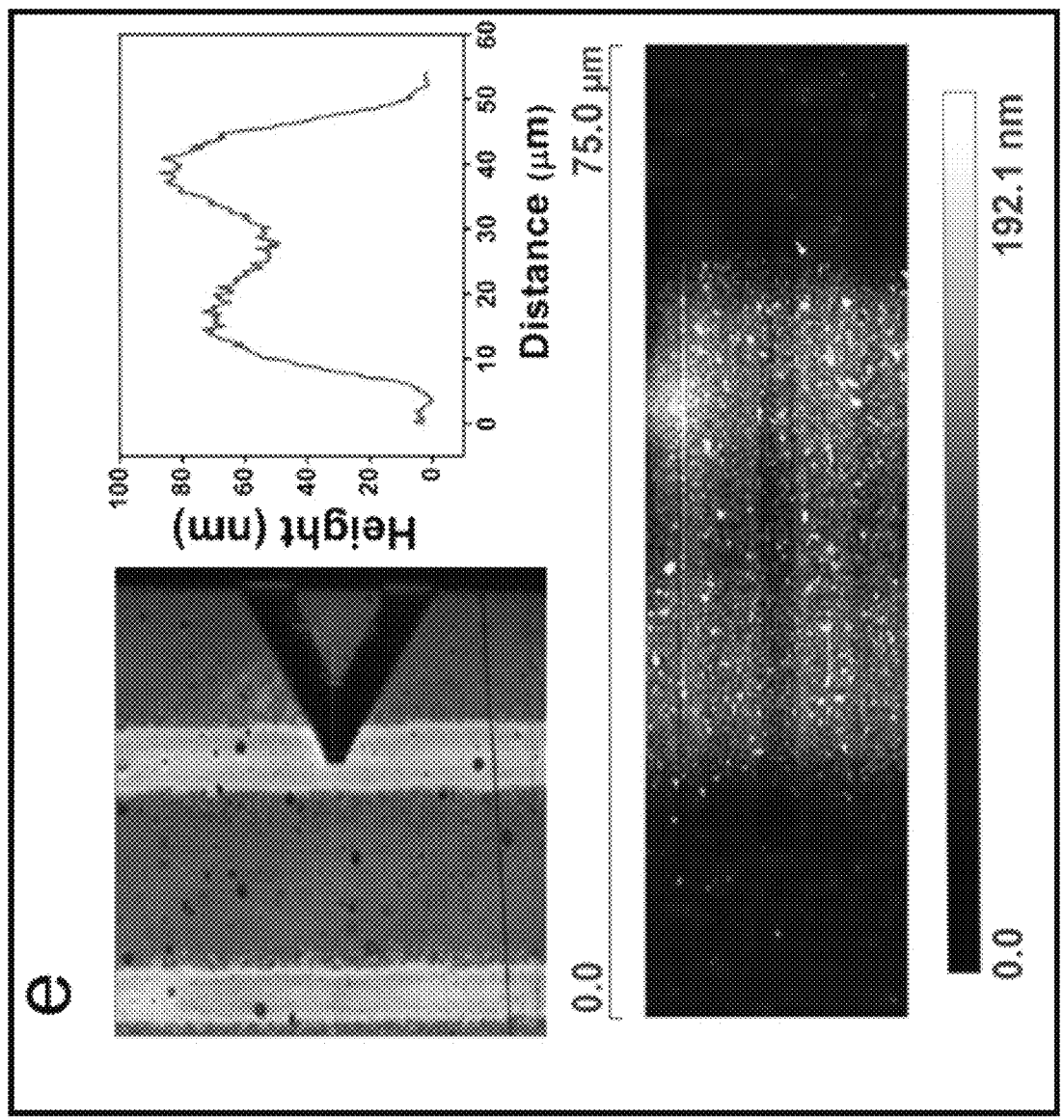
Figure 18D:
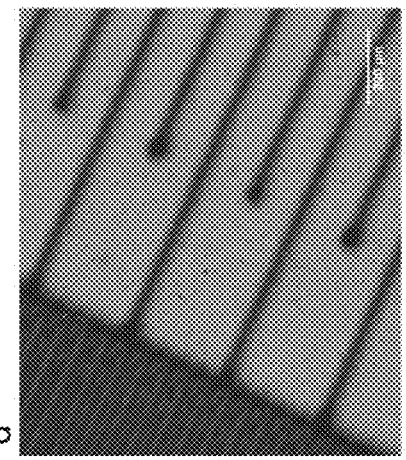

FIGS. 18A-E. Optical characterization of the AJP graphene IDE. (FIGS. 18A, D) Optical micrograph of the printed AJP IDE at 7× and 100× magnification, respectively, showing the high-resolution printed IDE fingers. (FIGS. 18B, C) SEM micrographs displaying surface topography of the graphene sheets printed on the polyimide sheet at 150× and 15000× magnification, respectively. FIG. 18E: Optical image of the AFM tip used for the measurement of the IDE finger height. AFM image of the graphene IDE finger showing the top area over which the AFM tip was scanned. Profile of the AFM micrograph showing the average film thickness of the graphene IDE finger is ~63 nm.

Figures 19A, 19B:
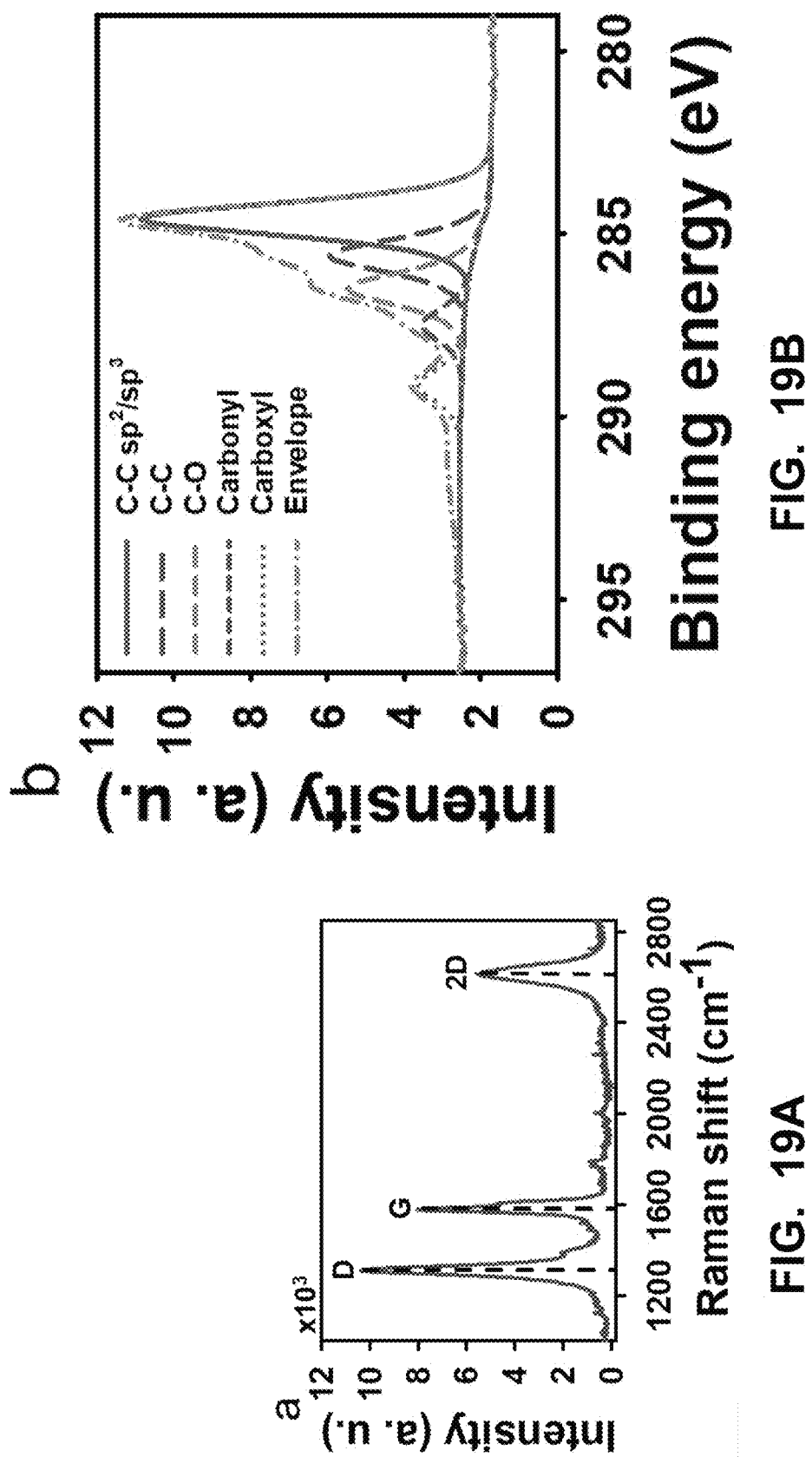

FIGS. 19A-B. FIG. 19A: Raman spectrum of an AJP graphene IDE on Kapton® showing the characteristic D, G, and 2D peaks of graphene. FIG. 19B: XPS of an AJP graphene IDE showing the surface functional groups.

Figures 20A, 20B:
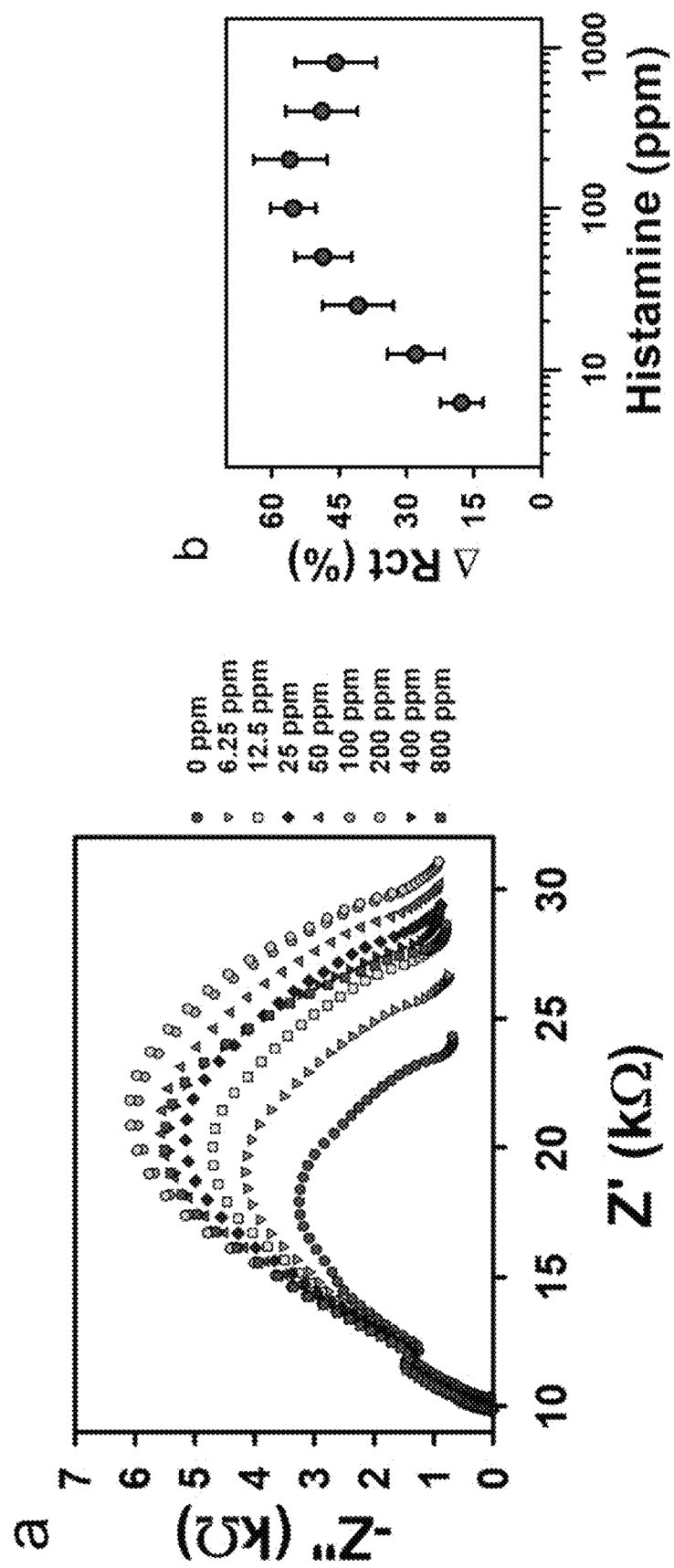
Figures 20C, 20D:
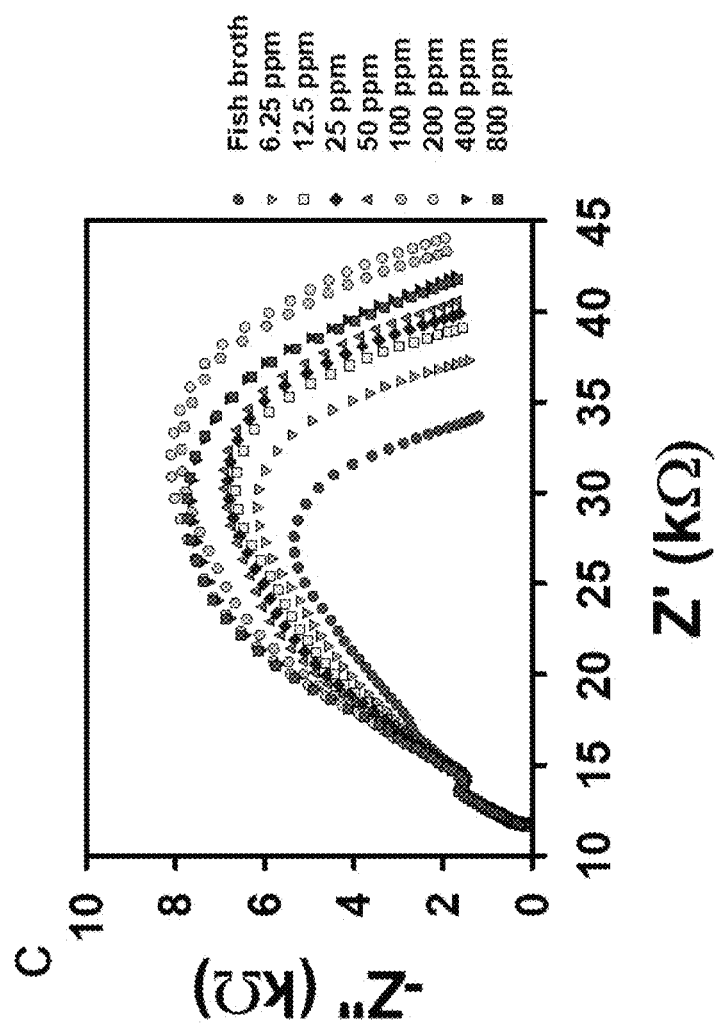

FIGS. 20A-D. Histamine detection using the AJP graphene IDE biosensor. FIG. 20A: Nyquist plots for each histamine concentration added to PBS. FIG. 20B: Calibration plot showing percent change of charge transfer resistance ($R_{ct}$) with respect to histamine concentration ranging from 6.25 to 800 ppm (56.25 μM to 7.2 mM) in PBS. Error bars represent the standard deviation calculated from 4 independently biofunctionalized electrodes (n=4). FIG. 20C: Nyquist plots for each histamine concentration added to fish broth. FIG. 20D: Calibration plot showing percent change of charge transfer resistance ($R_{ct}$) with respect to histamine concentration ranging from 6.25 to 800 ppm (56.25 μM to 7.2 mM) in fish broth. Error bars represent the standard deviation calculated from 5 independently biofunctionalized electrodes (n=5).

Figure 21:
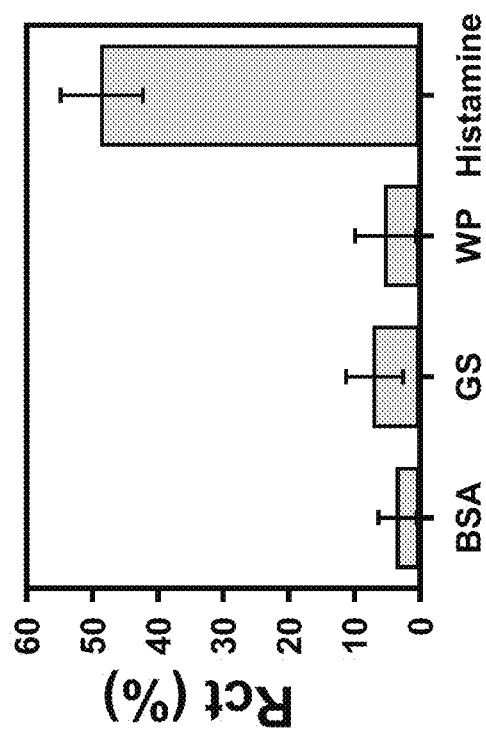

FIG. 21. Non-specific adsorption test of AJP graphene IDE biofunctionalized with histamine antibody against bovine serum albumin (BSA), goat scrum (GS), and whey protein (WP) to determine the effect of the incubation of the sensor in commonly found large protein molecules in food samples and used as blocking agents that can potentially interfere with the histamine antibody activity. All of the interfering proteins show a minimal change of $R_{ct}$ (<10%). Error bars represent the standard deviation calculated from 3 independently biofunctionalized electrodes (n=3).

Figure 22A:
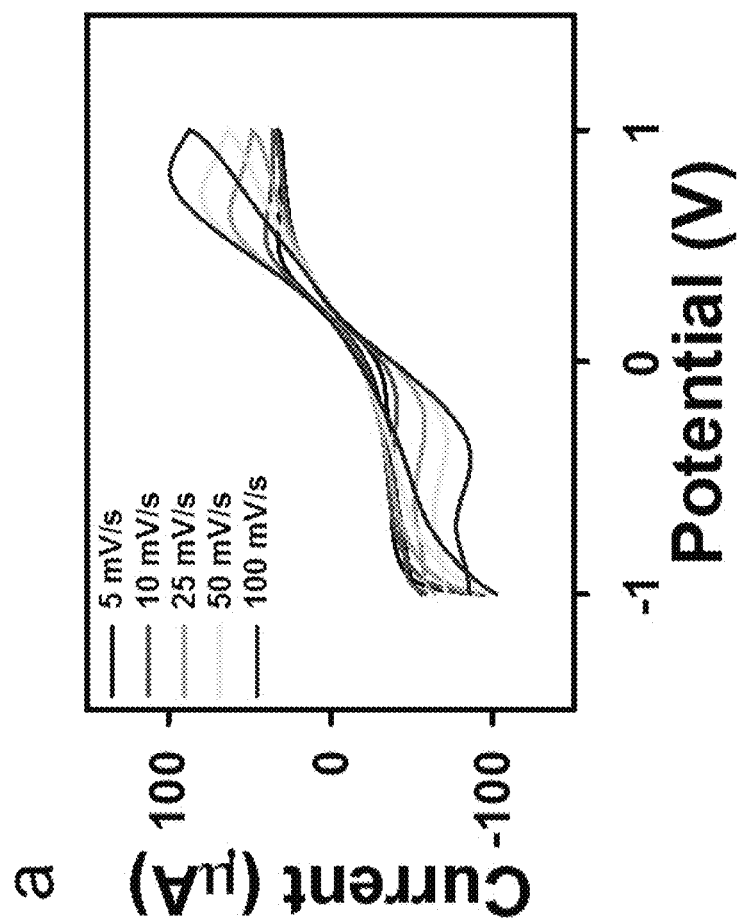
Figure 22C:
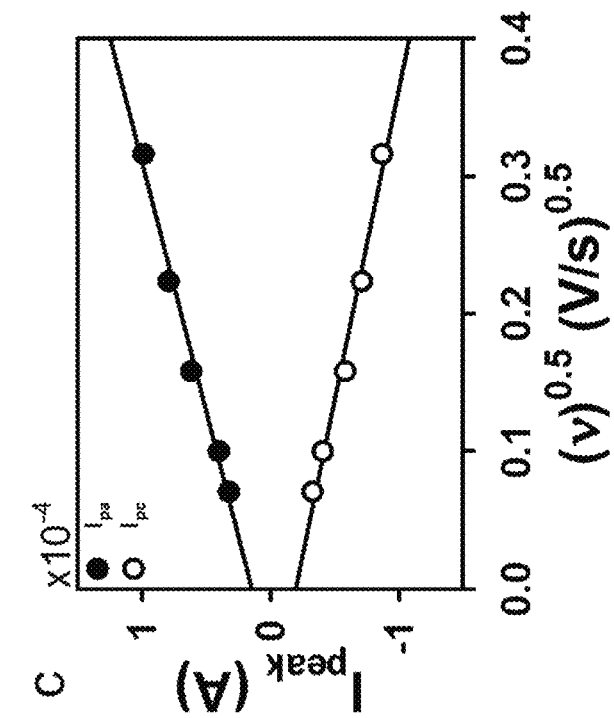
Figure 22B:
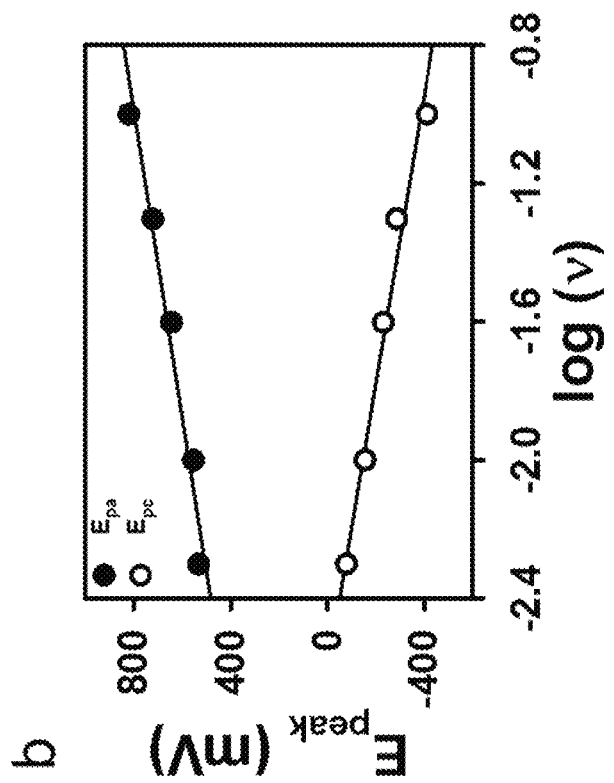

FIGS. 22A-C. Calculation of electrochemical surface area (ESA) for the AJP IDE. FIG. 22A: CV of the AJP graphene IDE at various scan rates (5, 10, 25, 50, 100 mV·s$^{-1}$). FIG. 22B: Plot of the peak voltages versus logarithmic value of the scan rate to calculate the charge transfer coefficient, $\alpha$; and (FIG. 22C) Randles-Sevcik plot showing a linear variation of the peak current with square root of the scan rate and using the resulting slope to calculate the ESA.

Figure 23:
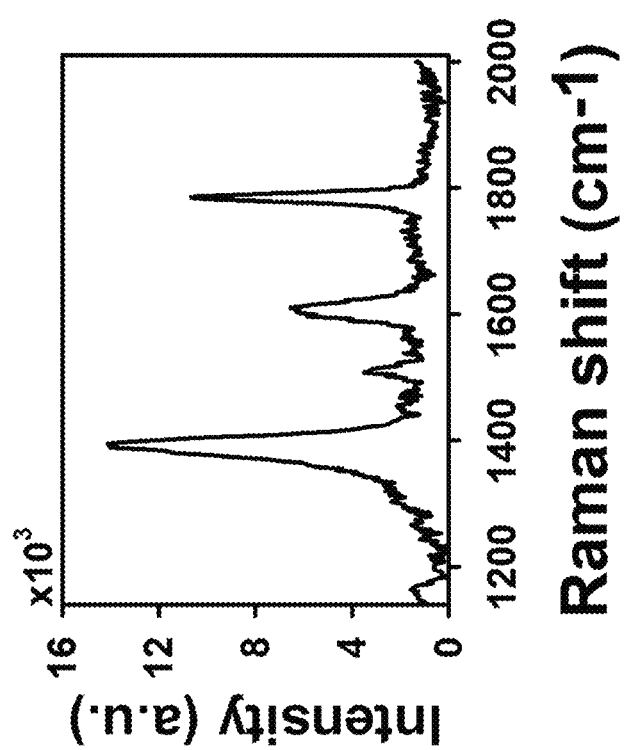

FIG. 23. Raman spectrum of the Kapton® substrate used in the aerosol jet printed graphene IDE, showing the peaks that correspond to the polyimide bands.

Figure 24A:
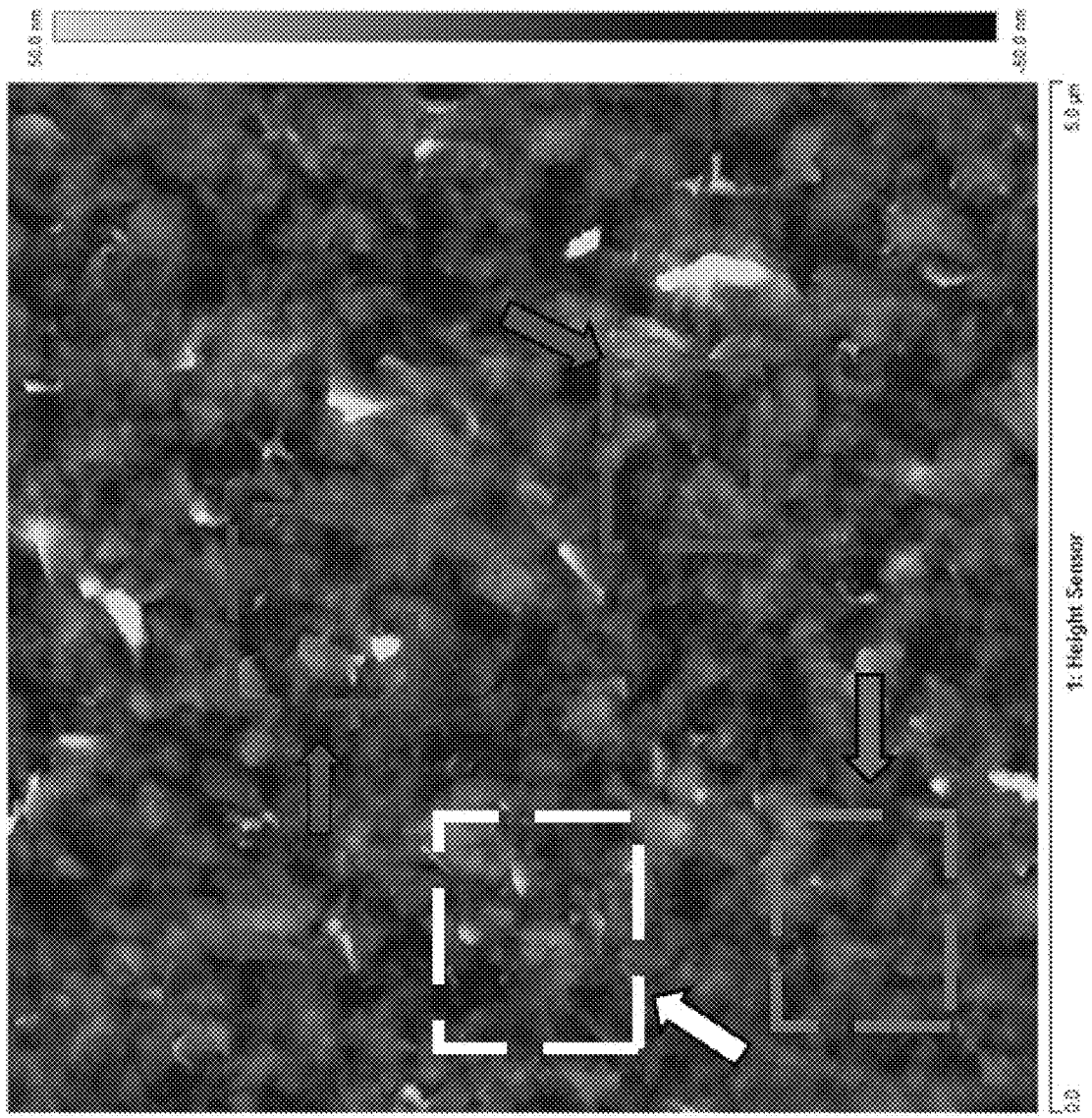
Figure 24B:
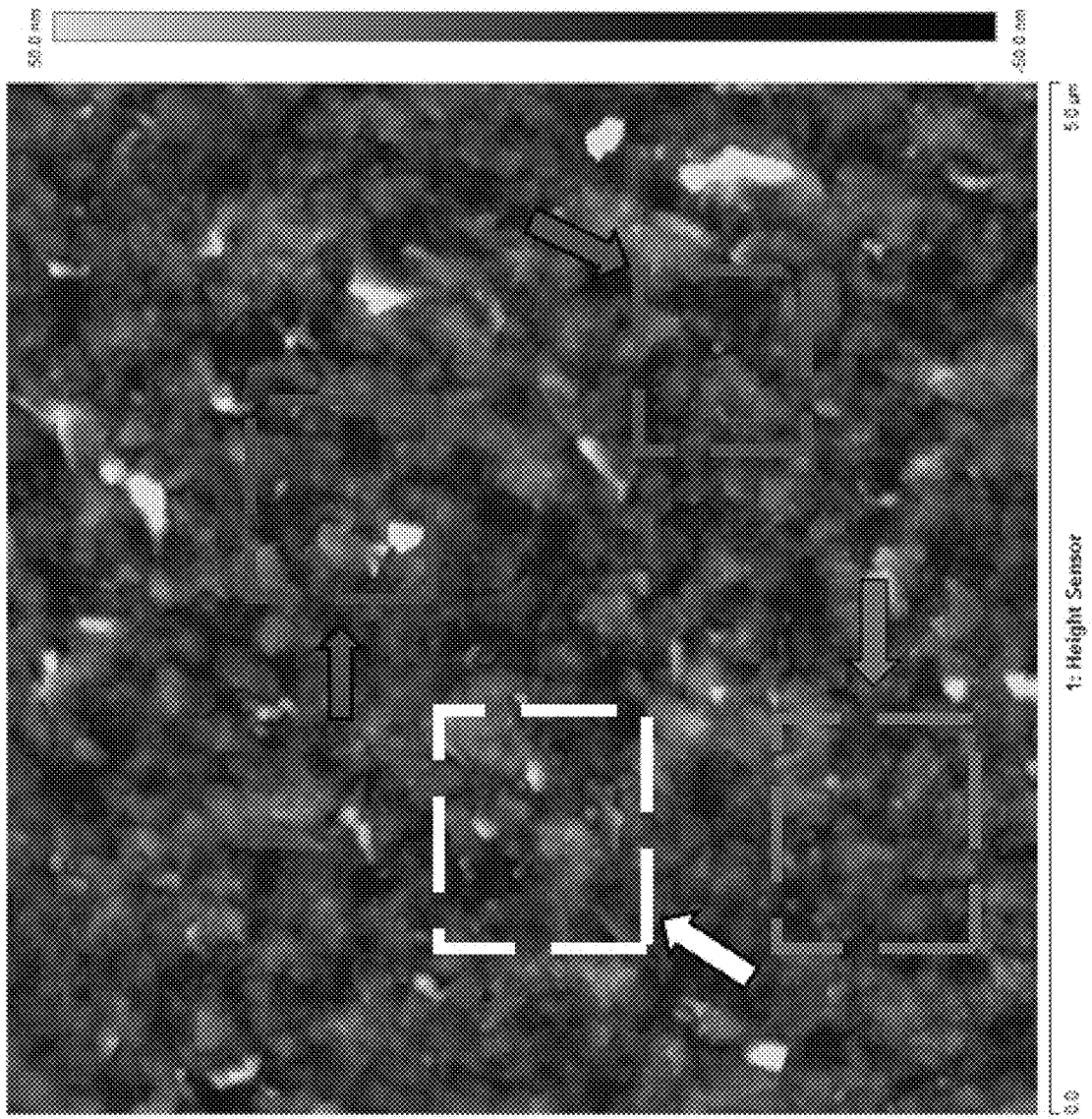

FIGS. 24A-B. Surface characterization of the AJP graphene IDE using AFM showing (FIG. 24A) untreated graphene surface, and (FIG. 24B) graphene surface functionalized with histamine antibody. The color coded dashed boxes represent corresponding areas where increase of surface texture is prominent with an increase in roughness of 3.7 nm after antibody immobilization.

IV. BACKGROUND INFORMATION

The documents listed in the table below supplement or provide background information. All of these are incorporated by reference as if fully a part of this description.

| | |
|---|---|
| Kshama Parate, Sonal V. Rangnekar, Dapeng Jing, Deyny L. Mendivelso-Perez, Shaowei Ding, Ethan B. Secor, Emily A. Smith, Jesse M. Hostetter, Mark C. Hersam, Jonathan C. Claussen | Aerosol-jet-printed graphene immunosensor for label-free cytokine monitoring in serum, ACS Appl. Mater. Interfaces 2020, 12, 7, 8592-8603. |
| Kshama Parate, Sonal V. Rangnekar, Dapeng Jing, Deyny L. Mendivelso-Perez, Shaowei Ding, Ethan B. Secor, Emily A. Smith, Jesse M. Hostetter, Mark C. Hersam, Jonathan C. Claussen | Supporting Information for ACS Appl. Mater. Interfaces 2020, 12, 7, 8592-8603. Available on-line at https://pubs.acs.org/doi/10.1021/acsami.9b22183 |
| Hondred, et al. | Enhanced electrochemical biosensor and supercapacitor with 3D porous architecture graphene via salt impregnated inkjet maskless lithography, *Nanoscale Horiz.*, 2019, 4, 735-746. |
| El-Terry, et al. | WO2019005708A2, published Jan. 3, 2019 Methods And Systems For Enabling And Scheduling 3d Printing-Based Fabrication |
| U.S. Government | Roll To Roll (R2R) Processing Technology Assessment, A Feb. 13, 2015_roll to roll mfg.pdf Available on-line at https://www.energy.gov/sites/prod/files/2015/02/f19/QTR%20Ch8%20-%20Roll%20To%20Roll%20Processing%20TA%20Feb-13-2015.pdf |
| Chou et al. | US2014/0035995A1, published Feb. 6, 2014, Aerosol Jet Printable Metal Conductive Inks, Glass Coated Metal Conductive Inks And UV-Curable Dielectric Inks And Methods Of Preparing And Printing The Same |
| King et al. | US2012/0231576A1, published Sep. 13, 2012, Aerosol Jet (R) Printing System For Photovoltiac Applications |
| Hersam, et al. | U.S. Pat. No. 9,834,693, issued Dec. 5, 2017, Methods for Preparation of Concentrated Graphene Ink compositions and related composite materials |
| Hersam, et al. | U.S. Pat. No. 9,902,866, issued Feb. 27, 2018, Methods for Preparation of Concentrated Graphene Ink compositions and related composite materials |
| Secor, E. B.; Cook, A. B.; Tabor, C. E.; Hersam, M. C. | Wiring up Liquid Metal: Stable and Robust Electrical Contacts Enabled by Printable Graphene Inks. *Adv. Electron. Mater.* 2018, 4 (1), 1700483. |
| Secor, E. B.; Gao, T. Z.; Islam, A. E.; Rao, R.; Wallace, S. G.; Zhu, J.; Putz, K. W.; Maruyama, B.; Hersam, M. C. | Enhanced Conductivity, Adhesion, and Environmental Stability of Printed Graphene Inks with Nitrocellulose. *Chem. Mater.* 2017, 29 (5), 2332-2340. |
| Secor, E. B.; Gao, T. Z.; Islam, A. E.; Rao, R.; Wallace, S. G.; Zhu, J.; Putz, K. W.; Maruyama, B.; Hersam, M. C. | Supplemental Information re: Enhanced Conductivity, Adhesion, and Environmental Stability of Printed Graphene Inks with Nitrocellulose. *Chem. Mater.* 2017, 29 (5), 2332-2340. Available on-line at 10.1021/acs.chemmater.7b00029 |
| Kshama Parate, Cicero C. Pola, Sonal V. Rangnekar, Deyny L. Mendivelso-Perez, Emily A. Smith, Mark C. Hersam, Carmen L. Gomes, Jonathan C. Claussen | Aerosol-jet-printed graphene electrochemical histamine sensors for food safety monitoring *2D Materials*, 7(3), [034002]. https://doi.org/10.1088/2053-1583/ab8919 |
| Kshama Parate, Cicero C. Pola, Sonal V. Rangnekar, Deyny L. Mendivelso-Perez, Emily A. Smith, Mark C. Hersam, Carmen L. Gomes, Jonathan C. Claussen | Supplemental Information for Aerosol-jet-printed graphene electrochemical histamine sensors for food safety monitoring *2D Materials*, 7(3), [034002]. https://doi.org/10.1088/2053-1583/ab8919 Available on-line. |

V. DETAILED DESCRIPTION OF EXEMPLARY EMBODIMENTS OF THE INVENTION

A. Overview

For a better understanding, several exemplary embodiments of aspects of the invention will now be presented in detail. These examples are neither inclusive or exclusive of the different forms the invention or its aspects can take. For example, variations obvious to those skilled in the art will be included.

B. Embodiment 1—Generalized Example

With reference to FIGS. 2A-C, several examples according to embodiments of the invention are illustrated, as further discussed below. As indicated at FIG. 2A, these examples have in common a direct additive printing method 100 and system 10. A graphene-based ink 11 is formulated (step 111). A high resolution pattern 16 of ink 11 is printed on a substrate 14 by additive printer 12 technique to create a printed substrate 20 (step 120).

Printed substrate 20 can be processed (at ref. no. 30 in FIG. 2A) by annealing by an annealing subsystem 32 to manipulate physical and electrical characteristics of the printed pattern 16 (step 130).

The result is a direct printed, high resolution patterned substrate 40 with characteristics designed for effective use in sensing applications. One example is that the pattern can function as a high resolution electrode or circuit on any of a variety of possible substrates, including flexible or thin substrates. The printing allows wide variability in the possible patterns.

FIG. 2B is similar to FIG. 2A. It illustrates one version of the more generalized method 100 and system 10 of FIG. 2A is use an aerosol jet printing (AJP) as the mode of additive printing. An AJP printer 12' would print an ink 11' formulated for AJP. As exampled further herein, AJP as the additive printing mode can have certain benefits.

FIG. 2C illustrates that additional method steps can be conducted on the annealed printed substrate 50 of either FIG. 2A or 2B. Annealed printed substrate 50 on its own has important features over the state of the art. But as indicated as arrow "A" at the bottom of FIG. 2B, annealed printed substrate 50 of either FIG. 2A or 2B can be further processed as follows.

The annealed printed pattern 16 of device 50 can be functionalized for specific applications (step 150). As will be discussed in more detail in specific exemplary embodiments herein, one example is with binding agents 51 (e.g. antibodies) that bind with specific molecules of interest in an analyte. According to some embodiments of the invention, this functionalization can be improved by a second annealing (step 160). That second annealing can be with the same heating component as step 130, or a different technique/component/subsystem 62. This second-time annealing device 60 can provide for benefits in the functionalize or its ultimate effectiveness as sensing.

In some embodiments, a blocking agent 71 can be added to the device 60 (step 170). The advantages are discussed infra. A blocked, functionalized device 80 can then be adapted to bind molecules of interest 81 of an analyte presented to the functionalized device 80 for binding and electrical-based sensing.

1. Features

First, high resolution, high-throughput electrochemical sensing circuits can be created utilizing aerosol jet printing of pristine graphene flakes on a substrate. The graphene flakes are included in an ink composition that is effective for these purposes. The printing is controllable and scaleable. The substrate could vary, including materials such as a paper or other flexible sheets, films, or fabrics. The substrate and printed circuits can be fabricated with additive manufacturing techniques. Because it does not require subtractive manufacturing, the fabrication can be relatively economical.

Second, post-print annealing effective to convert electrochemically inactive printed graphene into one that is electrochemically active can be employed. One example is $CO_2$ annealing. The printing can be by aerosol jet printing, but is not necessarily limited thereto. An example is inkjet printing and then the post-print annealing. The ink formulation would be adjusted for effectiveness with inkjet printing. This $CO_2$ annealing process converts an electrochemically inactive printed graphene to one that is electrochemically active. The cyclic voltammograms and electrochemical impedance spectroscopy plots in FIGS. 6D and E show how unannealed graphene is electrochemically inactive then how $CO_2$ annealing converts the graphene into an electroactive material that could be used to detect electroactive species in solution (e.g., hydrogen peroxide, dopamine, uric acid, acetaminophen).

Third, a method of covalently binding biorecognition agents to aerosol printed graphene for the purpose of electrochemical biosensing can be utilized. Post-print annealing, for example $CO_2$ annealing discussed above, can also substantially increase the amount of oxygen species on the surface of the graphene as exhibited in the x ray photoelectron spectroscopy plots in FIGS. 5A and B. These oxygen species are then needed to covalently bind antibody to the graphene surface for subsequent electrochemical biosensing. Hence the $CO_2$ annealing enables both electrochemical sensing (sensing of analytes in solution without a biorecognition agent immobilized on the surface) and biosensing (sensing of analytes in solution with a biorecognition agent) in solution.

2. Composition

As mentioned, a composition that can be effectively additively applied at high resolution to a variety of substrates, including those that might be degraded or destroyed by other techniques (e.g. paper or flexible/plastic substrates), is utilized. In one example, a composition comprising graphene or graphene oxide exfoliated from graphite is produced for use in a printable ink formulation. Specific examples for aerosol jet printing will be discussed in the Specific Embodiment 2 infra. One way to produce the same is through a low-cost bulk synthesis process.

The specific formulation for the printable ink can vary. For example, if the technique of printing is aerosol jet printing, the formulation can differ than if inkjet printing is used. Some of the ink constituents are different or are used in unique concentrations or combinations for aerosol printing than inkjet printing. For example, we have demonstrated that graphene-nitrocellulose powders could be formulated into inks for inkjet printing or aerosol printing (see our attached prior patents and the attached manuscript). However, to make the ink amenable to aerosol jet printing unique solvent combinations need to be used in conjunction with the graphene-nitrocellulose powders than inkjet printing. In particular we demonstrate that graphene-nitrocellulose powder was found to form a stable dispersion in 9:1 ethyl lactate:dibutyl phthalate cosolvent system and was amenable to consequent aerosol jet printing. Dibutyl phthalate has a boiling point of 340° C., so it prevents aerosol droplets from evaporating completely before deposition on the substrate. Dibutyl phthalate remains in the printed feature until subsequent baking, and its presence allows graphene nanosheets to "relax" into a flat morphology. Moreover, a graphene ink with 30 mg/mL solids loading was prepared and filtered through a 3.1 µm membrane prior to printing. Such a concentration of graphene solids and filtering method is also uniquely conducive to aerosol jet printing.

Thus, different ink constituents or different ink concentrations or combinations may be beneficial to formulate a graphene ink for aerosol printing versus ink jet printing. Examples of compositions of graphene-based ink, including for inkjet printing, can be found at Hersam, et al., U.S. Pat. No. 9,834,693, issued Dec. 5, 2017, Methods for Preparation of Concentrated Graphene Ink compositions and related composite materials, and Hersam et al., U.S. Pat. No. 9,902,866, issued Feb. 27, 2018, Methods for Preparation of Concentrated Graphene Ink compositions and related composite materials, which show various design parameters and variables for such inks, and are each incorporated by reference herein.

3. Circuit Formation

The composition above can be converted into inks that can be inkjet or aerosol printed with resolutions on the tens of microns without the need to use stencils or photolithography. The main constituent of these graphene-based inks are the graphene-nitrocellulose powders that are made through exfoliation and flocculation according or our previous patents and these published works. See, e.g., both incorporated by reference herein:

Secor, E. B.; Cook, A. B.; Tabor, C. E.; Hersam, M. C. Wiring up Liquid Metal: Stable and Robust Electrical Contacts Enabled by Printable Graphene Inks. *Adv. Electron. Mater.* 2018, 4 (1), 1700483.

Secor, E. B.; Gao, T. Z.; Islam, A. E.; Rao, R.; Wallace, S. G.; Zhu, J.; Putz, K. W.; Maruyama, B.; Hersam, M. C. Enhanced Conductivity, Adhesion, and Environmental Stability of Printed Graphene Inks with Nitrocellulose. *Chem. Mater.* 2017, 29 (5), 2332-2340.

It is important to note here that that the pure graphene flakes are exfoliated from graphite through a natural high-shear rotor-stator mixer (Silverson L5M-A) and screen and further crushed/ground into a power with nitrocellulose which is important to stabilizing graphene in acetone during the exfoliation process. Hence, graphene flakes are used in this printing process in lieu of graphene oxide flakes that are often obtained through the Hummer's method. Other graphene printing techniques typically use graphene oxide flakes and hence typically require additional thermal or chemical graphene oxide reduction processes to make the inks more electrically conductive. These inks can then be mixed with solvents of distinct nature for formulation into inkjet printing or aerosol printing as described in greater detail hereafter.

The printer parameters required to aerosol jet print thin and continuous graphene ink with minimal satellite droplets are also unique to this work. More particularly, sheath flow rates of 40-60 sccm, carrier flow rates of 15-45 sccm, and printing speeds of approximately 5 mm/s were tuned to yield thin and continuous traces of graphene ink with minimal satellite droplets on the substrate (see figure S1 in our attachment). Such parameters are unique to aerosol printing graphene inks as opposed to printing other materials (e.g., metal organic inks, metallic nanoparticle inks, polymer-based inks).

The printing can be used to for high-resolution printed graphene circuits for electrochemical biosensors. Others have decorated metal electrode surfaces with graphene flakes (often with drop coating from a pipette tip—which is a manually intensive process) or have printed low-resolution (>50 μm line resolution) graphene sensors for electrochemical biosensing. Again, such techniques are not high-throughput and often require a metal electrode to support the graphene.

Our graphene sensors are:
a. completely metal free (i.e., low-cost);
b. are only comprised of the carbon graphene;
c. are printed with high-resolution;
iv. can be 3D micro/nanostructured (e.g. with rapid-pulse laser annealing or salt porogens);
v. can be electrochemically active because of post-print $CO_2$ annealing;
vi. are amenable to covalent biofunctionalization with a biorecognition agent (e.g., antibody); and
vii. can be flexible and can retain their electrical conductivity and biosensing capability even after repeated bending cycles.

FIGS. 1 and 2 illustrate diagrammatically at least some of the differences between inkjet printing and aerosol jet printing.

As discussed, in one embodiment aerosol jet printing is used and can have certain benefits. Some of them are indicated in the comparison diagrams of FIGS. 1 and 2. Aerosol printing can be used with other features, including the aspects of (a) $CO_2$ thermal annealing to make the surface more electrochemically active and (b) functionalization of biorecognition agent to the added oxygen groups on the surface of the graphene from said annealing process would be independent of the graphene printing process.

But it is to be understood that techniques other than aerosol jet printing are possible which apply a graphene patter to a substrate and then take advantage of one or more of the aspects of $CO_2$ thermal annealing to make the surface more electrochemically active and functionalization of biorecognition agent to the added oxygen groups on the surface of the graphene from said annealing process would be independent of the graphene printing process. One example is inkjet printing. The ink formulation may have to be varied from that used with aerosol jet printing. For example, as indicated in FIGS. 1 and 2, at least the viscosity of the ink for inkjet printing would likely have to be varied to promote effective printing of the graphene-based ink and operation of the printer. Moreover, some of the ink constituents are different or are used in unique concentrations or combinations for aerosol printing than inkjet printing. For example, we have demonstrated that graphene-nitrocellulose powders could be formulated into inks for inkjet printing or aerosol printing (see our attached prior patents and the attached manuscript). However, to make the ink amenable to aerosol jet printing unique solvent combinations need to be used in conjunction with the graphene-nitrocellulose powders than inkjet printing. In particular we demonstrate that graphene-nitrocellulose powder was found to form a stable dispersion in 9:1 ethyl lactate:dibutyl phthalate cosolvent system and was amenable to consequent aerosol jet printing. Dibutyl phthalate has a boiling point of 340° C., so it prevents aerosol droplets from evaporating completely before deposition on the substrate. Dibutyl phthalate remains in the printed feature until subsequent baking, and its presence allows graphene nanosheets to "relax" into a flat morphology. Moreover, a graphene ink with 30 mg/mL solids loading was prepared and filtered through a 3.1 μm membrane prior to printing. Such a concentration of graphene solids and filtering method is also uniquely conducive to aerosol jet printing.

The printer parameters required to aerosol jet print thin and continuous graphene ink with minimal satellite droplets are also unique to this work. More particularly, sheath flow rates of 40-60 sccm, carrier flow rates of 15-45 sccm, and printing speeds of approximately 5 mm/s were tuned to yield thin and continuous traces of graphene ink with minimal satellite droplets on the substrate (see figure S1 in our attachment). Such parameters are unique to aerosol printing graphene inks as opposed to printing other materials (e.g., metal organic inks, metallic nanoparticle inks, polymer-based inks).

4. Additional Processing

We have also shown how you can anneal and texture these graphene circuits even on chemically or thermally sensitive substrates (polymers or paper) through rapid-pulse laser annealing and Salt Impregnated Inkjet Maskless Lithography (SIIML). See, e.g., Reference (1) and (10) in the list of references at the end of the Specific Example infra, which are incorporated by reference herein, and Hondred, et al., *Nanoscale Horiz.*, 2019, 4, 735, which is incorporated by reference herein.

5. Further Features

As mentioned, CO2 annealing process can be an important aspect. The CO2 annealing can convert an electrochemically inactive printed graphene to one that is electrochemically active to convert the graphene into an electroactive material that could be used to detect electroactive species in solution (e.g., hydrogen peroxide, dopamine, uric acid, acetaminophen).

As mentioned, the annealing also can substantially increase the amount of oxygen species on the surface of the graphene. These oxygen species are then used to covalently bind antibody to the graphene surface for subsequent electrochemical biosensing. Hence the CO2 annealing enables both electrochemical sensing (sensing of analytes in solution without a biorecognition agent immobilized on the surface) and biosensing (sensing of analytes in solution with a biorecognition agent) in solution.

C. Embodiment 2—Specific Example

An example of proof of concept follows. This is taken from Kshama Parate, Sonal V. Rangnekar, Dapeng Jing, Deyny L. Mendivelso-Perez, Shaowei Ding, Ethan B. Secor, Emily A. Smith, Jesse M. Hostetter, Mark C. Hersam, Jonathan C. Claussen, Aerosol-jet-printed graphene immunosensor for label-free cytokine monitoring in serum, ACS Appl. Mater. Interfaces 2020, 12, 7, 8592-8603, and its Supplementary Information, both of which are incorporated by reference herein in their entireties. It is to be understood this is one example of aspects of the invention.

Aerosol-Jet-Printed Graphene Immunosensor for Label-Free Cytokine Monitoring in Serum Abstract Graphene-based inks are becoming increasingly attractive for printing low-cost and flexible electrical circuits due to their high electrical conductivity, biocompatibility, and manufacturing scalability. Conventional graphene printing techniques, such as screen and inkjet printing, are limited by requirements on ink rheological properties and large as-printed line width, which impede the performance of printed biosensors. Here, we report an aerosol-jet-printed (AJP) graphene-based immunosensor capable of monitoring two distinct cytokines: interferon gamma (IFN-γ) and interleukin 10 (IL-10). Interdigitated electrodes (IDEs) with 40 μm finger widths were printed from graphene-nitrocellulose ink on a polyimide substrate. The IDEs were annealed in $CO_2$ to introduce reactive oxygen species on the graphene surface that act as chemical handles to covalently link IFN-γ and IL-10 antibodies to the graphene surfaces. The resultant AJP electrochemical immunosensors are capable of monitoring cytokines in serum with high sensitivity (IFN-γ: 0.1-5 ng/mL; IL-10: 0.1-2 ng/mL) and high selectivity (antibodies exhibited minimal cross-reactivity with each other and IL-6) without the need for sample pre-labeling or preconcentration. Moreover, these biosensors are mechanically flexible with minimal change in signal output after 250 bending cycles over a high curvature (Φ=5 mm). Hence this technology could be applied to numerous electrochemical applications that require low-cost electroactive circuits that are disposable and/or flexible.

1. Introduction

Printing nanomaterial inks to create low-cost electrical circuits holds significant promise for a wide variety of applications including medical diagnostics, food security, energy storage or energy harvesting devices, and electronic skin or electronic noses due to their ability to be fabricated by a scalable fashion on flexible substrates including those that are thermally and chemically sensitive (e.g., paper or polymers) without the need for expensive cleanroom processing.[1-9] One of the more promising materials for printed electronics is graphene, due to its high surface area, chemical stability, mechanical flexibility, and biocompatibility.[2, 10-11] Chemical vapor deposition (CVD) has been a traditional fabrication technique for graphene based devices.[12] However, this graphene synthesis process and associated techniques necessary to incorporate the resultant graphene into devices have limited the wide scale use of CVD graphene for electronic devices. For example, CVD processing has high energy costs and low yields due to the use of high-temperature and low-pressure furnace synthesis protocols. Moreover, the subsequent graphene film transfer process, needed to relocate the graphene to a more electrically and electrochemically inert substrate, is tedious and can significantly damage the graphene film.[12-13] Finally, additional patterning steps via photolithography are required to fabricate CVD graphene devices over a large area.

A more scalable method of obtaining graphene is through liquid-phase exfoliation of graphite.[14] This method produces graphene dispersions, which can consequently be formulated into graphene inks for a variety of printing applications such as screen printing and inkjet printing for large scale manufacturing.[15-16] Conventional screen printing that uses a squeegee to force ink through patterned perforations on a metal stencil typically results in low resolution circuits (100 μm line resolution or higher).[2, 15, 17] More recent advances in screen printing has realized high-resolution circuits (3.2 μm) through the use of lithographically patterned composite silicon molds.[18] However, since the fabrication of these high-resolution stencils require cleanroom processing (e.g., photolithography and reactive ion etching), they are not compatible with high-throughput, conventional screen printing instruments.

Inkjet printing is a scalable printing process compatible with roll-to-roll processing.[19] Indeed, we recently demonstrated that inkjet-printed graphene electrodes can be used for electrochemical biosensing such as hydrogen peroxide sensing and ion sensing in sweat.[10, 20] However, due to the limited spatial resolution of high-throughput inkjet printing, these biosensors have been limited to macroscale electrode designs that can be functionalized with enzymatic and ion selective membranes for subsequent amperometric or cyclic voltammetric sensing modalities. These macroscale electrode geometries are not well-suited for high-resolution impedance-based measurements often performed with interdigitated electrodes (IDEs) fabricated on the micron scale and functionalized with affinity-based biorecognition agents such as antibodies. Moreover, the favorable IDE properties such as high signal-to-noise ratio, fast response time, and reaction-diffusion kinetics improve as the IDE finger comb geometries are decreased to a scale of tens of microns.[21-23] In order to reach such high line resolution with printed electrodes, researchers have begun using various hybrid printing techniques that require pre- or post-patterning steps, such as inkjet maskless lithography, selective sintering, and transfer printing.[1, 18, 24] For example, high resolution inkjet printed patterns require an additional sacrificial layer that is used in lift-off patterning of graphene or used as a deposition adhesion promoter.[1, 16] While these techniques can produce high resolution conductive traces (20-60 μm line widths), the additional patterning steps complicate a roll-to-roll manufacturing process. Other high-resolution inkjet printing strategies rely on the fluid dynamics of the coffee-ring effect, which can create 5-10 μm wide conductive traces or sub-10-micron channel lengths between printed features, but possible device geometries are still limited by the droplet radius and drying patterns or an additional lift-off process that makes the technique less scalable than inkjet printing alone.[25-27] Therefore, a need exists to create high-resolution graphene biosensor circuits that are compatible with high-throughput manufacturing.

Aerosol jet printing (AJP) is a direct write additive manufacturing technique that eliminates the need for masks, stencils, or hybrid techniques to produce patterned circuits with high spatial resolution.[28-29] High-resolution lines with widths less than 50 μm can be achieved by AJP which consequently enables a wide variety of components in printed electronics.[30] Additionally, AJP is a more versatile printing technology as a wider range of inks can be used without the concerns of piezoelectric inkjet nozzle clogging.[31-32] Due to minimal constraints on ink properties, AJP can be used to print diverse materials, ranging from ceramics to carbon nanomaterials to organic semiconductors.[33-35] AJP also accommodates a broad number of substrates including conductors, semiconductors, dielectrics, and mechanically flexible polymers.[31] It should also be noted that AJP has been previously used to pattern graphene interconnects[28, 36] and composite AJP carbon and metallic electrodes have been applied for biosensing purposes,[37-39] but research in more complex all-graphene devices including implementation into biosensors is still lacking.

Here, we demonstrate the first aerosol-jet-printed flexible graphene IDE for electrochemical biosensing. A graphene-nitrocellulose ink is printed on a flexible polyimide film (Kapton®) in an IDE pattern by aerosolizing graphene and depositing the aerosol mist in highly focused lines. The IDEs are comprised of 50 microbands that are 40 μm in width, which is lower than previously developed inkjet-printed graphene electrodes or laser induced graphene electrodes that are not lithographically patterned.[16, 40] Prepared electrodes were thermally annealed in a $CO_2$ environment to create surface carboxyl groups on the graphene IDE that act as subsequent chemical handles for covalently linking bovine antibodies for interferon gamma (IFN-γ) and interleukin-10 (IL-10) cytokine monitoring. The rapid monitoring of both IFN-γ and IL-10 is important for a wide range of diseases as it is associated with monitoring immune system function.[41] For example, in humans a ratio of low IFN-γ/IL-10 has been associated with progression to severe mycobacterial infection which can lead to tuberculosis, HIV, and rheumatoid arthritis.[42-43] Such IFN-γ/IL-10 monitoring may also be important for early, symptom-free detection of the contagious and fatal disease in cattle called Johne's disease which infects the small intestine and is caused by *Mycobacterium avium* subspecies *paratuberculosis*.[22, 44-45] Moreover, both IFN-γ and IL-10 have been measured individually for diagnosis and prediction of disease outcomes in humans with tuberculosis, systemic meningococcal disease, and hepatitis C.[46-48]

2. Results and Discussion 2.1. Printed Biosensor Development

The first step to the fabrication of the printed biosensors was to create a graphene ink that was formulated for AJP (FIG. 3A). First, a 1:1 graphene:nitrocellulose powder was made through exfoliation and flocculation techniques that are reported in our previous work.[49-50] It is important to note here that that the pure graphene flakes are exfoliated from graphite through a natural high-shear rotor-stator mixer (Silverson L5M-A) and screen and further crushed/ground into a power with nitrocellulose which is important to stabilizing graphene in acetone during the exfoliation process. Hence, graphene flakes are used in this printing process in lieu of graphene oxide flakes that are often obtained through the Hummer's method. Other graphene printing techniques typically use graphene oxide flakes and hence typically require additional thermal or chemical graphene oxide reduction processes to make the inks more electrically conductive.[1, 10, 51-52] In addition, nitrocellulose decomposes into a highly conductive residue after heat treatment, making it a value-added surfactant.[53] The graphene-nitrocellulose powder was found to form a stable dispersion in 9:1 ethyl lactate:dibutyl phthalate cosolvent system. Dibutyl phthalate has a boiling point of 340° C., so it prevents aerosol droplets from evaporating completely before deposition on the substrate. Dibutyl phthalate remains in the printed feature until subsequent baking, and its presence allows graphene nanosheets to "relax" into a flat morphology.

A graphene ink with 30 mg/mL solids loading was prepared and filtered through a 3.1 μm membrane prior to printing. A 2 mL aliquot of the graphene ink was pipetted into the ink vial of the printer and ultrasonically atomized. The fluid dynamics of the aerosol jet deposition process is shown in FIG. 3B. Aerosolized ink droplets are carried by a nitrogen gas flow towards the deposition nozzle. Before deposition, the carrier gas flow is met by a second nitrogen stream at a higher flow rate, which forms a focusing sheath around the aerosol particles in the carrier stream. The highly focused aerosol droplets, which contain graphene, are then deposited on the substrate below the nozzle. Sheath flow rates of 40-60 sccm, carrier flow rates of 15-45 sccm, and printing speeds of approximately 5 mm/s were tuned to yield thin and continuous traces of graphene ink with minimal satellite droplets on the substrate (FIGS. 9A-F).

Graphene-based IDEs were printed on a flexible polyimide film (FIG. 4A). The devices are designed to maximize sensing surface area, which increases the sensitivity of the device, while decreasing the channel length (or interfinger spacing) to minimize electrochemical resistance. The electrode design has a finger width of 40 μm, a finger spacing of 100 μm, and 50 fingers, for a total IDE active surface area of 14 $mm^2$. Such 40 μm line resolution is lower than previous direct-write graphene printing processes such as inkjet printing (~60 μm line resolution)[16] or direct-write graphene synthesis processes such as creating laser induced graphene from polyimide (~75 μm line resolution).[40] The ability to create smaller IDE finger widths has generally been shown to be improve the signal-to-noise ratio of the electrodes during electrochemical impedance spectroscopy—the sensing modality used herein to perform the electrochemical cytokine biosensing.[1] The active surface area is defined as the total surface area of printed fingers (finger width×finger length×number of fingers), as these features pose the smallest spacing between electrodes and are dominantly active in subsequent electrochemical measurements. The IDEs were then heat treated in a tube furnace at 350° C. for 30 min to remove trapped solvent and drive decomposition of the nitrocellulose into a conductive $sp^2$ carbon residue.[53]

2.2. Microscopy and Spectroscopy Characterization 2.2.1. Microscopy Characterization The film morphology and chemical composition of the heat-treated graphene IDEs were subsequently characterized with confocal laser microscopy, scanning electron microscopy (SEM), atomic force microscopy (AFM), x-ray photoelectron spectroscopy (XPS), and Raman spectroscopy. While the thermal decomposition of nitrocellulose can lead to a porous film under some conditions (FIGS. 10A-D), SEM images (FIGS. 4A and B) reveal that the graphene nanosheets are well-aligned in a dense and continuous film in the optimized devices. Coupled with the low film porosity, this degree of flake stacking suggests that the carboxyl functionalization of graphene is mostly limited to the top surfaces of the film, allowing for $sp^2$-rich content in the bulk of the film and thus high electrical conductivity ($1\times10^4$-$7\times10^4$ S/m). This conductivity measurement is similar to the conductivity that we obtained previously with blade coated graphene-nitrocellulose ink ($4\times10^4$ S/m),[53] inkjet printed graphene-ethyl cellulose ink ($2.5\times10^4$ S/m),[16] and screen printed graphene-ethyl cellulose ink ($1.9\times10^4$ S/m).[2] It should be noted that Majee et al acquired a higher conductivity ($4\times10^4$ S/m) with inkjet printed graphene that also contained ethyl cellulose but in this case a higher concentration of graphene (50 mg/mL initial solid loading) was used in the ink formulation.[54]

Next, a bare section of as-received Kapton® was scanned at the highest resolution objective of the Olympus confocal laser microscope (50× magnification with 200 nm lateral resolution and 6 nm vertical resolution). The optical image (FIG. 11A) shows spots and scratches, but the 3D scan of the film height (FIG. 4D) shows additional topography. A roughness measurement of the dashed box region in FIG. 4D (see inset) yields a root mean square roughness of 37 nm. The printed graphene line can barely be distinguished from the Kapton® film using confocal laser microscopy (FIG. 11E), therefore, AFM was used to measure printed graphene film thickness after heat treatment (FIGS. 4E and F). Note that the underlying polyimide substrate is wavy and rough, with a root mean square roughness of approximately 40 nm, resulting in AFM scans that appear to have depressed regions in the middle of a printed line (FIGS. 11A-F). To reasonably measure film thickness, an AFM scanned region with relatively flat Kapton® surface was analyzed. The film thickness was averaged over the boxed region in FIG. 4E and found to be 25 nm. This film thickness is several orders of magnitude thinner as compared to screen printed or inkjet printed devices that can have a thickness of approximately several microns or hundreds of nanometers respectively. Hence such thin AJP printed films translates into lower material consumption (Table S1) for manufacturing the devices.[2, 16]

2.2.2. Spectral Characterization

XPS and Raman spectroscopy were next performed to characterize the material properties of the AJP graphene before and after the $CO_2$ annealing process. Before $CO_2$ annealing, the graphene IDE consists of $sp^2$ and $sp^3$ hybridized carbon as denoted by the peak at 284.5 eV and carboxyl groups (—COOH) denoted by the peak at 288.5 eV, which contributes only 5% of all the functional groups available on the graphene IDE (FIG. 5A). After the $CO_2$ annealing, the development of complex surface chemistry appears (FIG. 5B), including carbide bonds (283.7 eV) and C—C single bonds (285.1 eV) in addition to oxygenated species (i.e., carboxyl (COOH) group peak at 289.2 eV and a carbonyl group ($R_2C=O$) peak at 287.2 eV) that demonstrate the chemical functionalization of the graphene. The carboxyl and carbonyl groups contribute to 15% of all the functional groups on the surface of the IDE leading to an increase of 10% of the oxygen-rich groups. These carboxyl and carbonyl groups are essential for further chemical reactions with EDC/NHS that enables covalent binding of the desired antibody with the graphene IDEs.

Next, Raman spectroscopy measurements were performed on the samples before and after annealing with $CO_2$ in order to characterize the graphitic character of the samples (FIG. 5C). The Raman spectra of the samples exhibit the characteristic bands of graphitic materials including the D band (~1353 cm$^{-1}$) that is indicative of defects, the G band (~1584 cm$^{-1}$), and the 2D band (~2702 cm$^{-1}$) that originates from second order zone-boundary phonons.[55-57] The intensity ratio $I_D/I_G$ is used as a measure of defect level in graphite-based materials,[14, 58] and the corresponding values were determined to be 0.49±0.02 and 0.48±0.01 for the sample before and after $CO_2$ annealing, respectively, which suggests that the $CO_2$ annealing does not induce significant physical defects or cause material removal (FIG. 13A-B) in the samples. The calculated $I_{2D}/I_G$ ratios for unprocessed and processed samples are 0.34±0.02 and 0.36±0.01, respectively, suggesting that the graphitic character of the electrodes is not significantly affected by the $CO_2$ annealing process.[59]

2.3. Electrical and Electrochemical Characterization

The electrical and electrochemical performance of the graphene IDEs was next characterized to assess the potential of the printed graphene IDEs for biosensing. First, it is demonstrated that AJP can be used to print features with sub-micron thickness. As printed graphene films are known to be percolating networks,[28, 60] the relationship between printed film morphology and film conductivity was investigated for aerosol-jet-printed graphene lines with sub-micron thickness. The printing speed and number of printing passes are two straightforward ways to control the thickness and width of printed lines. First, lines were patterned on a Kapton® substrate at various printing speeds. Both line thickness and line width are a function of printing time (units of s/mm), which is the inverse of printing speed (mm/s) (FIG. 6A). Line thickness, in particular, varies linearly with printing time. Lines of various thicknesses were also achieved using 1 to 30 printing passes.

Figure 10B:
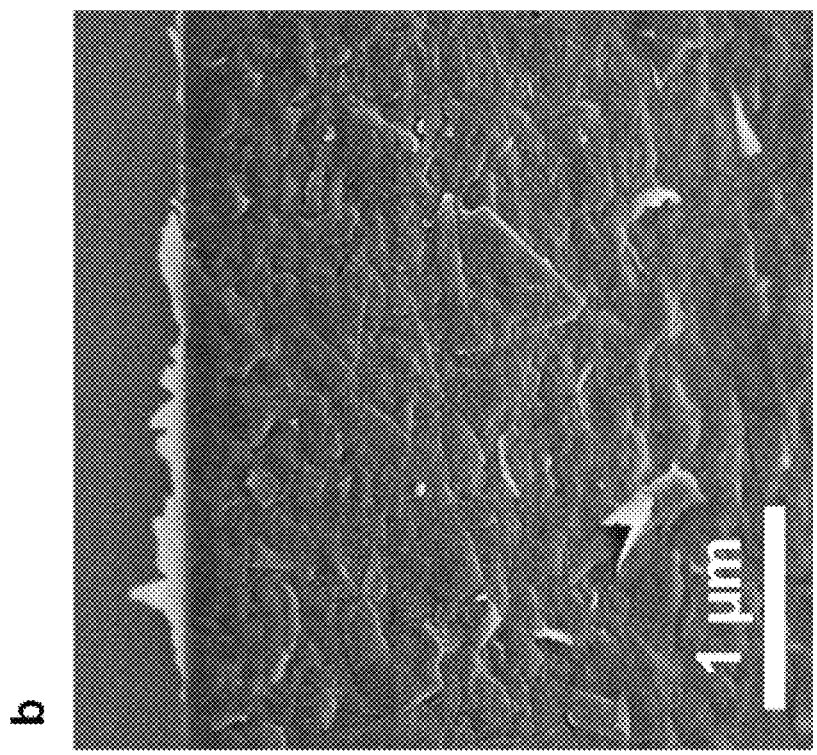
Figure 10A:
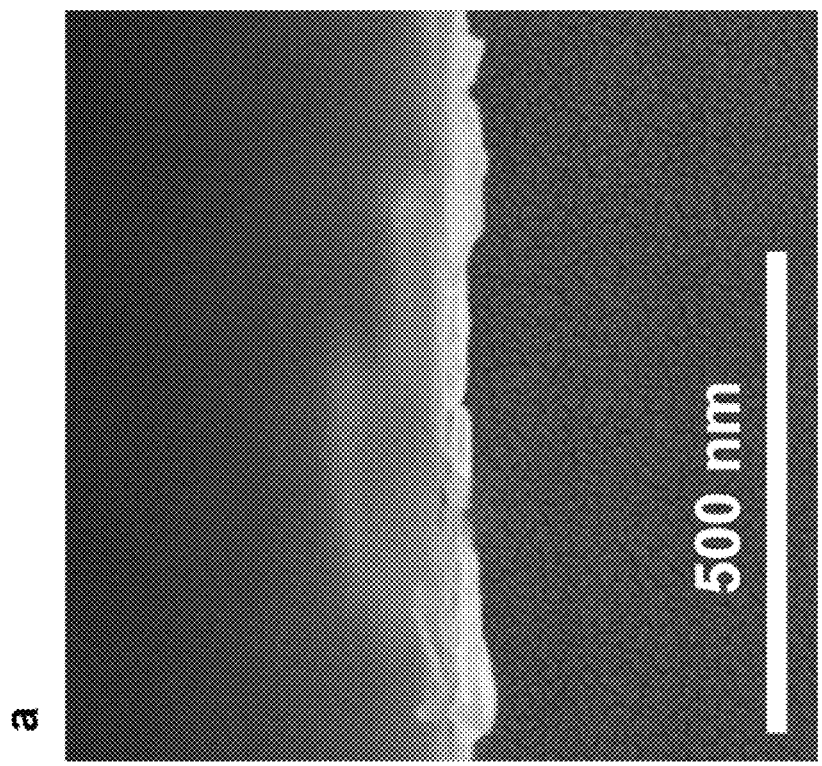
Figure 10D:
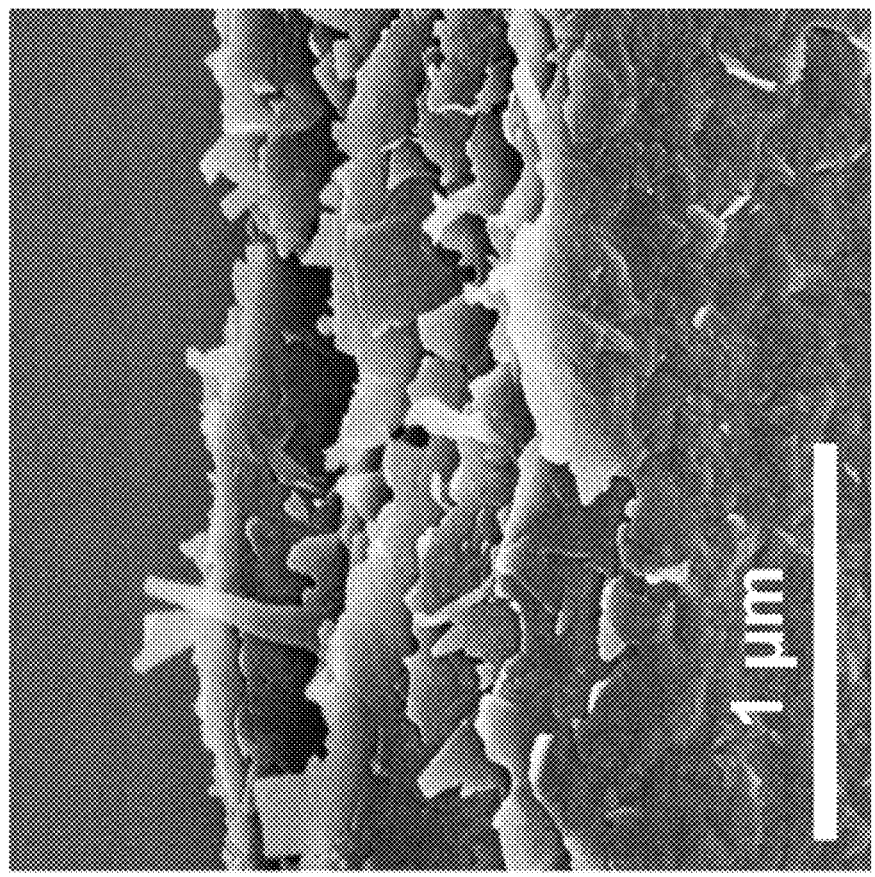
Figure 10C:
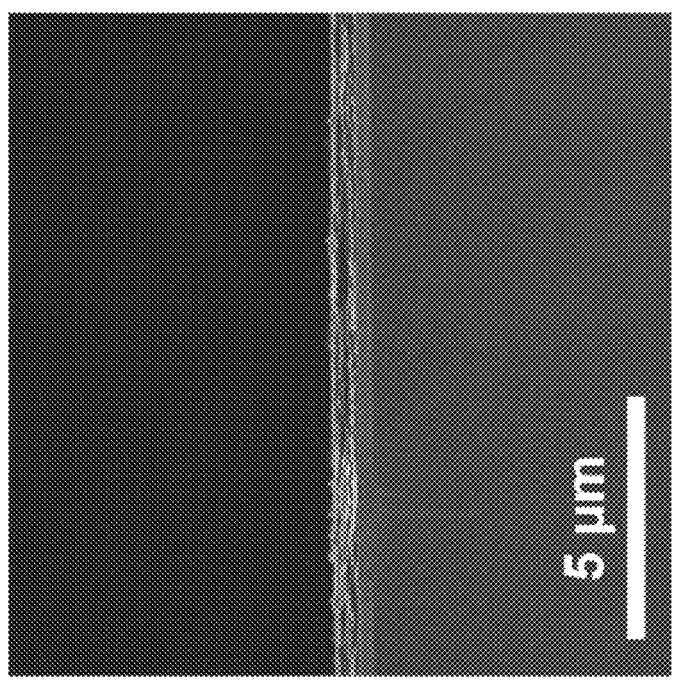

The conductivities of these lines were investigated as a function of film thickness (FIG. 6B). Graphene line conductivity increases with film thickness until approximately 200 nm thickness, after which the conductivity declines. This behavior can be explained by investigating the film morphology of graphene lines with different thicknesses. As shown by SEM analysis, thin (<100 nm thick) printed lines show a percolating, non-porous microstructure (FIGS. 10A and B) while thicker films (~1 μm thick) are more porous (FIGS. 10C and D). This porosity likely emerges during the heat treatment step, as the pyrolysis of nitrocellulose evolves gases which creates an open microstructure. The porosity is not accounted for when calculating the cross-sectional area of the printed line, which causes the calculated conductivity to be less than the true value. Furthermore, the porous regions in thicker films may have poorer intersheet contacts, which contribute to lower conductivity despite the amorphous carbon residues. Thus, the use of nitrocellulose in the ink formulation may explain why the conductivity of printed graphene lines does not match percolation theory as shown by other studies (Jabari et al).[28] This trend is observed for graphene lines printed on $SiO_2$ as well as Kapton®, indicating that substrate roughness does not influence the film conductivity (FIG. 12). This result informed our decision to print IDEs with a single pass, as to form thin films with negligible porosity.

After printing and baking, the graphene IDEs were subjected to a preliminary electrical quality test. A multimeter was used to check the IDEs for low resistance (<10 kΩ) over one side of the ~2 cm long electrode and for shorting pathways between the two electrodes of a single device. Devices passing this screening test were used in subsequent electrochemical experiments. Additionally, transmission line measurements were used to calculate the resistivity of graphene fingers/lines that were printed at the same conditions as the IDEs. The electrical resistance of the graphene lines scales linearly with channel length up to 4 mm, and the resistivity is calculated to be in the range of $1.4 \times 10^{-5}$-$10^{-4}$ Ω-m (FIG. 6C), or an electrical conductivity in the range of $1 \times 10^4$-$7 \times 10^4$ S/m. These results compare favorably with other graphene printed devices.[28, 53] The millimeter-scale high conductivity indicates that the graphene nanosheets and amorphous carbon residue form a well-connected matrix over electronically-large distances. Further improvements in conductivity are possible when the graphene electrode thickness is increased above 100 nm,[28] but limiting the thickness to 25 nm consumes less material and minimizes printing time without compromising biosensor performance (Tables S1, S2 and S3).

The $CO_2$ annealing process was used to improve the electroactive nature of the printed graphene IDEs from a negligible response to one that is electrochemically active. As mentioned previously, XPS results (FIGS. 5A-C) showed that the graphene surface is becoming richer in oxygenated species (carboxyl and carbonyl groups) following $CO_2$ annealing, although the overall defect density remains low. The π-electron cloud on the carboxyl and carbonyl groups helps in the heterogeneous electron transfer between the electrode and the redox probe, thus the electrocatalytic nature of the electrodes was improved by performing this $CO_2$ annealing process.[61] The electrochemical characterization of the graphene IDE was performed by both cyclic voltammetry (CV) and electrochemical impedance spectroscopy (EIS) to determine its heterogeneous electron transfer capability. The CV was performed at a scan rate of 5, 10, 25, 50 and 100 mV/s in 5 mM ferro/ferricyanide probe. As noted in FIG. 6D, the graphene IDE before $CO_2$ annealing does not show an electrochemical response at the scan rate of 100 mV/s, since the CV displays near zero heterogeneous electron transfer due in part to a most likely lack of sufficient edge plane defects.[62] However, after $CO_2$ annealing, current peaks appear on the CV. The occurrence of these peak currents ($i_p$) with a large separation between them (ranging from $\Delta E_p$=0.57 V to 1.24 V) demonstrates heterogeneous electron transfer kinetics, which is typical of a multilayer graphene surface functionalized with oxygen groups that has low density of either edge or basal plane defects; this was also demonstrated by Ambrosi et al and Pope et al, who observed a peak-to-peak voltage separation ranging between approximately 0.5 and 1.1 V.[63-64] The effective electrochemical surface area was calculated using Randles-Ševćik equation (FIGS. 14A-B) as 8.4 mm². This surface area contributes to a total active sites of 60% w.r.t. the geometric area of the AJP graphene IDE, which is larger than our previously reported work for vertically aligned CNT electrodes.[21] Hence, the $CO_2$ annealing process significantly improves the electroactive nature of the AJP IDE which is important to subsequent electrochemical EIS measurements.

EIS characterization was next performed between a frequency range of 0.1 Hz-100 kHz at a voltage amplitude of 10 mV in 5 mM ferro/ferricyanide probe. In a Nyquist plot, the high frequency semi-circular region represents the resistance of electron transfer kinetics ($R_{ct}$) between the redox probe and the electrode surface, corresponding to the diameter of the semi-circle. From FIG. 6E, the Nyquist plot preceding $CO_2$ annealing appears as scattered points, which do not convey any information about the electrochemical properties of the IDE surface. However, after $CO_2$ annealing, the data form a quantifiable semi-circular Nyquist plot (FIG. 6F). This can be attributed to the introduction of higher amount of oxygen functional groups on the IDE as opposed to the previously low functional group density on the surface, which allows for an ease of exchange of electrons between graphene and the redox probe. Moreover, this system lacks a mass transfer region and features a large charge transfer resistance, $R_{ct}$~20 kΩ (FIG. 6F). These electron transfer kinetics are characteristic of a thin film of highly oriented pyrolytic graphite (HOPG) stacking of graphene, which suggests that the $CO_2$ annealed film consists of mostly basal planes of graphene underneath the functionalized top surface.[65]

2.4. Immunosensing of IFN-γ and IL-10

The IDE was functionalized with anti-bovine (IFN-γ or IL-10) antibody (FIGS. 3C and D) for sensing the respective antigens (IFN-γ or IL-10). To avoid non-specific binding of the antigen with the area of electrode unoccupied by the antibody, various blocking agents were tested for false positive signal of the biosensor. First, the efficacy of bovine serum albumin (BSA) as a blocking agent was evaluated at various concentrations (0%, 0.5%, 1%, 2%) (FIGS. 15A-D). However, BSA alone does not prevent nonspecific binding of the antigen. Ultimately, the blocking agent utilized in sensitivity studies of the biosensor was a mixture of 1% BSA, 0.1% tween-20, and 0.1% fish gelatin, which forms a large-chain protein that more extensively covers the bare electrode surface.[66]

The immunosensing performance of the graphene IDE platform was evaluated in real biological matrix (bovine implant serum, see experimental section) to determine its feasibility for early disease detection in the presence of other proteins. First, the biofunctionalized graphene IDE was incubated with increasing concentration of the respective antigen (IFN-γ or IL-10) prepared in a bovine serum implant. Next, EIS measurements were recorded for each concentration of the antigen added. With every increase in the antigen concentration, the diameter of the Nyquist plot increases, which corresponds to the charge transfer resistance ($R_{ct}$) between the redox probe and electrode. As the antigen concentration increases, more antigen and antibody bind to form an insulating barrier for the electron transfer across the redox probe and electrode, leading to an increased $R_{ct}$.[67] Normalized charge transfer resistance is plotted against the concentration of antigen in FIGS. 7A and B. A linear sensing range was obtained by selecting the region of increasing $R_{ct}$ that can be linearly fit with the largest $R^2$ value. The detection limit was calculated using the regression line equation and considering 3 times the standard deviation of the background signal (i.e., 3σ). It was found that the linear sensing range for IFN-γ and IL-10 was 0.1-5 ng/mL and 0.1-2 ng/mL, respectively, with a detection limit of 25 pg/mL and 46 pg/mL, respectively (sensitivity of the IDE for IFN-γ and IL-10 was 44.9% per decade and 36.4% per decade, respectively). These sensing ranges cover the lower concentration ranges of IFN-γ detectable in clinical disease stage and fit in the newly infected to clinical disease stage (for IL-10) of Johne's disease.[44] In addition, these sensing ranges are biomedically relevant, for example, in the case of pulmonary tuberculosis in humans the mean concentration of IL-10 is 56 pg/mL, IFN-γ is 877 pg/mL whereas in the case of paratuberculosis in cattle the mean concentration of IFN-γ is 5 ng/mL and IL-10 is 8 ng/mL.[44, 46, 68] As this developed sensor is more sensitive than the latter example, an acquired bovine sample can be easily diluted to acquire the data and the results can be extrapolated to determine the actual concentration of the cytokines.

Each graphene IDE immunosensor platform was also tested for cross-reactivity with similar antigens (i.e., IFN-γ, IL-10, and interleukin-6 (IL-6)). IFN-γ and IL-10 are similar in structure[69], whereas IL-10 and IL-6 are similar in functionality[70]—making them susceptible for cross-reacting with IL-10 or IFN-γ antibodies. Therefore, the immunosensor functionalized with IFN-γ antibody was examined for interference with increasing concentration of IL-10 and IL-6 and similarly, the immunosensor functionalized with IL-10 antibody was examined for interference with increasing concentration of IFN-γ and IL-6 as shown in FIGS. 7C and D). In both cases, the percent change in $R_{ct}$ is within 20%, which can be considered as the background signal since the change in $R_{ct}$ is much larger for the same concentration of target antigen. Importantly, the signal shows no clear dependence on the concentration of the interfering antigen, while a much higher change in the signal (~100%) is observed when the appropriate antigen is used. Overall, these results show that the AJP graphene biosensor possesses high selectivity for the immobilized antibody.

2.5. Mechanical Flexibility Measurements

The mechanical flexibility of the IDE was examined by measuring electrical and electrochemical impedance characteristics of a functionalized IDE as a function of bending cycles, so that it could be implemented in a wearable or implantable format such as would be the case in a small subcutaneous bovine implant.[71] First, the fabricated graphene IDE was mounted on a strip of polyethylene terephthalate (PET) and bent around rods of various diameters (3.18 mm, 7.19 mm and 11.08 mm). The substrate thickness was measured as 0.25 mm, producing a strain (=thickness of substrate/bending diameter) of 0.079, 0.035 and 0.022 respectively. The electrical resistance of the IDE was measured before and after bending (10, 20, 50, 100, 200, 500 and 1000 cycles). The fractional change in electrical resistance as a function of bending cycles plotted (FIG. 8B) reveals that the change in electrical resistance is almost negligible (<1%) and therefore, the electrical characteristics of the device is independent of mechanical flexing cycles.

Next, an IL-10 antibody biofunctionalized graphene IDE was incubated with 10 ng/mL of IL-10 antigen and mounted on a PET strip using double-sided adhesive tape. The total thickness of the graphene IDE on PET assembly was 0.31 mm. The biosensor was flexed around a rod suspended within a 3D-printed trough (Formlabs form 2, 3D printer) so that the biosensor could remain in contact with a layer of buffer solution (phosphate buffer solution (PBS)) throughout the duration of the experiments to eliminate antibody denaturing due to a dry sensor (FIG. 8A). A rod (dia.=5 mm) resulting in sensor bending strain of 0.062, was utilized while the electrochemical signal was recorded following every 50 bending cycles (a total of 250 bending cycles were performed). The percentage change in sensor $R_{ct}$ values (derived from the Nyquist plot as shown in FIG. 16) of the functionalized biosensor is approximately only 6% for the bending experiments performed with the 5 mm rod, showing robustness of the biosensor when bent severely (FIG. 8C). This indicates that this biosensor platform is suitable for use on curvilinear work surfaces.

3. Conclusions

In conclusion, this work demonstrated the first use of aerosol jet printed graphene for biosensing by developing printed interdigitated electrodes with a graphene-nitrocellulose ink. Printed graphene lines demonstrated high electrical conductivity (~$10^4$ S/m) at low thickness (~25 nm) and millimeter-scale portions of the film. The top surface of the graphene electrode was functionalized with oxygen-containing groups by annealing in $CO_2$ environment while preserving the highly oriented graphitic structure underneath. Graphene biosensors were functionalized with IFN-γ and IL-10 bovine antibodies through EDC and NHS chemistry, and were tested in a real biological matrix (bovine minced implant supernatant). These biosensors were able to monitor both IFN-γ and IL-10 in bovine implant serum across a wide linear sensing range (0.1-5 ng/mL and 0.1-2 ng/mL) with a low detection limit (25 pg/mL and 46 pg/mL) and rapid response time (33 minutes) without the need for pre-concentration or labeling steps. Moreover, the biosensor was highly selective towards IFN-γ or IL-10 with negligible cross-reactivity with each other and similar cytokines (i.e., IL-6). Hence this developed biosensors are well-suited for rapid, in-field testing. The developed AJP graphene immunosensors have achieved the best limit of detection and selectivity for an immunosensor that does not require pre-labeling or pre-concentration and that can monitor both bovine IL-10 and IFN-gamma. Moreover, the developed AJP printed graphene immunosensor and overcomes the complexity of laboratory-based multi-cytokine testing that utilize fluorescently labeled beads/surfaces functionalized with antibodies commonly associated with Luminex xMAP,[72] fluorescence-enhancing microarrays on plasmonic gold films,[73] and flow cytometric multiplex and enzyme-linked immunosorbent assays[74] as well as circumvents the need to perform lithographic patterning and electroplating associated with more conventional in-field electrochemical immunosensors created with gold electrodes patterned on printed circuit boards.[75] Important to this work, the developed biosensors detects the biomarkers in the sensing range (0.1-10 ng/mL) that is appropriate for the bovine disease paratuberculosis. Such rapid monitoring of these cytokines is clinically important to improve the accuracy of a potential screening test for early-stage detection of diseases, such as Johne's disease in cattle or tuberculosis in humans. By minimizing transportation time, sample storage and handling challenges, and sample degradation, this point-of-care diagnostic sensor will help establish faster and more accurate treatment solutions for the patient, whilst minimizing errors.

In a broader sense the aerosol printed graphene electrode created herein could be utilized in a wide variety of applications. The readily functionalized graphene surface and the universality of the antibody functionalization protocol enables sensing of desired analytes without the need of any sample pre-treatment. In this context, the developed immunosensor platform could be applied to different sensing paradigms beyond measuring cytokines such as proteins, bacteria and viruses for early detection of fatal human diseases like systemic meningococcal disease[48], cancer[76], HIV[77] or also for detection of food pathogens such as *E. coli*.[78] Additionally, aerosol printing of thin film graphene IDEs is amenable to high-throughput manufacturing as both graphene exfoliation and printing are scalable process and are also more suited to graphene recycling as opposed to high-temperature graphene growth process through chemical vapor deposition which generally require cleanroom technology and results in low yields of graphene that are challenging to transfer to substrates that are suitable for device applications.[14, 79] Finally, the electrochemical sensitivity and flexibility of the graphene circuits make them potentially well-suited for a wide variety of applications including the creation of electrochemical supercapacitors, biofuel/microbial fuel cells, and wearable biosensors.[80-89] In fact such flexible graphene circuits have been shown to be useful for a wide array of sensor applications including bacteria sensing on tooth enamel, heavy metal detection via skin integrated sensors, ions and protein monitoring in sweat, as well as in solar cells, organic light-emitting diodes, and strain sensors.[89-95]

4. Experimental Section

All chemicals and reagents were of analytical grade and handled according to their materials safety data sheet. Graphite powder at grade 3061 was purchased from Asbury Graphite Mills (Asbury, NJ, USA). Nitrocellulose (NC), damped with isopropanol, was purchased from Scientific Polymer (Ontario, NY, USA). All solvents were purchased from Millipore Sigma (Saint Louis, MO, USA). N-(3-Dimethylaminopropyl)-N'-ethylcarbodiimide (EDC), N-hydroxy succinimide (NHS), ethanolamine, tween-20, gelatin from cold water fish skin, and potassium hexacyanoferrate (II) trihydrate were purchased from Sigma-Aldrich (Saint Louis, MO, USA). Potassium ferricyanide was purchased from Fisher Scientific (Fair Lawn, NJ, USA). 2-(N-morpholino) ethanesulfonic acid (MES buffer) was purchased from Alfa Aesar (Ward Hill, MA, USA). Bovine serum albumin (BSA) was purchased from VWR International, LLC (Solon, OH, USA). Recombinant bovine interferon gamma (IFN-γ) (Cat. No. PBP001), recombinant bovine interleukin-10 (IL-10) (Cat. No. PBP016A), mouse anti-bovine interferon gamma (anti IFN-γ) (mAb. Cat. No. MCA1783), and mouse anti-bovine interleukin-10 (anti IL-10) (mAb, Cat. No. MCA2110) were purchased from Bio-rad Laboratories Inc (Hercules, CA, USA). All solutions were prepared in phosphate buffered saline (1×PBS) buffer.

Bovine implant was acquired by a stainless-steel implant device with a window that is placed in the subcutis of the cattle. A collagen plug is extracted from the subcutis, surrounded by a nylon mesh with a pore size of 30 μm. The extracted bovine implant is minced and centrifuged at 1000 rpm for 30 mins. The collected supernatant is diluted (1:1000) and further used for sensing IFN-γ and IL-10.

Graphene-Nitrocellulose Powder and Ink Preparation:

Graphene-nitrocellulose powder was prepared as in our previous work.[53] Briefly, a 1:1 mixture of graphite powder and nitrocellulose in acetone was exfoliated via shear mixing for 4 hours at 10,230 rpm. The product was centrifuged in two steps, 5000 rpm for 15 min and 6000 rpm for 20 min, and the resultant supernatant was collected. The graphene-nitrocellulose supernatant was flocculated with NaCl and centrifuged to form a pellet. The pellet was washed with DI water and then collected on a membrane using vacuum filtration. The product was collected, dried, and crushed with a mortar and pestle into a fine powder. This graphene-nitrocellulose powder was then dispersed via bath ultrasonication in a 1:9 v/v mixture of dibutyl phthalate and ethyl lactate, for a total solid loading of 30 mg/mL. The total sonication time was 6 hours.

Aerosol Jet Printing of Interdigitated Electrodes:

The graphene-nitrocellulose ink was aerosol jet printed (Optomec, AJ 200) to form IDE patterns on a Kapton® substrate that was heated to 60° C. in air during printing. Sheath flow rates were in the range of 40-60 sccm, and carrier flow rates were in the range of 15-45 sccm. Printing speed was maintained at 5 mm/s. After printing, the devices were heat treated in a tube furnace (Thermo Scientific, Lindberg Blue M) at 350° C. in air at atmospheric pressure for 30 min to decompose nitrocellulose into a conductive carbon residue.[53]

Biofunctionalization of Graphene IDE:

The printed graphene IDE was annealed in a $CO_2$ environment at 400° C. for 2 hours in an OTF-1200X tube furnace (MTI Corporation, Richmond, CA, USA) to increase the quantity of surface carboxyl functional groups on the graphene. Next, the IDE was functionalized using 0.4 M EDC and 0.1 M NHS in 0.1 M MES buffer for 1 hour at room temperature, followed by an overnight incubation in either (1:50) mouse anti bovine IFN-γ or IL-10 solution. The unreacted EDC/NHS on the graphene IDE was quenched using 1 M ethanolamine for 20 min and the exposed, unfunctionalized portion of the IDE surface was blocked using a mixture of 0.1% tween-20, 0.1% fish gelatin, and 1% BSA for 1 hour in an effort to prevent non-specific adsorption of non-target analytes.[66] Before subsequent biosensing experiments, a baseline electrochemical impedance spectrum was acquired over the frequency range of 0.1 Hz-100 kHz with a voltage amplitude of 10 mV using a 5 mM ferro/ferricyanide (1:1) redox probe. Next, the graphene IDE was incubated with a 100 μl of test solution containing IFN-γ or IL-10 (prepared in bovine minced implant serum) for 30 min to allow the IFN-γ or IL-10 to bind to the immobilized antibody on the graphene IDE surface. After a baseline EIS measurement was obtained, calibration plots were obtained by measuring the $R_{ct}$ for successively increasing concentrations of IFN-γ or IL-10 target analyte.

Confocal Laser Microscopy:

Three-dimensional height profiles of printed graphene lines were obtained via confocal laser microscopy using an Olympus OLS5000 laser confocal microscope. Data was collected at the 50× objective, which enables a lateral resolution of 200 nm and a vertical resolution of 6 nm. All data analysis was performed in the Olympus software.

Atomic Force Microscopy:

Thickness measurements of the printed graphene IDE was performed using noncontact mode atomic force microscopy (Asylum Research Cypher AFM). The graphene IDEs were printed on Kapton® for AFM measurements.

Scanning Electron Microscopy:

SEM images of the printed graphene IDEs were obtained using a LEO Gemini 1525 SEM and Hitachi SU8030 SEM. A 10 nm layer of osmium was coated on as printed samples to prevent charging effects with the nonconductive Kapton®.

X-Ray Photoelectron Spectroscopy:

The XPS measurements were performed using a Kratos Amicus/ESCA 3400 instrument. The sample was irradiated with 240 W unmonochromated Al Kα x-rays, and photoelectrons emitted at 0° from the surface normal were energy analyzed using a DuPont type analyzer. The pass energy was set at 150 eV, and a Shirley baseline was removed from all reported spectra. CasaXPS was used to process raw data files.

Raman Spectroscopy:

Raman spectroscopy measurements were performed using an XploRa Plus confocal Raman upright microscope, equipped with a 785-nm laser excitation source (5 mW at the sample) and a Synapse EMCCD camera (Horiba Scientific/ JY, France). A 100× air objective (Olympus, LMPlanFL) with a 0.9 numerical aperture was used to collect Raman signal under ambient laboratory conditions. The spectra were collected from 1000 to 3300 $cm^{-1}$ with a 600 grooves/ mm grating. Reported spectra were an average of 3 measurements, with a 30 s acquisition time for each spectrum.

All data were processed using Igor Pro 6.37 scientific analysis and graphing software (Wavemetrics, Lake Oswego, OR, USA). The spectra were fitted to a Gaussian function with a linear baseline using the multi-fit peak function in order to extract peak intensity (height).

Associated Content

Supporting Information

Supporting Information is available on the ACS publication website or from the author.

Demonstration of tunable film thickness with printing parameters, SEM images to demonstrate influence of printed graphene porosity on electrical properties, printed graphene film thickness characterization on Kapton® using confocal laser microscopy, analysis of material consumption during printing with a table comparing printed line properties, optimization of blocking agent for biofunctionalization of graphene IDE.

References for Supporting Information for Embodiment 2

(1) Hondred, J. A.; Stromberg, L. R.; Mosher, C. L.; Claussen, J. C. High-Resolution Graphene Films for Electrochemical Sensing Via Inkjet Maskless Lithography. *ACS nano* 2017, 11 (10), 9836-9845.

(2) Hyun, W. J.; Secor, E. B.; Hersam, M. C.; Frisbie, C. D.; Francis, L. F. High-Resolution Patterning of Graphene by Screen Printing with a Silicon Stencil for Highly Flexible Printed Electronics. *Adv. Mater.* 2015, 27 (1), 109-15, DOI: 10.1002/adma.201404133.

(3) Bandodkar, A. J.; Jeerapan, I.; You, J.-M.; Nuñez-Flores, R.; Wang, J. Highly Stretchable Fully-Printed Cnt-Based Electrochemical Sensors and Biofuel Cells: Combining Intrinsic and Design-Induced Stretchability. *Nano Lett.* 2015, 16 (1), 721-727.

(4) Chen, B.; Kruse, M.; Xu, B.; Tutika, R.; Zheng, W.; Bartlett, M. D.; Wu, Y.; Claussen, J. C. Flexible Thermoelectric Generators with Inkjet-Printed Bismuth Telluride Nanowires and Liquid Metal Contacts. *Nanoscale* 2019, 11 (12), 5222-5230.

(5) Honda, W.; Harada, S.; Arie, T.; Akita, S.; Takei, K. Wearable, Human-Interactive, Health-Monitoring, Wireless Devices Fabricated by Macroscale Printing Techniques. *Adv. Funct. Mater.* 2014, 24 (22), 3299-3304.

(6) Lorwongtragool, P.; Sowade, E.; Watthanawisuth, N.; Baumann, R.; Kerdcharoen, T. A Novel Wearable Electronic Nose for Healthcare Based on Flexible Printed Chemical Sensor Array. *Sensors* 2014, 14 (10), 19700-19712.

(7) Núñez, C. G.; Manjakkal, L.; Dahiya, R. Energy Autonomous Electronic Skin. *npj Flexible Electron.* 2019, 3 (1), 1-24.

(8) Sundriyal, P.; Bhattacharya, S. Inkjet-Printed Electrodes on A4 Paper Substrates for Low-Cost, Disposable, and Flexible Asymmetric Supercapacitors. *ACS Appl. Mater. Interfaces* 2017, 9 (44), 38507-38521.

(9) Zhang, C. J.; McKeon, L.; Kremer, M. P.; Park, S.-H.; Ronan, O.; Seral-Ascaso, A.; Barwich, S.; Coileáin, C. Ó.; McEvoy, N.; Nerl, H. C. Additive-Free Mxene Inks and Direct Printing of Micro-Supercapacitors. *Nat. Commun.* 2019, 10 (1), 1795.

(10) Das, S. R.; Nian, Q.; Cargill, A. A.; Hondred, J. A.; Ding, S.; Saei, M.; Cheng, G. J.; Claussen, J. C. 3d Nanostructured Inkjet Printed Graphene Via Uv-Pulsed Laser Irradiation Enables Paper-Based Electronics and Electrochemical Devices. *Nanoscale* 2016, 8 (35), 15870-15879.

(11) Huang, L.; Huang, Y.; Liang, J.; Wan, X.; Chen, Y. Graphene-Based Conducting Inks for Direct Inkjet Printing of Flexible Conductive Patterns and Their Applications in Electric Circuits and Chemical Sensors. *Nano Res.* 2011, 4 (7), 675-684, DOI: 10.1007/s12274-011-0123-z.

(12) Yu, H. K.; Balasubramanian, K.; Kim, K.; Lee, J.-L.; Maiti, M.; Ropers, C.; Krieg, J.; Kern, K.; Wodtke, A. M. Chemical Vapor Deposition of Graphene on a "Peeled-Off" Epitaxial Cu (111) Foil: A Simple Approach to Improved Properties. *ACS nano* 2014, 8 (8), 8636-8643.

(13) Gomez De Arco, L.; Zhang, Y.; Schlenker, C. W.; Ryu, K.; Thompson, M. E.; Zhou, C. Continuous, Highly Flexible, and Transparent Graphene Films by Chemical Vapor Deposition for Organic Photovoltaics. *ACS nano* 2010, 4 (5), 2865-2873.

(14) Hernandez, Y.; Nicolosi, V.; Lotya, M.; Blighe, F. M.; Sun, Z.; De, S.; McGovern, I.; Holland, B.; Byrne, M.; Gun'Ko, Y. K. High-Yield Production of Graphene by Liquid-Phase Exfoliation of Graphite. *Nat. Nanotechnol.* 2008, 3 (9), 563.

(15) Krebs, F. C.; Fyenbo, J.; Jørgensen, M. Product Integration of Compact Roll-to-Roll Processed Polymer Solar Cell Modules: Methods and Manufacture Using Flexographic Printing, Slot-Die Coating and Rotary Screen Printing. *J. Mater. Chem.* 2010, 20 (41), DOI: 10.1039/c0jm01178a.

(16) Secor, E. B.; Prabhumirashi, P. L.; Puntambekar, K.; Geier, M. L.; Hersam, M. C. Inkjet Printing of High Conductivity, Flexible Graphene Patterns. *J. Phys. Chem. Lett.* 2013, 4 (8), 1347-51, DOI: 10.1021/jz400644c.

(17) Lamas-Ardisana, P. J.; Martinez-Paredes, G.; Anorga, L.; Grande, H. J. Glucose Biosensor Based on Disposable Electrochemical Paper-Based Transducers Fully Fabricated by Screen-Printing. *Biosens. Bioelectron.* 2018, 109, 8-12, DOI: 10.1016/j.bios.2018.02.061.

(18) Song, D.; Mahajan, A.; Secor, E. B.; Hersam, M. C.; Francis, L. F.; Frisbie, C. D. High-Resolution Transfer Printing of Graphene Lines for Fully Printed, Flexible Electronics. *ACS nano* 2017, 11 (7), 7431-7439.

(19) Hondred, J. A.; Breger, J. C.; Alves, N. J.; Trammell, S. A.; Walper, S. A.; Medintz, I. L.; Claussen, J. C. Printed Graphene Electrochemical Biosensors Fabricated by Inkjet Maskless Lithography for Rapid and Sensitive Detection of Organophosphates. *ACS Appl. Mater. Interfaces* 2018, 10 (13), 11125-11134.

(20) He, Q.; Das, S. R.; Garland, N. T.; Jing, D.; Hondred, J. A.; Cargill, A. A.; Ding, S.; Karunakaran, C.; Claussen, J. C. Enabling Inkjet Printed Graphene for Ion Selective Electrodes with Postprint Thermal Annealing. *ACS Appl. Mater. Interfaces* 2017, 9 (14), 12719-12727.

(21) Ding, S.; Das, S. R.; Brownlee, B. J.; Parate, K.; Davis, T.; Stromberg, L. R.; Chan, E. K.; Katz, J.; Iverson, B. D.; Claussen, J. C. Cip2a Immunosensor Comprised of Vertically-Aligned Carbon Nanotube Interdigitated Electrodes Towards Point-of-Care Oral Cancer Screening. *Biosens. Bioelectron.* 2018.

(22) Ding, S.; Mosher, C.; Lee, X. Y.; Das, S. R.; Cargill, A. A.; Tang, X.; Chen, B.; McLamore, E. S.; Gomes, C.; Hostetter, J. M.; Claussen, J. C. Rapid and Label-Free Detection of Interferon Gamma Via an Electrochemical Aptasensor Comprising a Ternary Surface Monolayer on a Gold Interdigitated Electrode Array. *ACS Sens.* 2017, 2 (2), 210-217, DOI: 10.1021/acssensors.6b00581.

(23) Van Gerwen, P.; Laureyn, W.; Laureys, W.; Huyberechts, G.; De Beeck, M. O.; Baert, K.; Suls, J.; Sansen, W.;

Jacobs, P.; Hermans, L. Nanoscaled Interdigitated Electrode Arrays for Biochemical Sensors. *Sens. Actuators, B* 1998, 49 (1-2), 73-80.

(24) Ko, S. H.; Pan, H.; Grigoropoulos, C. P.; Luscombe, C. K.; Fréchet, J. M.; Poulikakos, D. All-Inkjet-Printed Flexible Electronics Fabrication on a Polymer Substrate by Low-Temperature High-Resolution Selective Laser Sintering of Metal Nanoparticles. *Nanotechnology* 2007, 18 (34), 345202.

(25) Shimoni, A.; Azoubel, S.; Magdassi, S. Inkjet Printing of Flexible High-Performance Carbon Nanotube Transparent Conductive Films by "Coffee Ring Effect". *Nanoscale* 2014, 6 (19), 11084-11089.

(26) Zhang, L.; Liu, H.; Zhao, Y.; Sun, X.; Wen, Y.; Guo, Y.; Gao, X.; Di, C. a.; Yu, G.; Liu, Y. Inkjet Printing High-Resolution, Large-Area Graphene Patterns by Coffee-Ring Lithography. *Adv. Mater.* 2012, 24 (3), 436-440.

(27) Zhang, Z.; Zhang, X.; Xin, Z.; Deng, M.; Wen, Y.; Song, Y. Controlled Inkjetting of a Conductive Pattern of Silver Nanoparticles Based on the Coffee-Ring Effect. *Adv. Mater.* 2013, 25 (46), 6714-6718.

(28) Jabari, E.; Toyserkani, E. Micro-Scale Aerosol-Jet Printing of Graphene Interconnects. *Carbon* 2015, 91, 321-329.

(29) Secor, E. B. Principles of Aerosol Jet Printing. *Flex. Print. Electron.* 2018, 3 (3), 035002.

(30) Cai, F.; Chang, Y.-h.; Wang, K.; Khan, W. T.; Pavlidis, S.; Papapolymerou, J. In *High Resolution Aerosol Jet Printing of D-Band Printed Transmission Lines on Flexible Lcp Substrate*, 2014 IEEE MTT-S International Microwave Symposium (IMS2014), IEEE: 2014; pp 1-3.

(31) Mahajan, A.; Frisbie, C. D.; Francis, L. F. Optimization of Aerosol Jet Printing for High-Resolution, High-Aspect Ratio Silver Lines. *ACS Appl. Mater. Interfaces* 2013, 5 (11), 4856-64, DOI: 10.1021/am400606y.

(32) Deiner, L. J.; Reitz, T. L. Inkjet and Aerosol Jet Printing of Electrochemical Devices for Energy Conversion and Storage. *Adv. Eng. Mater.* 2017, 19 (7), 1600878.

(33) Akedo, J. In *Aerosol Deposition Method for Fabrication of Nano Crystal Ceramic Layer*, Materials Science Forum, Trans Tech Publ: 2004; pp 4348.

(34) Ha, M.; Seo, J.-W. T.; Prabhumirashi, P. L.; Zhang, W.; Geier, M. L.; Renn, M. J.; Kim, C. H.; Hersam, M. C.; Frisbie, C. D. Aerosol Jet Printed, Low Voltage, Electrolyte Gated Carbon Nanotube Ring Oscillators with Sub-5 Ms Stage Delays. *Nano Lett.* 2013, 13 (3), 954-960.

(35) Kim, S. H.; Hong, K.; Lee, K. H.; Frisbie, C. D. Performance and Stability of Aerosol-Jet-Printed Electrolyte-Gated Transistors Based on Poly (3-Hexylthiophene). *ACS Appl Mater Interfaces* 2013, 5 (14), 6580-6585.

(36) Pandhi, T.; Kreit, E.; Aga, R.; Fujimoto, K.; Sharbati, M. T.; Khademi, S.; Chang, A. N.; Xiong, F.; Koehne, J.; Heckman, E. M. Electrical Transport and Power Dissipation in Aerosol-Jet-Printed Graphene Interconnects. *Sci. Rep.* 2018, 8.

(37) Bodini, A.; Serpelloni, M.; Sardini, E.; Tonello, S. In *Design and Implementation of a Microsensor Platform for Protein Detection Realized Via 3-D Printing*, 2018 IEEE Sensors Applications Symposium (SAS), IEEE: 2018; pp 1-6.

(38) Grunwald, I.; Groth, E.; Wirth, I.; Schumacher, J.; Maiwald, M.; Zoellmer, V.; Busse, M. Surface Biofunctionalization and Production of Miniaturized Sensor Structures Using Aerosol Printing Technologies. *Biofabrication* 2010, 2 (1), 014106.

(39) Marziano, M.; Tonello, S.; Cantù, E.; Abate, G.; Vezzoli, M.; Rungratanawanich, W.; Serpelloni, M.; Lopomo, N.; Memo, M.; Sardini, E. Monitoring Caco-2 to Enterocyte-Like Cells Differentiation by Means of Electric Impedance Analysis on Printed Sensors. *Biochim. Biophys. Acta. Gen. Subj.* 2019, 1863 (5), 893-902.

(40) Ye, R.; James, D. K.; Tour, J. M. Laser-Induced Graphene. *Acc. Chem. Res.* 2018, 51 (7), 1609-1620.

(41) Conti-Freitas, L. C.; Foss-Freitas, M. C.; Mamede, R.; Foss, N. T. Interferon-Gamma and Interleukin-10 Production by Mononuclear Cells from Patients with Advanced Head and Neck Cancer. *Clinics* 2012, 67 (6), 587-590.

(42) Radbruch, A.; Braun, J.; Sieper, J.; Liu, L.; Neure, L.; Grolms, M.; Siegert, S.; Eggens, U.; Yin, Z. The Elevated Ratio of Interferon Gamma-/Interleukin-4-Positive T Cells Found in Synovial Fluid and Synovial Membrane of Rheumatoid Arthritis Patients Can Be Changed by Interleukin-4 but Not by Interleukin-10 or Transforming Growth Factor Beta. *Rheumatology* 1999, 38 (11), 1058-1067, DOI: 10.1093/rheumatology/38.11.1058.

(43) Skolimowska, K. H.; Rangaka, M. X.; Meiitjes, G.; Pepper, D. J.; Seldon, R.; Matthews, K.; Wilkinson, R. J.; Wilkinson, K. A. Altered Ratio of Ifn-Γ/Il-10 in Patients with Drug Resistant *Mycobacterium tuberculosis* and Hiv-Tuberculosis Immune Reconstitution Inflammatory Syndrome. *PLoS One* 2012, 7 (10), e46481.

(44) Khalifeh, M. S.; Stabel, J. R. Effects of Gamma Interferon, Interleukin-10, and Transforming Growth Factor on the Survival of *Mycobacterium avium* Subsp. Paratuberculosis in Monocyte-Derived Macrophages from Naturally Infected Cattle. *Infect. Immun.* 2004, 72 (4), 1974-1982, DOI: 10.1128/iai.72.4.1974-1982.2004.

(45) Khalifeh, M. S.; Stabel, J. R. Upregulation of Transforming Growth Factor-Beta and Interleukin-10 in Cows with Clinical Johne's Disease. *Vet. Immunol. Immunopathol.* 2004, 99 (1-2), 39-46, DOI: 10.1016/j.vetimm.2004.01.009.

(46) López-Maderuelo, D.; Arnalich, F.; Serantes, R.; Gonzalez, A.; Codoceo, R.; Madero, R.; Vázquez, J. J.; Montiel, C. Interferon-Γ and Iterleukin-10 Gene Polymorphisms in Pulmonary Tuberculosis. *Am. J. Respir. Crit. Care Med.* 2003, 167 (7), 970-975.

(47) Piazzolla, G.; Tortorella, C.; Schiraldi, O.; Antonaci, S. Relationship between Interferon-Γ, Interleukin-10, and Interleukin-12 Production in Chronic Hepatitis C and in Vitro Effects of Interferon-A. *J. Clin. Immunol* 2000, 20 (1), 54-61.

(48) Bjerre, A.; Brusletto, B.; Høiby, E. A.; Kierulf, P.; Brandtzaeg, P. Plasma Interferon-Γ and Interleukin-10 Concentrations in Systemic Meningococcal Disease Compared with Severe Systemic Gram-Positive Septic Shock. *Crit. Care Med.* 2004, 32 (2), 433-438.

(49) Secor, E. B.; Cook, A. B.; Tabor, C. E.; Hersam, M. C. Wiring up Liquid Metal: Stable and Robust Electrical Contacts Enabled by Printable Graphene Inks. *Adv. Electron. Mater.* 2018, 4 (1), 1700483.

(50) Secor, E. B.; Gao, T. Z.; Islam, A. E.; Rao, R.; Wallace, S. G.; Zhu, J.; Putz, K. W.; Maruyama, B.; Hersam, M. C. Enhanced Conductivity, Adhesion, and Environmental Stability of Printed Graphene Inks with Nitrocellulose. *Chem. Mater.* 2017, 29 (5), 2332-2340.

(51) Qu, J.; He, N.; Patil, S. V.; Wang, Y.; Banerjee, D.; Gao, W. Screen Printing of Graphene Oxide Patterns onto Viscose Nonwovens with Tunable Penetration Depth and Electrical Conductivity. *ACS Appl. Mater. Interfaces* 2019, 11 (16), 14944-14951.

(52) Sui, Y.; Hess-Dunning, A.; Wei, P.; Pentzer, E.; Sankaran, R. M.; Zorman, C. A. Electrically Conductive, Reduced Graphene Oxide Structures Fabricated by Inkjet Printing and Low Temperature Plasma Reduction. *Adv. Mater. Technol.* 2019, 1900834.

(53) Secor, E. B.; Gao, T. Z.; Islam, A. E.; Rao, R.; Wallace, S. G.; Zhu, J.; Putz, K. W.; Maruyama, B.; Hersam, M. C. Enhanced Conductivity, Adhesion, and Environmental Stability of Printed Graphene Inks with Nitrocellulose. *Chem. Mater.* 2017, 29 (5), 2332-2340.

(54) Majee, S.; Song, M.; Zhang, S.-L.; Zhang, Z.-B. Scalable Inkjet Printing of Shear-Exfoliated Graphene Transparent Conductive Films. *Carbon* 2016, 102, 51-57.

(55) Ferrari, A. C.; Meyer, J.; Scardaci, V.; Casiraghi, C.; Lazzeri, M.; Mauri, F.; Piscanec, S.; Jiang, D.; Novoselov, K.; Roth, S. Raman Spectrum of Graphene and Graphene Layers. *Phys. Rev. Lett.* 2006, 97 (18), 187401.

(56) Stankovich, S.; Dikin, D. A.; Piner, R. D.; Kohlhaas, K. A.; Kleinhammes, A.; Jia, Y.; Wu, Y.; Nguyen, S. T.; Ruoff, R. S. Synthesis of Graphene-Based Nanosheets Via Chemical Reduction of Exfoliated Graphite Oxide. *carbon* 2007, 45 (7), 1558-1565.

(57) Yang, D.; Velamakanni, A.; Bozoklu, G.; Park, S.; Stoller, M.; Piner, R. D.; Stankovich, S.; Jung, I.; Field, D. A.; Ventrice Jr, C. A. Chemical Analysis of Graphene Oxide Films after Heat and Chemical Treatments by X-Ray Photoelectron and Micro-Raman Spectroscopy. *Carbon* 2009, 47 (1), 145-152.

(58) Pimenta, M.; Dresselhaus, G.; Dresselhaus, M. S.; Cancado, L.; Jorio, A.; Saito, R. Studying Disorder in Graphite-Based Systems by Raman Spectroscopy. *Phys. Chem. Chem. Phys.* 2007, 9 (11), 1276-1290.

(59) Childres, I.; Jauregui, L. A.; Park, W.; Cao, H.; Chen, Y. P. *Raman Spectroscopy of Graphene and Related Materials*, 2013; Vol. 1.

(60) Torrisi, F.; Hasan, T.; Wu, W.; Sun, Z.; Lombardo, A.; Kulmala, T. S.; Hsieh, G.-W.; Jung, S.; Bonaccorso, F.; Paul, P. J. Inkjet-Printed Graphene Electronics. *ACS nano* 2012, 6 (4), 2992-3006.

(61) Karuppiah, C.; Cheemalapati, S.; Chen, S.-M.; Palanisamy, S. Carboxyl-Functionalized Graphene Oxide-Modified Electrode for the Electrochemical Determination of Nonsteroidal Anti-Inflammatory Drug Diclofenac. *Ionics* 2015, 21 (1), 231-238.

(62) Ambrosi, A.; Chua, C. K.; Bonanni, A.; Pumera, M. Electrochemistry of Graphene and Related Materials. *Chem. Rev.* 2014, 114 (14), 7150-7188.

(63) Ambrosi, A.; Pumera, M. Electrochemistry at Cvd Grown Multilayer Graphene Transferred onto Flexible Substrates. *J. Phys. Chem. C* 2013, 117 (5), 2053-2058.

(64) Pope, M. A.; Punckt, C.; Aksay, I. A. Intrinsic Capacitance and Redox Activity of Functionalized Graphene Sheets. *J. Phys. Chem. C* 2011, 115 (41), 20326-20334.

(65) Bard, A. J.; Faulkner, L. R. *Electrochemical Methods: Fundamentals and Applications*, Wiley New york, NY, USA: 2001.

(66) Mao, S.; Yu, K.; Lu, G.; Chen, J. Highly Sensitive Protein Sensor Based on Thermally-Reduced Graphene Oxide Field-Effect Transistor. *Nano Res.* 2011, 4 (10), 921.

(67) Yang, F.; Han, J.; Zhuo, Y.; Yang, Z.; Chai, Y.; Yuan, R. Highly Sensitive Impedimetric Immunosensor Based on Single-Walled Carbon Nanohorns as Labels and Bienzyme Biocatalyzed Precipitation as Enhancer for Cancer Biomarker Detection. *Biosens. Bioelectron.* 2014, 55, 360-365.

(68) Lago, P.; Boéchat, N.; Migueis, D.; Almeida, A.; Lazzarini, L.; Saldanha, M.; Kritski, A.; Ho, J.; Lapa e Silva, J. Interleukin-10 and Interferon-Gamma Patterns During Tuberculosis Treatment: Possible Association with Recurrence. *Int. J. Tuberc. Lung Dis.* 2012, 16 (5), 656-659.

(69) Zdanov, A.; Schalk-Hihi, C.; Gustchina, A.; Tsang, M.; Weatherbee, J.; Wlodawer, A. Crystal Structure of Interleukin-10 Reveals the Functional Dimer with an Unexpected Topological Similarity to Interferon Γ. *Structure* 1995, 3 (6), 591-601.

(70) Lai, C.-F.; Ripperger, J.; Morella, K. K.; Jurlander, J.; Hawley, T. S.; Carson, W. E.; Kordula, T.; Caligiuri, M. A.; Hawley, R. G.; Fey, G. H. Receptors for Interleukin (Il)-10 and Il-6-Type Cytokines Use Similar Signaling Mechanisms for Inducing Transcription through Il-6 Response Elements. *J. Biol. Chem.* 1996, 271 (24), 13968-13975.

(71) Plattner, B.; Huffman, E.; Hostetter, J. Gamma-Delta T-Cell Responses During Subcutaneous *Mycobacterium avium* Subspecies Paratuberculosis Challenge in Sensitized or Naive Calves Using Matrix Biopolymers. *Vet. Pathol.* 2013, 50 (4), 630-637.

(72) Szodoray, P.; Alex, P.; Brun, J.; Centola, M.; Jonsson, R. Circulating Cytokines in Primary Sjögren's Syndrome Determined by a Multiplex Cytokine Array System. *Scand. J. Immunol.* 2004, 59 (6), 592-599.

(73) Zhang, B.; Price, J.; Hong, G.; Tabakman, S. M.; Wang, H.; Jarrell, J. A.; Feng, J.; Utz, P. J.; Dai, H. Multiplexed Cytokine Detection on Plasmonic Gold Substrates with Enhanced near-Infrared Fluorescence. *Nano Res.* 2012, 6 (2), 113-120, DOI: 10.1007/s12274-012-0286-2.

(74) Ooi, K. G.-J.; Galatowicz, G.; Towler, H. M.; Lightman, S. L.; Calder, V. L. Multiplex Cytokine Detection Versus Elisa for Aqueous Humor Il-5, Il-10, and Ifnγ Profiles in Uveitis. *Invest. Ophthalmol. Visual Sci.* 2006, 47 (1), 272-277.

(75) Fairchild, A. B.; McAferty, K.; Demirok, U. K.; La Belle, J. T. In *A Label-Free, Rapid Multimarker Protein Impedance-Based Immunosensor*, Complex Medical Engineering, 2009. CME. ICME International Conference on, IEEE: 2009; pp 1-5.

(76) Du, D.; Zou, Z.; Shin, Y.; Wang, J.; Wu, H.; Engelhard, M. H.; Liu, J.; Aksay, I. A.; Li, Y. Sensitive Immunosensor for Cancer Biomarker Based on Dual Signal Amplification Strategy of Graphene Sheets and Multienzyme Functionalized Carbon Nanospheres. *Anal. Chem.* 2010, 82 (7), 2989-2995.

(77) Carinelli, S.; Marti, M.; Alegret, S.; Pividori, M. I. Biomarker Detection of Global Infectious Diseases Based on Magnetic Particles. *New biotechnol.* 2015, 32 (5), 521-532.

(78) Viswanathan, S.; Rani, C.; Ho, J.-a. A. Electrochemical Immunosensor for Multiplexed Detection of FoodBorne Pathogens Using Nanocrystal Bioconjugates and Mwcnt Screen-Printed Electrode. *Talanta* 2012, 94, 315-319.

(79) Hyun, W. J.; Secor, E. B.; Rojas, G. A.; Hersam, M. C.; Francis, L. F.; Frisbie, C. D. All-Printed, Foldable Organic Thin-Film Transistors on Glassine Paper. *Adv. Mater.* 2015, 27 (44), 7058-7064.

(80) El-Kady, M. F.; Shao, Y.; Kaner, R. B. Graphene for Batteries, Supercapacitors and Beyond. *Nat. Rev. Mater.* 2016, 1 (7), 16033.

(81) Raccichini, R.; Varzi, A.; Passerini, S.; Scrosati, B. The Role of Graphene for Electrochemical Energy Storage. *Nat. Mater.* 2015, 14 (3), 271.

(82) Shao, Y.; El-Kady, M. F.; Li, C. W.; Zhu, G.; Marsh, K. L.; Hwang, J. Y.; Zhang, Q.; Li, Y.; Wang, H.; Kaner, R. B. 3d Freeze-Casting of Cellular Graphene Films for Ultrahigh-Power-Density Supercapacitors. *Adv. Mater.* 2016, 28 (31), 6719-6726.

(83) Yang, J.; Gunasekaran, S. Electrochemically Reduced Graphene Oxide Sheets for Use in High Performance Supercapacitors. *Carbon* 2013, 51, 36-44.

(84) Xiong, G.; He, P.; Huang, B.; Chen, T.; Bo, Z.; Fisher, T. S. Graphene Nanopetal Wire Supercapacitors with High Energy Density and Thermal Durability. *Nano energy* 2017, 38, 127-136.

(85) Koushanpour, A.; Guz, N.; Gamella, M.; Katz, E. Biofuel Cell Based on Carbon Fiber Electrodes Functionalized with Graphene Nanosheets. *ECS J. Solid State Sci. Technol* 2016, 5 (8), M3037-M3040.

(86) Xiao, L.; Damien, J.; Luo, J.; Jang, H. D.; Huang, J.; He, Z. Crumpled Graphene Particles for Microbial Fuel Cell Electrodes. *J. Power Sources* 2012, 208, 187-192.

(87) Gao, W.; Emaminejad, S.; Nyein, H. Y. Y.; Challa, S.; Chen, K.; Peck, A.; Fadah, H. M.; Ota, H.; Shiraki, H.; Kiriya, D. Fully Integrated Wearable Sensor Arrays for Multiplexed in Situ Perspiration Analysis. *Nature* 2016, 529 (7587), 509.

(88) Imani, S.; Bandodkar, A. J.; Mohan, A. V.; Kumar, R.; Yu, S.; Wang, J.; Mercier, P. P. A Wearable Chemical-Electrophysiological Hybrid Biosensing System for Real-Time Health and Fitness Monitoring. *Nat. Commun.* 2016, 7, 11650.

(89) Kim, J.; Campbell, A. S.; de Ávila, B. E.-F.; Wang, J. Wearable Biosensors for Healthcare Monitoring. *Nat. Biotechnol.* 2019, 1.

(90) Han, T.-H.; Lee, Y.; Choi, M.-R.; Woo, S.-H.; Bae, S.-H.; Hong, B. H.; Ahn, J.-H.; Lee, T.-W. Extremely Efficient Flexible Organic Light-Emitting Diodes with Modified Graphene Anode. *Nat. Photonics* 2012, 6 (2), 105.

(91) Park, H.; Chang, S.; Zhou, X.; Kong, J.; Palacios, T. s.; Gradečak, S. Flexible Graphene Electrode-Based Organic Photovoltaics with Record-High Efficiency. *Nano Lett.* 2014, 14 (9), 5148-5154.

(92) Tian, H.; Shu, Y.; Cui, Y.-L.; Mi, W.-T.; Yang, Y.; Xie, D.; Ren, T.-L. Scalable Fabrication of High-Performance and Flexible Graphene Strain Sensors. *Nanoscale* 2014, 6 (2), 699-705.

(93) Kim, J.; de Araujo, W. R.; Samek, I. A.; Bandodkar, A. J.; Jia, W.; Brunetti, B.; Paixão, T. R.; Wang, J. Wearable Temporary Tattoo Sensor for Real-Time Trace Metal Monitoring in Human Sweat. *Electrochem. Commun.* 2015, 51, 4145.

(94) Mannoor, M. S.; Tao, H.; Clayton, J. D.; Sengupta, A.; Kaplan, D. L.; Naik, R. R.; Verma, N.; Omenetto, F. G.; McAlpine, M. C. Graphene-Based Wireless Bacteria Detection on Tooth Enamel. *Nat. Commun.* 2012, 3, 763.

(95) Sonner, Z.; Wilder, E.; Heikenfeld, J.; Kasting, G.; Beyette, F.; Swaile, D.; Sherman, F.; Joyce, J.; Hagen, J.; Kelley-Loughnane, N. The Microfluidics of the Eccrine Sweat Gland, Including Biomarker Partitioning, Transport, and Biosensing Implications. *Biomicrofluidics* 2015, 9 (3), 031301.

Supporting Information

Aerosol-Jet-Printed Graphene Immunosensor for Label-Free Cytokine Monitoring in Serum Demonstration of Tunable Film Thickness with Printing Parameters:

Printed line morphology was characterized with laser profilometry using an Olympus OLS5000 laser confocal microscope. Optical micrographs (FIG. 9A) and 3D profiles (FIG. 9B) were collected simultaneously and then analyzed using Olympus software. The line in FIG. 9A and FIG. 9B was printed with a sheath flow rate of 55 sccm, carrier flow rate of 35 sccm, and printing speed of 10 mm/s. A single line profile was extracted from the 3D profile to simulate stylus profilometry, but averaging the traces over a larger line length yielded data that was more representative of the entire printed line (FIG. 9C). The averaged data in FIG. 9C was taken from the dashed box region, which was 200 μm long parallel to the printed line, in FIG. 9B. The averaged line profile was analyzed for maximum thickness, printed line width, and cross-sectional area of the line (FIG. 9D). This area measurement was used for subsequent calculations of conductivity. This analysis technique was used to characterize several lines printed under different conditions. FIG. 9E shows a linear trend of cross-sectional area with carrier flow rate while the print speed was held constant at 1 mm/s. These data demonstrate how aerosol jet printing can be used to tunably print features with sub-micron thickness.

Time remains a confounding variable during aerosol jet printing due to the continuously changing ink composition and volume; effectively, the deposition rate increases as a function of time while all other printing parameters are held constant. The cross-sectional area of printed lines as a function of number of passes for three sets of lines ranging from 1 to 30 passes is shown in FIG. 9F. Each set of lines took 5 minutes to print, and carrier and sheath flow rates, printing speed, and sonication power were held constant for this experiment. Each set shows an increase in cross-sectional area. This increase in cross-sectional area can be mitigated by decreasing the carrier flow rate at regular intervals.

Influence of Printed Graphene Porosity on Electrical Properties:

Cross-sectional SEM of printed graphene lines can be used to evaluate film porosity. In ultrathin (sub-100 nm) films printed on $SiO_2$, no porosity is observed (FIG. 10A). A 45° titled view of the top surface of the film in FIG. 10B shows that the ultrathin film is percolating, and nanosheets are stacked neatly on top of each other. However, in thicker films, porosity is observed in the cross-sectional SEM micrograph (FIG. 10C). Gaps in the films are also observed at the cleaved edge of the film from along the top surface at a 45° angle (FIG. 10D).

Printed Graphene Film Thickness on Kapton®:

Characterizing the thickness of graphene lines printed on Kapton® film was difficult due to its irregular surface. The Kapton® texture is observable under the optical microscope (scratches on the surface and randomly distributed dark spots are common), AFM (FIG. 4E shows depressions along the printed line), and confocal laser microscopy. The surface roughness of Kapton® was analyzed thoroughly with confocal laser microscopy to understand how best to assign a printed line thickness for the thinnest films.

First, a bare section of as-received Kapton® was scanned at the highest resolution objective of the Olympus confocal laser microscope (50× magnification with 200 nm lateral resolution and 6 nm vertical resolution). The optical image (FIG. 11A) shows spots and scratches, but the 3D scan of the film height (FIGS. 11B and C) shows additional topography. An areal roughness measurement of the dashed box region in FIG. 11B yields a root mean square roughness of 37 nm.

This technique was applied to a scanned image of an ultrathin (sub-100 nm) graphene line printed on Kapton® film (FIG. 11D). The root-mean-square areal roughness of the boxed regions of interest in FIG. 11D are 34 nm for Region 1 and 40 nm for Region 2. FIG. 11E shows the 2D height profile image of the same region. The printed line can barely be distinguished from the Kapton® film, indicating that the printed line thickness is less than or equal to the roughness of the substrate. A small local region 40 μm long (indicated by the dashed box) that seems to have the most contrast between the printed line and substrate is used to generate the averaged line profile shown in FIG. 11F. However, several peaks are visible in this averaged profile, and comparison of the 3D height image and optical micrograph indicates that not all the peaks are associated with the printed line. This film roughness analysis suggests that AFM is a more precise way of characterizing the thinnest of printed lines on Kapton and corroborates the AFM measurement of a 25 nm thick printed graphene line.

Analysis of Material Consumption During Printing:

As observed in FIG. 6B, a tradeoff exists between printed graphene film thickness and conductivity in the sub-200 nm limit. Thinner films have the benefit that the amount of material being printed is minimized. In practice, the thinnest films are achieved by aerosol jet printing at speeds of ≥5 mm/s. Thus, by prioritizing thin films, the throughput of the printer is also increased.

Table S1 shows the printing parameters and film characteristics of two lines printed on Kapton® that have different conductivities. Line A is thinner than line B and has 2 times lower conductivity. However, line A prints 5 times more quickly and consumes 2.6 times less material than B. Consequently, approximately 10 times the number of biosensing devices can be achieved at the printing conditions of line A.

TABLE S1

Comparison of printed line properties

| Line | Print time (s/mm) | Thickness (μm) | Cross-sectional area (μm$^2$) | Conductivity (S/m) |
|---|---|---|---|---|
| A | 0.167 | 0.073 | 1.807 | $2.66 \times 10^4$ |
| B | 0.833 | 0.161 | 4.64 | $5.39 \times 10^4$ |
| Ratio (B/A) | 5 | 2.205 | 2.568 | 2.03 |

Comparison of Electronic Properties of Printed Graphene Lines:

While there have been many studies on the conductivity of printed graphene films, this work stands out as having produced one of the thinnest films with highest conductivity (Table S2). Furthermore, aerosol jet printed graphene interdigitated electrodes have achieved low interfinger spacing through a scalable fabrication method as well as a high capacitance of 1.5 mF/cm$^2$ (Table S3). These results speak to the utility of graphene-nitrocellulose based inks in printed electronics.

TABLE S2

Conductive graphene films

| Material | Deposition Method | Printed Thickness | Film Conductivity (S/m) | Ref. |
|---|---|---|---|---|
| Graphene | Blade coating | ~2 μm* | $4 \times 10^4$ | 1 |
| Graphene | IJP | 150 nm | $2.5 \times 10^4$ | 2 |
| Graphene | AJP | 170 nm | $5.5 \times 10^{3*}$ | 3 |
| Graphene | IJP | 160 nm | $3 \times 10^3$ | 4 |
| Graphene | AJP | 1.5 μm* | $1 \times 10^{3*}$ | 5 |
| Graphene | IJP | 75 μm | $2.4 \times 10^2$ | 6 |
| Graphene | IJP | 25 nm | $1 \times 10^2$ | 7 |
| Graphene | IJP | | $5 \times 10^1$ | 8 |
| Graphene | AJP | 25 nm | $1.5 \times 10^4$ | This work |

*Calculated or estimated from available data.

TABLE S3

Interdigitated graphene-family capacitors

| Material | Patterning Method | Finger spacing | Capacitance | Ref. |
|---|---|---|---|---|
| rGO | IJP | 1.3 mm * | 48-132 F/g | 9 |
| Graphene | IJP | 300 μm | 40-130 μF/cm$^2$ | 10 |
| Graphene | IJP | 1 mm | | 4 |
| Graphene | Photolithography | 20 μm | 268 μF/cm$^2$ | 11 |
| Graphene | Laser writing | 300 μm | 3-10 mF/cm$^2$ * | 12 |
| Graphene | AJP | 100 μm | 134.3 μF/cm$^2$ – 1.5 mF/cm$^2$ | This work |

* Calculated or estimated from available data.

While the data for line thickness and conductivity of graphene lines are reported for lines printed on Kapton® substrates, the substrate choice does not have a significant impact on conductivity. FIG. 12 compares the conductivity vs. film thickness for graphene lines printed on Kapton® and 300 nm SiO$_2$; there is no significant variation in the order of the electrical conductivity magnitude. The trend for both the substrates changes in a similar fashion, in which the conductivity first increases till about 200 nm and then drops for lines thicker than that. This demonstrates that the line conductivity is independent of the substrate used for printing.

SEM Images of Graphene Interdigitated Electrode Before and After CO$_2$ Annealing:

From the FIGS. 13A-B, it is evident that the printed graphene feature on the polyimide substrate is not significantly affected by the CO$_2$ thermal annealing process. This is in correspondence with the Raman spectra in FIG. 5C that shows no significant change in the graphene peaks and therefore, indicating that there is no observable shrinkage of the printed material caused by CO$_2$ annealing.

Calculation of Electrochemical Surface Area:

For a one electron electrochemical system that is totally irreversible ($\Delta E_p > 200$ mV), first the charge transfer coefficient ($\alpha$) needs to be calculated.[13] The value of $\alpha$ can be calculated from the plot of peak voltages versus logarithm of scan rate (FIG. 14A). For anodic peak voltage, $\alpha$ can be determined from the slope of the line as $$\text{slope} = \frac{2.3\, RT}{(1-\alpha)nF}.$$

[13] From the FIG. 14A, the regression equation obtained was y=290.72x+1135.8 with $R^2$=0.99, which leads to $\alpha$=0.8. Next, the electrochemical surface area can be calculated from the Randles-Ševčik equation and slope of the Randles-Ševčik plot (FIG. 14B) for anodic current using the equation: slope=$2.99 \times 10^5 \alpha^{1/2} A C_o D_o^{1/2}$.[14] Here, $C_o$ is the concentration of redox probe (=5 mM), $D_o$ is the diffusion coefficient of the redox probe (=$7.2 \times 10^{-6}$ cm$^2$/s), A is the electrochemical surface area of the electrode and the regression equation for the anodic peak current was obtained as y=0.0003x+3e-5 with $R^2$=0.97. It is recommended to use forward (anodic) peak current rather than cathodic peak current for the calculation, because of a decrease in the product formed in the reverse cycle and therefore, a less intense peak.[15] The electrochemical surface area of the aerosol jet printed (AJP) interdigitated electrode (IDE) was calculated as 8.4 mm$^2$.

Optimization of Blocking Agent for Biofunctionalization of AJP IDE:

See FIGS. 15A-D and their description in the Brief Description of the Drawings section supra.

Mechanical Flexibility Measurement:

See FIG. 16 and its description in the Brief Description of the Drawings section supra.

References for Embodiment 2

(1) Secor, E. B.; Gao, T. Z.; Islam, A. E.; Rao, R.; Wallace, S. G.; Zhu, J.; Putz, K. W.; Maruyama, B.; Hersam, M. C. Enhanced Conductivity, Adhesion, and Environmental Stability of Printed Graphene Inks with Nitrocellulose. *Chem. Mater.* 2017, 29 (5), 2332-2340.

(2) Secor, E. B.; Prabhumirashi, P. L.; Puntambekar, K.; Geier, M. L.; Hersam, M. C. Inkjet Printing of High Conductivity, Flexible Graphene Patterns. *J. Phys. Chem. Lett.* 2013, 4 (8), 1347-51, DOI: 10.1021/jz400644c.

(3) Jabari, E.; Toyserkani, E. Micro-Scale Aerosol-Jet Printing of Graphene Interconnects. *Carbon* 2015, 91, 321-329.

(4) Finn, D. J.; Lotya, M.; Cunningham, G.; Smith, R. J.; McCloskey, D.; Donegan, J. F.; Coleman, J. N. Inkjet Deposition of Liquid-Exfoliated Graphene and Mos 2 Nanosheets for Printed Device Applications. *J. Mater. Chem. C* 2014, 2 (5), 925-932.

(5) Pandhi, T.; Kreit, E.; Aga, R.; Fujimoto, K.; Sharbati, M. T.; Khademi, S.; Chang, A. N.; Xiong, F.; Koehne, J.; Heckman, E. M. Electrical Transport and Power Dissipation in Aerosol-Jet-Printed Graphene Interconnects. *Sci. Rep.* 2018, 8.

(6) Huang, S.; Shen, R.; Qian, B.; Li, L.; Wang, W.; Li, G.; Zhang, X.; Li, P.; Xie, Y. Thermal Bubble Inkjet Printing of Water-Based Graphene Oxide and Graphene Inks on Heated Substrate. *J. Phys. D: Appl. Phys.* 2018, 51 (13), 135302.

(7) Torrisi, F.; Hasan, T.; Wu, W.; Sun, Z.; Lombardo, A.; Kulmala, T. S.; Hsieh, G.-W.; Jung, S.; Bonaccorso, F.; Paul, P. J. Inkjet-Printed Graphene Electronics. *ACS nano* 2012, 6 (4), 2992-3006.

(8) Kim, J.; Kwon, S.; Cho, D.-H.; Kang, B.; Kwon, H.; Kim, Y.; Park, S. O.; Jung, G. Y.; Shin, E.; Kim, W.-G. Direct Exfoliation and Dispersion of Two-Dimensional Materials in Pure Water Via Temperature Control. *Nat. Commun.* 2015, 6, 8294.

(9) Le, L.; Ervin, M.; Qiu, H.; Fuchs, B.; Zunino, J.; Lee, W. In *Inkjet-Printed Graphene for Flexible Micro-Supercapacitors*, Proc. IEEE Conf. Nanotechnol., IEEE: 2011; pp 67-71.

(10) Li, J.; Mishukova, V.; Östling, M. All-Solid-State Micro-Supercapacitors Based on Inkjet Printed Graphene Electrodes. *Appl. Phys. Lett.* 2016, 109 (12), 123901.

(11) Hyun, W. J.; Secor, E. B.; Kim, C. H.; Hersam, M. C.; Francis, L. F.; Frisbie, C. D. Scalable, Self-Aligned Printing of Flexible Graphene Micro-Supercapacitors. *Adv. Energy Mater.* 2017, 7 (17), 1700285.

(12) Li, L.; Zhang, J.; Peng, Z.; Li, Y.; Gao, C.; Ji, Y.; Ye, R.; Kim, N. D.; Zhong, Q.; Yang, Y. High-Performance Pseudocapacitive Microsupercapacitors from Laser-Induced Graphene. *Adv. Mater.* 2016, 28 (5), 838-845.

(13) Laviron, E. General Expression of the Linear Potential Sweep Voltammogram in the Case of Diffusionless Electrochemical Systems. *J. Electroanal. Chem. Interfacial Electrochem.* 1979, 101 (1), 19-28.

(14) Bard, A. J.; Faulkner, L. R.; Leddy, J.; Zoski, C. G. *Electrochemical Methods: Fundamentals and Applications*, wiley New York: 1980; Vol. 2.

(15) García-Miranda Ferrari, A.; Foster, C.; Kelly, P.; Brownson, D.; Banks, C. Determination of the Electrochemical Area of Screen-Printed Electrochemical Sensing Platforms. *Biosensors* 2018, 8 (2), 53.

D. Embodiment 3—Specific Example

Another example of proof of concept follows. This is taken from Parate, K., Pola, C. C., Rangnekar, S. V., Mendivelso-Perez, D. L., Smith, E. A., Hersam, M. C., Gomes, C. L., & Claussen, J. C. (2020). Aerosol-jet-printed graphene electrochemical histamine sensors for food safety monitoring. *2D Materials*, 7(3), [034002]. https://doi.org/10.1088/2053-1583/ab8919, and its Supplementary Information, both of which are incorporated by reference herein in their entireties. It is to be understood this is one example of aspects of the invention.

Aerosol-Jet-Printed Graphene Electrochemical Histamine Sensors for Food Safety Monitoring Abstract Carbon nanomaterials such as graphene exhibit unique material properties such as high electrical conductivity, surface area, and biocompatibility that have the potential to significantly improve the performance of electrochemical sensors. Since in-field electrochemical sensors are typically disposable, they require materials that are amenable to low-cost, high-throughput, and scalable manufacturing. Conventional graphene devices based on low-yield chemical vapor deposition techniques are too expensive for such applications, while low-cost alternatives such as screen and inkjet printing do not possess sufficient control over electrode geometry to achieve favorable electrochemical sensor performance. In this work, aerosol jet printing (AJP) is used to create high-resolution (~40 µm line width) interdigitated electrodes (IDEs) on flexible substrates, which are then converted into histamine sensors by covalently linking monoclonal antibodies to oxygen moieties created on the graphene surface through a $CO_2$ thermal annealing process. The resulting electrochemical sensors exhibit a wide histamine sensing range of 6.25-200 ppm (56.25 µM-1.8 mM) and a low detection limit of 3.41 ppm (30.7 µM) within actual tuna broth samples. These sensor metrics are significant since histamine levels over 50 ppm in fish induce adverse health effects including severe allergic reactions (e.g., Scombroid food poisoning). Beyond the histamine case study presented here, the AJP and functionalization process can likely be generalized to a diverse range of sensing applications including environmental toxin detection, foodborne pathogen detection, wearable health monitoring, and health diagnostics.

1. Introduction

Graphene is being implemented in a wide range of devices including transistors, sensors, and energy storage devices because of its high mechanical strength, electrical conductivity, electroactivity, and thermal conductivity [1-3]. Graphene used in such devices is typically synthesized through chemical vapor deposition (CVD) [4], epitaxial growth [5], laser ablation methods [6], and thermal decomposition of silicon carbide [7], which are generally expensive, high-energy, low-yield processes performed on rigid substrates (e.g., silicon). Moreover, the graphene has to be either transferred to a device-compatible substrate through wet chemical transfer steps or physical stamping processes [8, 9], or the graphene needs to be patterned on a growth substrate into a device through atomic layer etching [10], focused ion beam patterning [11], or block copolymer lithography [12, 13]. Although these techniques are capable of manufacturing high-resolution devices (<50 μm line resolution), they are energy intensive and low yield, and often require sophisticated cleanroom processing [14-16].

Printing of graphene and graphene oxide flakes acquired through bulk, high-yield exfoliation of graphite represents a low-cost and scalable alternative to creating graphene-based devices [17, 18]. However, these printing techniques generally produce low-resolution graphene devices with feature sizes that typically range between a few hundreds of microns and a few millimeters [19-22]. To attain higher resolution (<50 μm), additional laborious steps such as lithographic patterning [23], high-resolution stencil fabrication [2, 24], or sacrificial mask layers [2, 24, 25] are needed. In addition, these manufacturing techniques are subtractive rather than additive and hence are less amenable to scalability.

Aerosol jet printing (AJP) offers an alternative high-yield and high-resolution printing technique for device fabrication. This direct-write, additive printing method eliminates the requirement of several fabrication steps and is capable of generating high-resolution features without the need of auxiliary patterning [26, 27]. In AJP, a printable ink is atomized by a pneumatic or ultrasonic mechanism, and then focused onto a substrate using a coaxial air sheath. This printing mechanism implies that AJP is amenable to a wide range of inks with relaxed viscosity tolerance (1-1000 mPa·s) compared to other additive manufacturing methods [28]. Furthermore, AJP is compatible with a variety of flexible and rigid substrates such as conductors, semiconductors, and dielectrics, including nonplanar surfaces and chemically or thermally sensitive samples [29]. AJP has been used to fabricate transistors, electrodes, supercapacitors, fuel cells, and solar cells, and also for a few electrochemical biosensing applications such as sensing biomolecules including glucose, proteins such as interferon-gamma and interleukin-10 for the detection of Johne's disease, interleukin-8 and for cells differentiation studies [29-34]. However, its application for detecting food allergens such as histamine is yet to be shown.

Herein, we experimentally realize an AJP graphene-based histamine sensor that is suitable for rapid in-field monitoring. Histamine (2-(1H-imidazol-4-yl)ethanamine) is a biogenic amine associated with fish product spoilage and seafood allergies [35, 36] that currently is monitored for food safety through tedious laboratory techniques (e.g., fluorescence [37], high-performance liquid chromatography (HPLC) [38], thin layer chromatography [39], liquid chromatography with mass spectrometry [40], enzyme-linked immunosorbent assay (ELISA) [41], and impedimetric techniques [42]), which require hours to quantify histamine concentrations within a sample. While electrochemical sensing for histamine has been demonstrated previously, it usually involves depositing metallic nanoparticles [43, 44] or carbon-based materials on an electrode surface [45, 46], or the use of labeled enzyme mediated reactions [47, 48]. In contrast, our histamine biosensor circumvents the need for laboratory analysis and is capable of electrochemically quantifying histamine concentrations in food fluids with a response time of only 33 min (including incubation), which is appreciably faster than the traditional methods for histamine detection. The biosensor is aerosol jet printed in the form of an interdigitated electrode (IDE) on a polyimide sheet (Kapton®) with a graphene-nitrocellulose ink that results in high signal-to-noise ratios, fast response times, and enhanced reaction-diffusion kinetics during electrochemical sensing [49, 50]. The printed graphene IDE consists of 50 fingers of 40 μm width and 100 μm spacing, surpassing the resolution of traditional inkjet-printed electrodes, and are functionalized with oxygenated moieties through $CO_2$ thermal annealing [51]. These oxygen species are used to covalently link histamine antibody to the graphene surface through carbodiimide cross-linking chemistry. The resulting biosensor is capable of sensing histamine in buffer solution and real fish broth at biologically relevant concentrations with negligible interference or non specific adsorption from competing proteins.

2. Results and Discussion 2.1. Fabrication of Aerosol Jet Printed (AJP) Graphene Interdigitated Electrode (IDE)

Figure 17A:
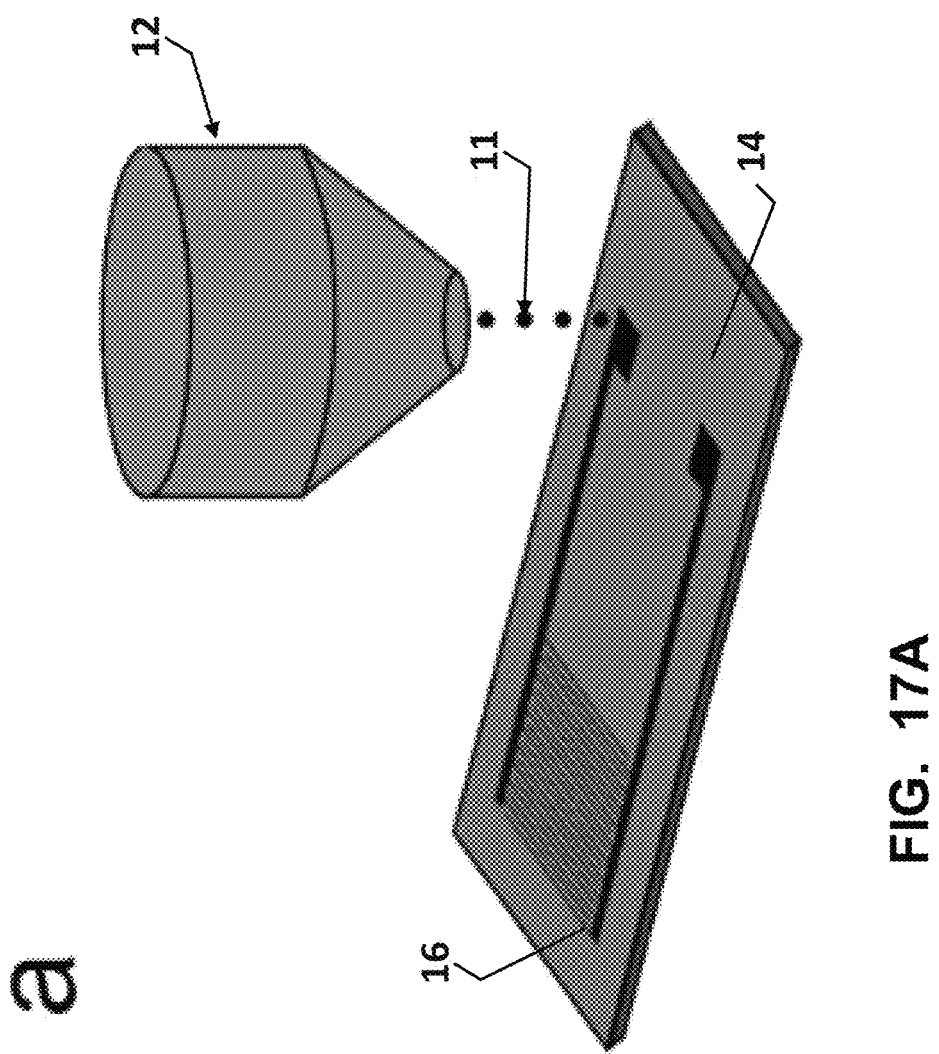
Figure 17B:
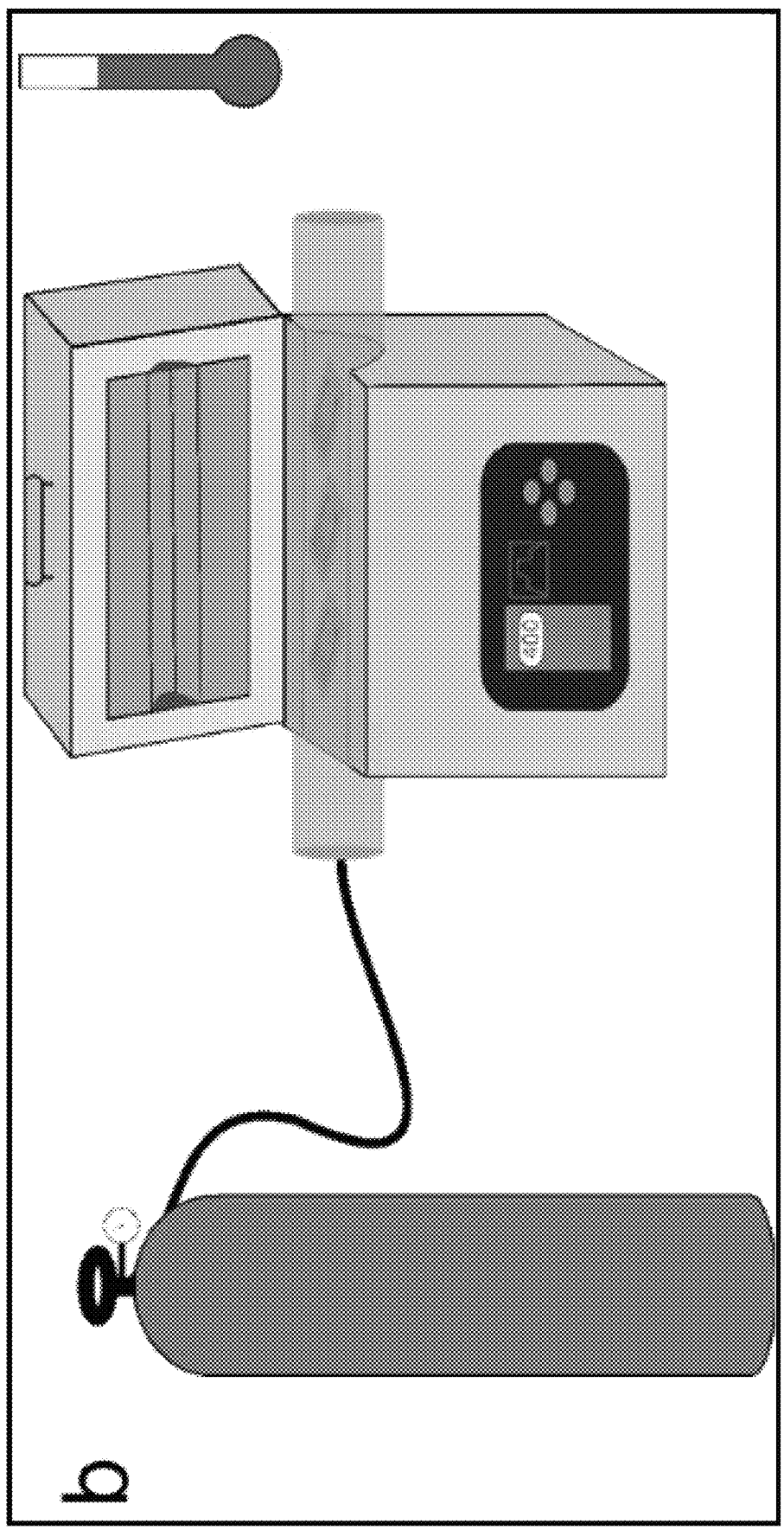
Figure 17C:
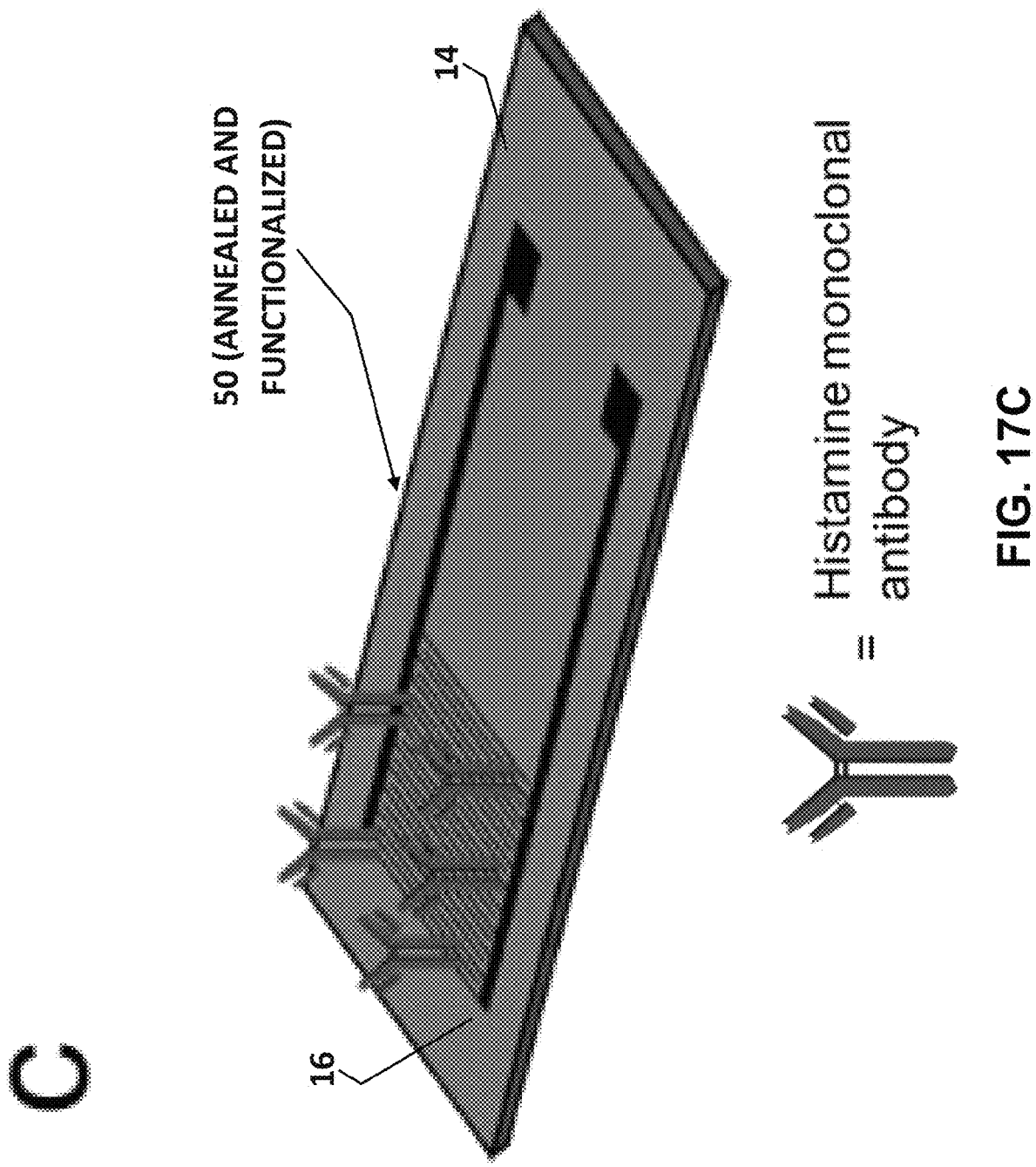
Figure 17D:
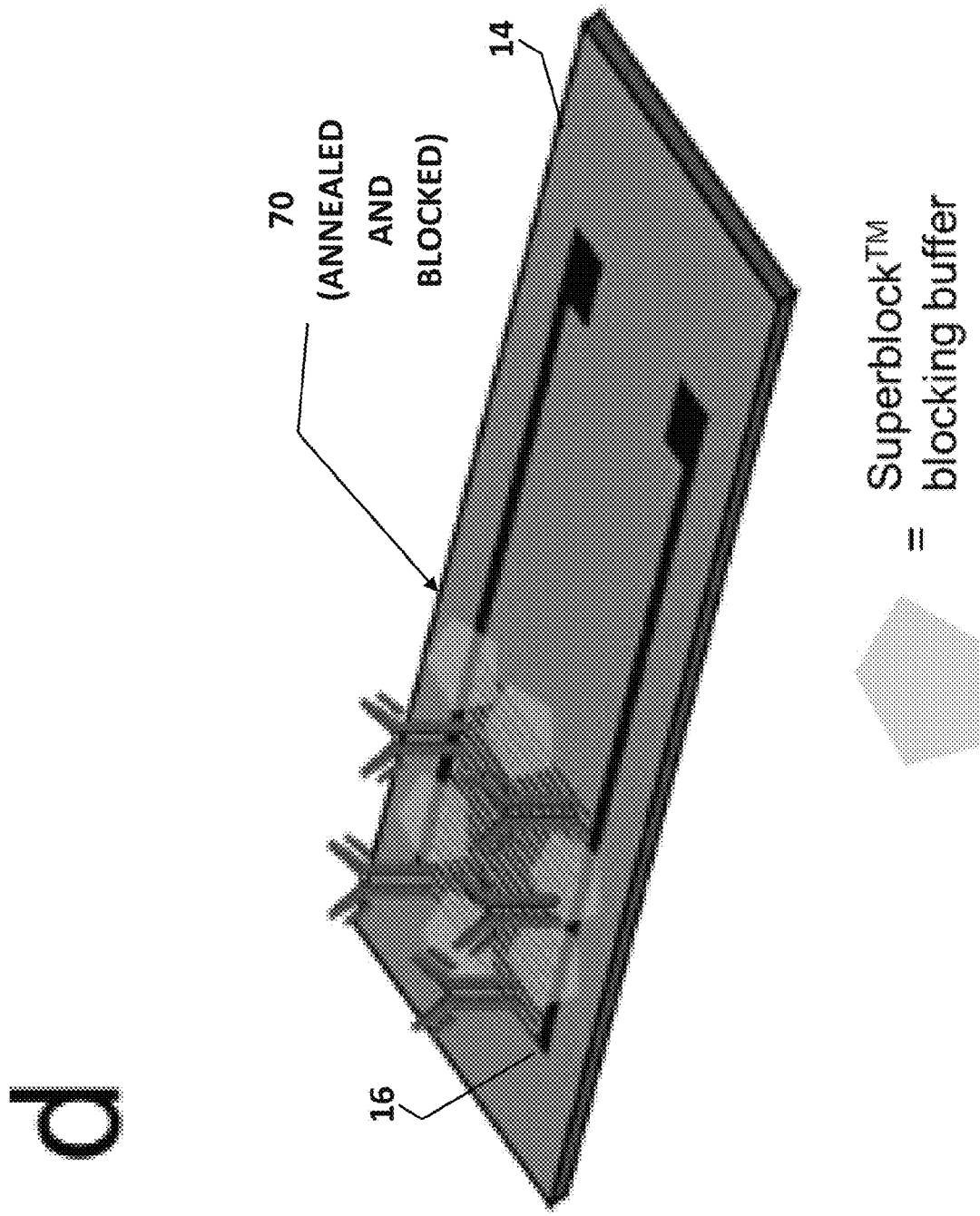
Figure 17E:
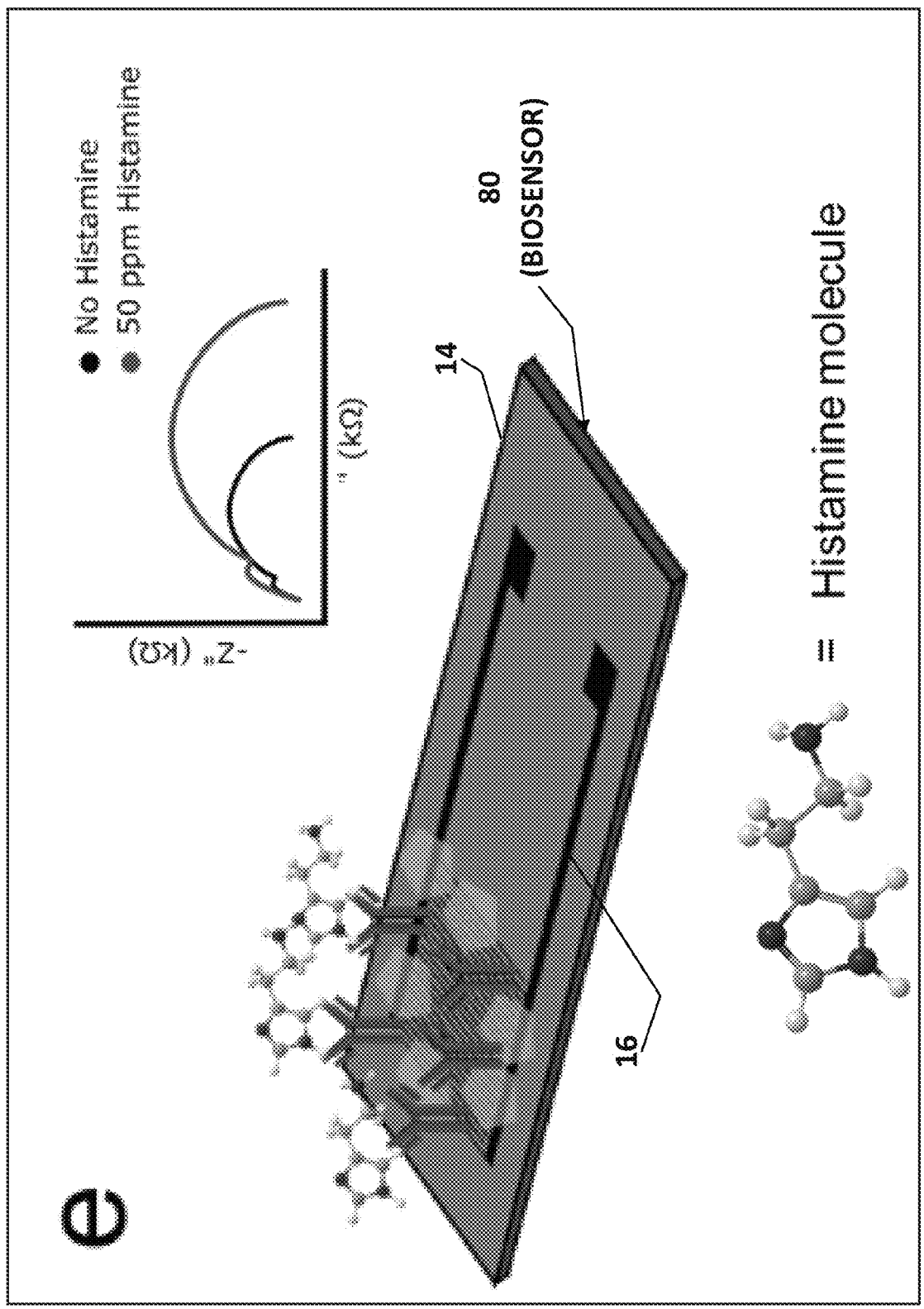

The AJP fabrication process consists of three main steps: graphene ink formulation, aerosol jet printing, and post-print baking (FIGS. 17A-C; see also FIGS. 17D-E). Graphene ink formulation starts with the liquid phase exfoliation of graphite powder in acetone using nitrocellulose as a stabilizing polymer. A powder of few-layer graphene nanosheets coated in nitrocellulose was obtained after processing the slurry of exfoliated graphite, and an aerosol jet printable ink was formulated from the graphene-nitrocellulose powder using a solvent system of 9:1 ethyl lactate:dibutyl phthalate. This ink was aerosol jet printed into interdigitated electrode patterns using optimized printing conditions at a print speed of 5 mm·s$^{-1}$. The printed devices were baked at 350° C. in air using a tube furnace to drive the decomposition of nitrocellulose into amorphous sp$^2$-bonded carbonaceous residue, which improves the mechanical properties of the graphene film as well as increases the electrical conductivity to >$10^4$ S·m$^{-1}$ [52, 53]. The devices were further annealed in $CO_2$ at 400° C. in order to enhance antibody binding with the graphene surface by promoting surface functionalization with carboxyl and carbonyl groups [54].

2.2. Image Analysis of the AJP Graphene IDE

The graphene film morphology and film thickness were characterized by optical microscopy, scanning electron microscopy (SEM), and atomic force microscopy (AFM) (FIGS. 18A-E). The AJP graphene device was patterned as an IDE containing 50 fingers (25 per each finger-comb side), each with a width of 40 µm, length of 7 mm, and inter-finger spacing of 100 µm (FIGS. 18A-B, D). This patterning resulted in a geometric surface area of 14 mm², with an electrochemical surface area of 8.01 mm², contributing to a total of 57% active sites with respect to the total geometric area of the IDE (see Supplemental Information FIGS. 22A-C). The graphene flakes showed a highly dense and aligned printed film that allows for efficient charge transfer across the material (FIG. 18C) [52]. A more efficient charge transfer process is desired for biosensing applications as affinity-based sensors rely on the change of surface chemistry, which is proportional to the available electrochemical surface area, due to target-capture probe binding and an associated change in the charge transfer behavior [55].

2.3. Electrical Characterization of the AJP Graphene IDE

The AJP process deposits graphene ink with smaller satellite droplets that diverge from the main stream beyond the focal point [56], generating aerosol printed lines with diffuse edges. The evaporation of the deposited graphene ink also exhibits a weak coffee-ring effect, resulting in a printed line morphology that possesses a depression in the center and taller edges as shown by AFM imaging (FIG. 18E). By averaging over the linewidth, the printed graphene film displayed a thickness of 63±6 nm with a surface roughness of 8±1 nm. AJP graphene printed features have a relatively low material consumption in comparison to other techniques that have shown similar printed line resolution since the AJP printed line thickness is significantly lower than previous reports (0.3-2 µm) [30, 56, 57]. Despite the exceptionally thin nature of the AJP graphene printed film, the electrochemical performance of these devices remains exemplary due to the high percentage of electrochemically active sites and resulting high sensitivity for biosensing (as will be shown in detail below).

It is also important for a functioning IDE that the electrode fingers are not shorted, which is a potential concern of the satellite droplet overspray of the graphene ink. Hence, the devices were tested for any electrical shorting before use. The AJP graphene IDEs showed a sheet resistance of 1.5±0.3 kΩ/sq that is similar to solution-phase printed and annealed graphene inks based on cellulose-based binders that have been previously employed for inkjet printing (0.2 kΩ/sq.-1.1 kΩ/sq.), but higher than thicker printed graphene films [51, 58, 59] that have been fabricated through spin coating (50-90 Ω/sq.) [25, 60] or screen printing (1 Ω/sq.) [61] or printed without binders through polymer casting (0.2 kΩ/sq.) [62], stamping (8 Ω/sq.) [63], or rolling compression (3.8 Ω/sq.) [64]. The higher sheet resistance for the AJP graphene IDEs is expected to the low thickness (63 nm) compared to the aforementioned techniques: 150 nm-7 µm for inkjet printing [51, 58, 59], 0.8 µm for spin coating [25], and 2.5 µm for screen printing [61]. Nevertheless, the sheet resistances of the AJP graphene IDEs are sufficiently low for effective electrochemical sensing (as will be shown in detail below).

2.4. Spectral Characterization of the AJP Graphene IDE

The AJP graphene IDEs were further characterized by Raman spectroscopy and X-ray photoelectron spectroscopy (XPS). As shown in FIG. 19A, the characteristic Raman D peak was observed at ~1311 cm$^{-1}$, which is associated with the presence of defects in the hexagonal graphitic layers [65]. Similarly, a G peak that is indicative of sp²-bonded carbon atoms in graphene was observed at ~1579 cm$^{-1}$ [65]. Meanwhile, the 2D band generated by the double resonance electron-phonon scattering characteristic of graphene [66] was observed at ~2614 cm$^{-1}$. In addition to the graphene bands, polyimide bands were observed at ~1392 cm$^{-1}$ (corresponding to C—N stretching vibration of the imide system), ~1610 cm$^{-1}$ (related to C=C stretching vibration of the 1,4-disubstituted phenyl ring), and ~1784 cm$^{-1}$ (related to C=O stretching vibration of imide) [67-69]. The presence of polyimide bands on the graphene spectra (see FIG. 23) is expected since the Raman laser penetrates through the thin graphene film. The intensity ratio of $I_{2D}/I_G$ peaks of graphene spectra was measured to be 0.8±0.2, which indicates a multilayer graphene film as expected [70]. Likewise, the intensity ratio of $I_D/I_G$, which provides a measure of the presence of defects on the graphene surface, was measured to be 1.4±0.1 [71, 72]. This defect level enhances heterogeneous charge transfer during electrochemical measurements and also facilitates the attachment of biorecognition agents, such as antibodies, required for the functionalization of the sensor [1, 50, 73].

Further characterization of the AJP graphene-based IDEs was performed with XPS to estimate the concentration of the functional groups present. Based on FIG. 19B, the graphene surface possesses both sp² and sp³ bonded carbon atoms, represented by the peaks corresponding to binding energies of 284.6 eV and 285.6 eV with relative concentrations of 46.4% and 19.6%, respectively. In addition to carbon-carbon bonds, oxygen functional groups such as C—O—C at 286.5 eV (16.3%), carbonyl groups (C=O) at 287.5 eV (5.6%), and carboxyl groups (O—C=O) at 289.1 eV (6%) were observed [74]. The $CO_2$ annealing of AJP graphene-based electrodes is associated with the enhancement of oxygen-containing moieties, such as carbonyl and carboxyl, on the graphene surface [54]. Since antibodies are covalently attached to graphene via EDC/NHS esterification reaction, the presence of carbonyl and carboxyl moieties is crucial for device functionalization [75].

2.5. Electrochemical Sensing of Histamine with the AJP Graphene IDE Biosensor

Next, the AJP graphene IDEs were functionalized with histamine antibody via EDC/NHS covalent binding chemistry (see Methods, and AFM images in FIGS. 24A-B) prior to subsequent histamine sensing. From the obtained Nyquist plots (FIG. 10A), a consistent increase in the charge transfer resistance ($R_{ct}$) values (calculated as the diameter of the semi-circular shaped portion of the plot) was observed with increasing histamine concentration. During incubation, the histamine molecules bind to the antibody epitope creating an insulating layer on the electrode. As more histamine molecules are bound to the antibodies on the electrode, the insulating layer increases, decreasing the effectiveness of electron transfer between the electrolyte solution and the electrode, resulting in the increase of $R_{ct}$ values [76]. A calibration plot was obtained by normalizing the $R_{ct}$ with respect to the $R_{ct}$ value measured for zero concentration of histamine in the buffer solution (PBS), as shown in FIG. 20B. The AJP graphene-based biosensor presented a linear sensing range from 6.25 to 100 ppm ($p_{model}$=0.000, $p_{lack-of-fit}$=0.666, $R^2$=0.823), a limit of detection of 2.52±0.92 ppm, and a sensitivity of 2.9±1.2 kΩ·decade$^{-1}$ (FIG. 20B). This high sensitivity and low detection limit can be attributed to the high surface area, charge transfer efficiency, faster steady state establishment, and signal-to-noise ratio of the comb-like structure associated with electrochemical IDEs [25, 77, 78].

Next, the AJP graphene-based biosensor was evaluated in a real biological matrix (i.e., freshly prepared fish broth). Again, the increase of histamine concentration in spiked fish broth resulted in an increase of $R_{ct}$, as observed from the Nyquist plots in FIG. 20C and the calibration plot in FIG. 20D. Based on the calibration plot, the dynamic linear sensing range for histamine detection in fish broth is 6.25 to 200 ppm ($p_{model}$=0.000, $p_{lack-of-fit}$=0.955, $R^2$=0.884). A limit of detection of 3.41±1.42 ppm was observed for fish broth samples, which is similar to the detection limit obtained in buffer (p=0.315; α=0.05). In addition, the sensitivity of the AJP graphene-based biosensor in fish broth (4.5±1.6 kΩ·decade$^{-1}$) was comparable to the sensitivity observed in buffer (p=0.141; α=0.05). These results emphasize the versatility and stability of the AJP graphene-based biosensor even when used in chemically complex samples such as fish broth, which is rich in amino acids, lipids, vitamins, and minerals [79].

Lower sensing ranges and limits of detection have been demonstrated in the literature using other sensing devices that also require much longer response times, such as electrochemiluminescence with a sensing range between 0.01 ppm and 1 ppm (overall response time: 8.5 hours) [80]; quartz crystal microbalance with a sensing range between 0.11 ppb and 11.22 ppm (overall response time: 4.5 hours) [81]; and photoluminescent quantum dots between 10.7 ppm and 63.36 ppm (overall response time: 67 min) [82]. However, these devices either present sensing ranges below the established FDA or European Food Safety Authority (EFSA) toxicity limits, which could lead to unnecessary rejection of fish samples, or they require sophisticated equipment, pre-labeling, and/or optical measurements, which are generally not suitable for in-field food sensing that requires rapid and low-cost sensor materials and operation in turbid field samples. A recent study by Vanegas et al [83] reported an in-field electrochemical biosensor comprised of laser induced graphene that was capable of monitoring total biogenic amines in fish samples with a sensing range of 5.56 to 177.84 ppm and with a detection limit of 1.29 ppm. However, this graphene-based biosensor required functionalization with metallic copper microparticles and enzymes, was not specific to histamine (a single type of biogenic amine) and required a 60-min current polarization prior to detection. Similarly, Gumpu et al. [84] reported an enzymatic electrochemical histamine biosensor consisting of a glassy carbon electrode modified with polyaniline and ceria nanoparticles and showed a linear sensing range of 50-117 ppm. In contrast, the sensing range presented by the AJP graphene-based biosensor in fish broth confirmed its capacity for efficient detection of histamine that is compliant with FDA recommended levels (50 ppm) and EFSA (100 ppm) [85, 86] with an overall response time of 33 min (including incubation of electrode with the sample) and negligible interference from turbid biological sample conditions. According to the FDA, since there is a large variability of histamine distribution throughout fish, it is possible to find 50 ppm in certain tissues, while other parts of the same fish may present 500 ppm or more [85, 87]. Therefore, the detection of histamine levels around 50 ppm are critical to determine whether a fish is safe for consumption while avoiding both food poisoning and wastage.

2.6. Non-Specific Adsorption Testing with the AJP Graphene IDE Biosensor

The AJP IDE biosensor was also tested in complex media consisting of large proteins in order to analyze the resiliency of the biosensor towards non-specific adsorption (FIG. 21). The interferent proteins selected herein (i.e., bovine serum albumin (BSA), goat serum (GS), and whey protein (WP)) are either frequently applied as blocking agents for biosensor devices due to their large size and effectiveness in covering surfaces or commonly occur in food products [88, 89]. Non-specific adsorption of such large interferent proteins could possibly result in false positives and surface fouling, which would affect the effectiveness of the biosensor [90]. Hence, it is important to determine their possible non-specific adsorption on the sensor. A concentration of 50 ppm was used for the interfering proteins to determine their effect on detecting 50 ppm of histamine, which is the minimum toxic level recommended by the FDA [85]. For all the interfering proteins, the percentage change of $R_{ct}$ (less than 10%) was significantly smaller (p=0.000, α=0.05) when compared to a change of 48% for the same concentration of histamine. Furthermore, the percentage change of $R_{ct}$ by interfering proteins was lower than the selectivity test signal changes established by similar studies [91, 92]. These results indicate that large protein molecules do not have a significant effect on the sensor function, such as amplifying the blocking effect on the immunosensor or exhibiting cross-reactivity with the histamine antibody.

3. Conclusions

In this work, an AJP graphene-based histamine biosensor was developed. The printed graphene IDE featured low-cost, one-step writing with high resolution fingers of 40 μm width and nanometer-scale thickness of 63 nm. AJP-printed IDEs were functionalized with monoclonal histamine antibody via EDC/NHS chemistry. Histamine detection was tested in buffer and in fish broth to validate the sensor performance. The AJP graphene biosensor platform could detect histamine in PBS and fish broth over toxicologically relevant ranges of 6.25 to 100 ppm and 6.25 to 200 ppm, respectively, with similar detection limits of 2.52 ppm and 3.41 ppm, respectively. The sensors also showed a quick response time of only 33 min without the need for pre-labeling and pre-treatment of the acquired fish sample. Furthermore, the biosensor sensitivity was not significantly affected by the non-specific adsorption of large protein molecules that are commonly found in food samples and used as blocking agents. Such a facile and rapid biosensor can thus find applications in food processing facilities, import and export ports, and supermarkets where continuous on-site monitoring of food samples is essential to determine and maintain the quality of every food item sold. This on-site testing will eliminate the need for sending the food samples for laboratory testing, which requires additional handling steps, increases time and cost to histamine analysis, and consequently increases the risk of foodborne illnesses and food wastage.

The AJP graphene IDE platform developed here can likely also be used in other biosensing applications where rapid monitoring of target molecules is desired, as the sample pre-treatment is eliminated using the developed immunosensing protocol. Apart from sensing small allergen molecules such as histamine, the immunosensor could be used to detect various targets such as cells and protein biomarkers. By switching the antibody immobilized on the sensor platform to one that is specific towards the detection of suitable biological target species, the sensor can further cater to specific applications. Some examples include food pathogens (*Salmonella* spp.) [93], fatal human diseases (cancer, HIV) [94, 95] or animal or plant diseases (avian influenza, *Citrus tristeza*) [96, 97]. Additionally, aerosol jet printing for manufacturing graphene IDEs is a highly scalable process in which a variety of metallic and non-metallic materials (i.e., graphene, silver) can be formulated into inks and printed in high-resolution patterns on substrates with different degrees of flexibility such as polyimide or silicon [29, 98] without employing expensive patterning techniques such as photolithography. Such high-resolution printed electrochemical devices can be implemented for energy harvesting [99] or for producing supercapacitors [100] apart from biosensing, thus widening their scope of applications.

4. Methods

4.1. Materials

Graphite powder (grade 3061) was purchased from Asbury Graphite Mills (Asbury, NJ). Nitrocellulose was purchase from Scientific Polymer (Ontario, NY, USA). Acetone, ethyl lactate, dibutyl phthalate, N-(3-dimethylaminopropyl)-N'-ethylcarbodiimide (EDC), N-hydroxysuccinimide (NHS), ethanolamine, 2-(N-morpholino) ethanesulfonic acid (MES buffer), histamine ≥97.0%, potassium hexacyanoferrate (II) trihydrate, potassium ferricyanide, and goat serum were purchased from Millipore Sigma (Saint Louis, MO, USA). Potassium chloride was purchased from Fisher Scientific (Hampton, NH, USA). Superblock™ buffer was purchased from Thermo Fisher (Waltham, MA, USA). Whey protein was purchased from Equate (Walmart, Bentonville, AR, USA). Bovine serum albumin (BSA) was purchased from VWR International (Solon, OH, USA). Phosphate buffer saline was purchased from Alfa Aesar (Tewksbury, MA, USA). Mouse anti-histamine monoclonal antibody (Cat. No. MAB5408) was purchased from EMD Millipore (Burlington, MA, USA)

4.2. Graphene Ink Formulation

Graphene ink was prepared as previously described by Secor et al. [52]. First, graphite powder was mixed with nitrocellulose (1:1) and dispersed in acetone. The suspension was shear mixed for 4 hours at 10,230 rpm to promote the exfoliation of graphite flakes. Then, the suspension was centrifuged for 15 min at 4600 rcf, followed by 20 min at 6650 rcf, and the supernatant was collected. The collected supernatant was flocculated with aqueous NaCl solution (0.04 $g \cdot mL^{-1}$) and centrifuged for 6 min at 10,000 rcf. The obtained pellet was washed with DI (distilled) water, dried under a 60 W lamp, and crushed to form a powder. The graphene-based powder (30 $mg \cdot mL^{-1}$) was dispersed in a 1:9 (v/v) mixture of dibutyl phthalate and ethyl lactate in bath sonication (110 W, 40 kHz) for 6 hours, thus forming the graphene ink. The prepared graphene ink was filtered through a 3.1 µm membrane for printing.

4.3. Aerosol Jet Printing

The graphene-based ink was aerosol jet printed in an interdigitated electrode (IDE) pattern on top of a polyimide (Kapton®, Dupont, MI, USA) substrate using an Optomec AJ200 Printer (Albuquerque, NM, USA). The substrate was maintained at 60° C. in order to reduce the coffee ring effect by cancelling the evaporation driven material flow using geometric surface tension material flow [101], and the printing speed was adjusted to 5 $mm \cdot s^{-1}$ to print the devices with minimum thickness and appropriate electrical conductivity [34]. During the printing process, the sheath flow rates were kept between 40-60 sccm, with a carrier flow rate between 15-45 sccm. The flow rates were optimized at the beginning of every print session to deposit continuous lines presenting 40 µm width and minimal overspray, which were continually tuned throughout the printing process. Nitrogen was used as both sheath and carrier gas. The graphene IDEs were printed in a single pass (1 layer), which is sufficient to fabricate high quality conductive electrodes for electrochemical sensing, as we have shown previously [52]. After printing, the IDEs were heat treated in air in a box furnace (Lindberg Blue M, Thermo Scientific, Waltham, MA, USA) for 30 min at 350° C. to evaporate any residual solvent and to pyrolyze the nitrocellulose. At 350° C., the maximum improvement to the electrical properties of the graphene film is obtained due to the decomposition of nitrocellulose into a carbonaceous $sp^2$-bonded residue [52]. Finally, printed devices were carbon dioxide annealed in a tube furnace (OTF-1200X, NM Corp, Richmond, CA, USA) at 400° C. for 2 hours to increase the amount of carboxyl groups on the graphene surface.

4.4. Functionalization

Graphene-based IDEs were functionalized using 0.4 M EDC and 0.1 M NHS prepared in 0.1 M MES buffer (pH 6.0) for 1 hour at room temperature. Then, the IDEs were incubated overnight with mouse anti-histamine monoclonal antibody solution (1:150) in sterile 1×PBS. After the incubation, 1 M ethanolamine was used to quench the unreacted EDC/NHS for 20 min, followed by blocking with Superblock™ buffer for 20 min to eliminate any non-specific binding of histamine.

4.5. Scanning Electron Microscopy

Scanning electron microscopy (SEM) images of the AJP graphene-based devices were obtained using a FEI Quanta 250 FE-SEM (ThermoFisher Scientific, OR, USA). Initially, the samples were coated with a 2-nm layer of Iridium using a turbo pump sputter coater. Then, the images were acquired using a working distance of ~10 mm, spot size of 3.0, and 10 kV of accelerating potential.

4.6. Atomic Force Microscopy

Atomic force microscopy (AFM) images were acquired using a Dimension Icon Scanning Probe Microscope (Bruker, Santa Barbara, CA, USA) in air. Tapping mode was used to obtain images of the IDE surface before and after the immobilization of antibodies (see Supplemental Information FIGS. 24A-B). The IDE finger height measurements were carried out in Peak Force Tapping mode using ScanAsyst. The probes used were model ScanAsyst-Air (Bruker, Santa Barbara, CA, USA) or TESPA probes (Bruker, Santa Barbara, CA, USA). AFM images were post processed using plane-fitting (second order) and/or flattening (zeroth order) within the Nanoscope software.

4.7. Raman Spectroscopy

Raman spectra of the AJP graphene-based electrodes were collected using an XploRa Plus confocal Raman upright microscope equipped with a Synapse EMCCD camera (Horiba Scientific, JY, France). A 785-nm laser excitation source (5 mW at the sample) and a 100× air objective (0.9 numerical aperture, LMPlan N, Olympus) were used to collect the Raman signal under ambient laboratory conditions. The spectra were collected with a 600 $grooves \cdot mm^{-1}$ grating, and all reported spectra were averaged over six replicates, each with 60 s acquisition time and 3 accumulations. Igor Pro 6.36 (Wavemetrics, Inc., Lake Oswego, OR, USA) scientific analysis and graphing software was used to analyze the Raman data. A Lorentzian distribution with linear baseline correction was utilized to fit the data in order to extract peak intensity (height). $I_D/I_G$ and $I_{2D}/I_G$ reported values correspond to an average of 6 spectra.

4.8. X-Ray Photoelectron Spectroscopy

X-ray photoelectron spectroscopy (XPS) evaluation was carried out using a Kratos Amicus/ESCA 3400 instrument. The sample was irradiated with 240 W unmonochromated Al$K\alpha$ x-rays, and photoelectrons emitted at 0° from the surface normal were energy analyzed using a DuPont type analyzer. The pass energy was set at 150 eV, and a Shirley baseline was removed from all reported spectra. Raw data files were processed using CasaXPS software (v 2.3.19).

4.9. Electrochemical Measurement

Electrochemical measurements were carried out using a two-electrode set up on a CH Instruments potentiostat station (CHI 7081E). All measurements were conducted in 5 mM Fe(CN)$_6^{3-}$/Fe(CN)$_6^{4-}$ ferri/ferrocyanide (1:1) redox probe with 0.1 M KCl dissolved in 1×PBS. Electrochemical impedance spectroscopy (EIS) measurements were carried out using a frequency range of 0.1 Hz-100 kHz with an AC voltage amplitude of 10 mV and no DC bias. Nyquist plots were used to determine the charge transfer resistance ($R_{ct}$), which is the resistance for charge transfer across the electrode-electrolyte interface.

4.10. Histamine Sensing

Histamine standard solutions were prepared in 1×PBS in a range between 6.25 and 800 ppm (1 ppm=1 mg L$^{-1}$=9 µM). IDEs were incubated with 100 µL of each standard solution for 30 min at 50 rpm to allow histamine to bind to the immobilized antibody on the IDE surface. Between each measurement, the electrodes were washed with 100 µL of 1×PBS thrice to remove unbound histamine molecules. Histamine calibration plots in 1×PBS were obtained by measuring the $R_{ct}$ for each successive concentration using the same EIS parameters as previously described.

4.11. Fish Broth Sensing

A homogeneous fish broth was initially prepared by blending (1000 W, 30 s) 25 g of fresh yellowfin tuna (*Thunnus albacares*) filet (Anova Food, LLC, San Diego, CA, USA) with 500 mL of sterilized 1×PBS. Then, the fish broth was filtered through a Whatman grade 1 qualitative filter paper (11.0 µm) (Millipore Sigma, Saint Louis, MO, USA) to remove the large particles, followed by a 0.45 µm syringe filter (Corning, Corning, NY, USA) and stored at 4° C. until use. Measurements were carried out as described on section 4.10.

4.12. Non-Specific Adsorption Test

Bovine serum albumine (BSA), goat serum (GS), and whey protein (WP) were used as interferents to test the affinity of the AJP graphene-based biosensor to non-specific interactions. The biosensor was incubated with solutions containing 50 ppm (in 1×PBS) of each interferent in the same conditions of histamine (30 min). Then, the EIS measurements were recorded, and the percentage change of $R_{ct}$ was calculated for each one of the interferents.

4.13. Data Analysis

A completely randomized design was used in this study and the results were reported as meant standard deviation. Calibration curves and non-specific adsorption test results were obtained by performing at least 3 independent experiments. Data analysis was performed using JMP Pro statistical software (version 15, SAS, Cary, NC). Qualitative comparisons were carried out using t-test with confidence level of 95%. Regression analysis with confidence level of 95% was performed to determine the linear sensing range and the functional correspondence among quantitative variables. The limit of detection for the developed biosensors was calculated using three times the standard deviation (3σ) of the zero-concentration measurement [102, 103].

References for Embodiment 3

[1] Pumera M 2011 Graphene in biosensing *Materials today* 14 308-15

[2] Hondred J A, Breger J C, Alves N J, Trammell S A, Walper S A, Medintz I L and Claussen J C 2018 Printed graphene electrochemical biosensors fabricated by inkjet maskless lithography for rapid and sensitive detection of organophosphates *ACS applied materials & interfaces* 10 11125-34

[3] Raccichini R, Varzi A, Passerini S and Scrosati B 2015 The role of graphene for electrochemical energy storage *Nat. Mater.* 14 271

[4] Yu H K, Balasubramanian K, Kim K, Lee J-L, Maiti M, Ropers C, Krieg J, Kern K and Wodtke A M 2014 Chemical vapor deposition of graphene on a "peeled-off" epitaxial cu (111) foil: A simple approach to improved properties *ACS nano* 8 8636-43

[5] Lin Y-M, Dimitrakopoulos C, Jenkins K A, Farmer D B, Chiu H-Y, Grill A and Avouris P 2010 100-GHz transistors from wafer-scale epitaxial graphene *Science* 327 662-

[6] Russo P, Hu A, Compagnini G, Duley W W and Zhou N Y 2014 Femtosecond laser ablation of highly oriented pyrolytic graphite: a green route for large-scale production of porous graphene and graphene quantum dots *Nanoscale* 6 2381-9

[7] Wu Z-S, Ren W, Gao L, Liu B, Jiang C and Cheng H-M 2009 Synthesis of high-quality graphene with a predetermined number of layers *Carbon* 47 493-9

[8] Liang X, Sperling B A, Calizo I, Cheng G, Hacker C A, Zhang Q, Obeng Y, Yan K, Peng H and Li Q 2011 Toward clean and crackless transfer of graphene *ACS nano* 5 9144-53

[9] Allen M J, Tung V C, Gomez L, Xu Z, Chen L M, Nelson K S, Zhou C, Kaner R B and Yang Y 2009 Soft transfer printing of chemically converted graphene *Advanced Materials* 21 2098-102

[10] Lim W S, Kim Y Y, Kim H, Jang S, Kwon N, Park B J, Ahn J-H, Chung I, Hong B H and Yeom G Y 2012 Atomic layer etching of graphene for full graphene device fabrication *Carbon* 50 429-35

[11] Bell D C, Lemme M C, Stern L A, Williams J R and Marcus C M 2009 Precision cutting and patterning of graphene with helium ions *Nanotechnology* 20 455301

[12] Bai J, Zhong X, Jiang S, Huang Y and Duan X 2010 Graphene nanomesh *Nature nanotechnology* 5 190

[13] Gao S, Zang P, Dang L, Xu H, Shi F, Liu Z and Lei Z 2016 Extraordinarily high-rate capability of polyaniline nanorod arrays on graphene nanomesh *Journal of Power Sources* 304 111-8

[14] Duan X, Mu L, Sawtelle S D, Rajan N K, Han Z, Wang Y, Qu H and Reed M A 2015 Functionalized Polyelectrolytes Assembling on Nano-BioFETs for Biosensing Applications *Advanced Functional Materials* 25 2279-86

[15] Kim B-Y, Sohn I-y, Lee D, Han G S, Lee W-I, Jung H S and Lee N-E 2015 Ultrarapid and ultrasensitive electrical detection of proteins in a three-dimensional biosensor with high capture efficiency *Nanoscale* 7 9844-51

[16] Medina-Sánchez M, Martínez-Domingo C, Ramon E and Merkoçi A 2014 An Inkjet-Printed Field-Effect Transistor for Label-Free Biosensing *Advanced Functional Materials* 24 6291-302

[17] Dua V, Surwade S P, Ammu S, Agnihotra S R, Jain S, Roberts K E, Park S, Ruoff R S and Manohar S K 2010 All-organic vapor sensor using inkjet-printed reduced graphene oxide *Angewandte Chemie International Edition* 49 2154-7

[18] Tölle F J, Fabritius M and Mülhaupt R 2012 Emulsifier-Free Graphene Dispersions with High Graphene Content for Printed Electronics and Freestanding Graphene Films *Advanced Functional Materials* 22 1136-44

[19] Erath D, Filipović A, Retzlaff M, Goetz A K, Clement F, Biro D and Preu R 2010 Advanced screen printing technique for high definition front side metallization of crystalline silicon solar cells *Solar energy materials and solar cells* 94 57-61

[20] Reese C, Roberts M, Ling M-m and Bao Z 2004 Organic thin film transistors *Materials today* 7 20-7

[21] Krebs F C, Fyenbo J and Jørgensen M 2010 Product integration of compact roll-to-roll processed polymer solar cell modules: methods and manufacture using flexographic printing, slot-die coating and rotary screen printing *Journal of Materials Chemistry* 20

[22] Lamas-Ardisana P J, Martinez-Paredes G, Anorga L and Grande H J 2018 Glucose biosensor based on disposable electrochemical paper-based transducers fully fabricated by screen-printing *Biosens Bioelectron* 109 8-12

[23] Hyun W J, Secor E B, Hersam M C, Frisbie C D and Francis L F 2015 High-resolution patterning of graphene by screen printing with a silicon stencil for highly flexible printed electronics *Adv. Mater.* 27 109-15

[24] Zhang L, Liu H, Zhao Y, Sun X, Wen Y, Guo Y, Gao X, Di C a, Yu G and Liu Y 2012 Inkjet printing high-resolution, large-area graphene patterns by coffee-ring lithography *Adv. Mater.* 24 436-40

[25] Hondred J A, Stromberg L R, Mosher C L and Claussen J C 2017 High-Resolution Graphene Films for Electrochemical Sensing via Inkjet Maskless Lithography *ACS nano* 11 9836-45

[26] Cai F, Chang Y-h, Wang K, Khan W T, Pavlidis S and Papapolymerou J 2014 High resolution aerosol jet printing of D-band printed transmission lines on flexible LCP substrate. In: *2014 IEEE MTT-S International Microwave Symposium (IMS2014)*: IEEE) pp 1-3

[27] Jabari E and Toyserkani E 2015 Micro-scale aerosol-jet printing of graphene interconnects *Carbon* 91 321-9

[28] Binder S, Glatthaar M and Rädlein E 2014 Analytical investigation of aerosol jet printing *Aerosol Science and Technology* 48 924-9

[29] Mahajan A, Frisbie C D and Francis L F 2013 Optimization of aerosol jet printing for high-resolution, high-aspect ratio silver lines *ACS Appl. Mater. Interfaces* 5 4856-64

[30] Deiner L J and Reitz T L 2017 Inkjet and aerosol jet printing of electrochemical devices for energy conversion and storage *Adv. Eng. Mater.* 19 1600878

[31] Cantù E, Tonello S, Abate G, Uberti D, Sardini E and Serpelloni M 2018 Aerosol Jet Printed 3D Electrochemical Sensors for Protein Detection *Sensors* 18 3719

[32] Di Novo N G, Cantù E, Tonello S, Sardini E and Serpelloni M 2019 Support-material-free microfluidics on an electrochemical sensors platform by aerosol jet printing *Sensors* 19 1842

[33] Marziano M, Tonello S, Cantù E, Abate G, Vezzoli M, Rungratanawanich W, Serpelloni M, Lopomo N, Memo M and Sardini E 2019 Monitoring Caco-2 to enterocyte-like cells differentiation by means of electric impedance analysis on printed sensors *Biochimica et Biophysica Acta (BBA)—General Subjects* 1863 893-902

[34] Parate K, Rangnekar S V, Jing D, Mendivelso-Perez D L, Ding S, Secor E B, Smith E A, Hostetter J M, Hersam M C and Claussen J C 2020 Aerosol-Jet-Printed Graphene Immunosensor for Label-Free Cytokine Monitoring in Serum *ACS Applied Materials & Interfaces*

[35] Biji K B, Ravishankar C N, Venkateswarlu R, Mohan C O and Gopal T K S 2016 Biogenic amines in seafood: a review *J Food Sci Technol* 53 2210-8

[36] Hungerford J M 2010 Scombroid poisoning: A review *Toxicon* 56 231-43

[37] AOAC 1977 OMA 977.13, Histamine in seafood: fluorometric method. Sec. 35.1.32. In: Cunniff, P. A. (Ed.), Official Methods of Analysis of AOAC Int., sixteenth ed. AOAC Int., Gaithersburg, MD, pp. 6-17. http://www.aoac.org/aoac_prod_imis/AOAC_Docs/OMA/977_13aoacmethod.pdf.

[38] Chen R, Deng Y, Yang L, Wang J and Xu F 2016 Determination of Histamine by High-Performance Liquid Chromatography After Precolumn Derivatization with o-Phthalaldehyde-Sulfite *Journal of Chromatographic Science* 54 547-53

[39] Tan A, Zhao Y, Sivashanmugan K, Squire K and Wang A X 2019 Quantitative TLC-SERS detection of histamine in seafood with support vector machine analysis *Food Control* 103 111-8

[40] Kim K-Y, Kwon H-J, Cho S-H, Nam M and Kim C-W 2019 Development and validation of a highly sensitive LC-MS/MS method for in vitro measurement of histamine concentration *Journal of Pharmaceutical and Biomedical Analysts* 172 33-41

[41] Serrar D, Brebant R, Bruneau S and Denoyel G A 1995 The development of a monoclonal antibody-based ELISA for the determination of histamine in food: application to fishery products and comparison with the HPLC assay *Food Chemistry* 54 85-91

[42] Peeters M, Troost F J, Mingels R H G, Welsch T, van Grinsven B, Vranken T, Ingebrandt S, Thoelen R, Cleij T J and Wagner P 2013 Impedimetric Detection of Histamine in Bowel Fluids Using Synthetic Receptors with pH-Optimized Binding Characteristics *Analytical Chemistry* 85 1475-83

[43] Carralero V, González-Cortés A, Yáñez-Sedeño P and Pingarron J 2005 Pulsed amperometric detection of histamine at glassy carbon electrodes modified with gold nanoparticles *Electroanalysis: An International Journal Devoted to Fundamental and Practical Aspects of Electroanalysis* 17 289-97

[44] Gajjala R K R and Palathedath S K 2018 Cu@ Pd core-shell nanostructures for highly sensitive and selective amperometric analysis of histamine *Biosensors and Bioelectronics* 102 242-6

[45] Stojanović Z S, Mehmeti E, Kalcher K, Guzsvány V and Stanković D M 2016 SWCNT-modified carbon paste electrode as an electrochemical sensor for histamine determination in alcoholic beverages *Food analytical methods* 9 2701-10

[46] Yang M, Zhang J and Chen X 2015 Competitive electrochemical immunosensor for the detection of histamine based on horseradish peroxidase initiated deposition of insulating film *Journal of Electroanalytical Chemistry* 736 88-92

[47] Dong X-X, Yang J-Y, Luo L, Zhang Y-F, Mao C, Sun Y-M, Lei H-T, Shen Y-D, Beier R C and Xu Z-L 2017 Portable amperometric immunosensor for histamine detection using Prussian blue-chitosan-gold nanoparticle nanocomposite films *Biosensors and Bioelectronics* 98 305-9

[48] Yadav S, Nair S S, Sai V V R and Satija J 2019 Nanomaterials based optical and electrochemical sensing of histamine: Progress and perspectives *Food Research International* 119 99-109

[49] Bratov A, Ramón-Azcón J, Abramova N, Merlos A, Adrian J, Sánchez-Baeza F, Marco M-P and Domínguez C 2008 Three-dimensional interdigitated electrode array as a transducer for label-free biosensors *Biosensors and bioelectronics* 24 729-35

[50] Ding S, Das S R, Brownlee B J, Parate K, Davis T, Stromberg L R, Chan E K, Katz J, Iverson B D and Claussen J C 2018 CIP2A Immunosensor Comprised of Vertically-aligned Carbon Nanotube Interdigitated Electrodes Towards Point-of-Care Oral Cancer Screening *Biosensors and Bioelectronics*

[51] Secor E B, Prabhumirashi P L, Puntambekar K, Geier M L and Hersam M C 2013 Inkjet Printing of High Conductivity, Flexible Graphene Patterns *J Phys Chem Lett* 4 1347-51

[52] Secor E B, Gao T Z, Islam A E, Rao R, Wallace S G, Zhu J, Putz K W, Maruyama B and Hersam M C 2017 Enhanced Conductivity, Adhesion, and Environmental Stability of Printed Graphene Inks with Nitrocellulose *Chemistry of Materials* 29 2332-40

[53] Secor E B, Gao T Z, Dos Santos M H, Wallace S G, Putz K W and Hersam M C 2017 Combustion-assisted photonic annealing of printable graphene inks via exothermic binders *ACS applied materials & interfaces* 9 29418-23

[54] Bagri A, Mattevi C, Acik M, Chabal Y J, Chhowalla M and Shenoy V B 2010 Structural evolution during the reduction of chemically derived graphene oxide *Nature Chemistry* 2 581

[55] Kong F-Y, Xu M-T, Xu J-J and Chen H-Y 2011 A novel label-free electrochemical immunosensor for carcinoembryonic antigen based on gold nanoparticles-thionine-reduced graphene oxide nanocomposite film modified glassy carbon electrode *Talanta* 85 2620-5

[56] Seifert T, Sowade E, Roscher F, Wiemer M, Gessner T and Baumann R R 2015 Additive manufacturing technologies compared: morphology of deposits of silver ink using inkjet and aerosol jet printing *Industrial & Engineering Chemistry Research* 54 769-79

[57] Pech D, Brunet M, Taberna P-L, Simon P, Fabre N, Mesnilgrente F, Conédéra V and Durou H 2010 Elaboration of a microstructured inkjet-printed carbon electrochemical capacitor *Journal of Power Sources* 195 1266-9

[58] Das S R, Nian Q, Cargill A A, Hondred J A, Ding S, Saei M, Cheng G J and Claussen J C 2016 3D nanostructured inkjet printed graphene via UV-pulsed laser irradiation enables paper-based electronics and electrochemical devices *Nanoscale* 8 15870-9

[59] He Q, Das S R, Garland N T, Jing D, Hondred J A, Cargill A A, Ding S, Kannakaran C and Claussen J C 2017 Enabling Inkjet Printed Graphene for Ion Selective Electrodes with Postprint Thermal Annealing *ACS applied materials & interfaces* 9 12719-27

[60] Hondred J A, Medintz I L and Claussen J C 2019 Enhanced electrochemical biosensor and supercapacitor with 3D porous architectured graphene via salt impregnated inkjet maskless lithography *Nanoscale Horiz.* 4 735-46

[61] He P, Cao J, Ding H, Liu C, Neilson J, Li Z, Kinloch I A and Derby B 2019 Screen-Printing of a Highly Conductive Graphene Ink for Flexible Printed Electronics *ACS Appl. Mater. Interfaces* 11 32225-34

[62] Uz M, Jackson K, Donta M S, Jung J, Lentner M T, Hondred J A, Claussen J C and Mallapragada S K 2019 Fabrication of High-resolution Graphene-based Flexible electronics via polymer Casting *Sci. Rep.* 9 1-11

[63] Stromberg L R, Hondred J A, Sanborn D, Mendivelso-Perez D, Ramesh S, Rivero I V, Kogot J, Smith E, Gomes C and Claussen J C 2019 Stamped multilayer graphene laminates for disposable in-field electrodes: application to electrochemical sensing of hydrogen peroxide and glucose *Microchim. Acta* 186 533

[64] Huang X, Leng T, Zhang X, Chen J C, Chang K H, Geim A K, Novoselov K S and Hu Z 2015 Binder-free highly conductive graphene laminate for low cost printed radio frequency applications *Appl. Phys. Lett.* 106 203105

[65] Khan M, Yousaf A B, Chen M, Wei C, Wu X, Huang N, Qi Z and Li L 2016 Molybdenum sulfide/graphene-carbon nanotube nanocomposite material for electrocatalytic applications in hydrogen evolution reactions *Nano Research* 9 837-48

[66] Lee D S, Riedl C, Krauss B, von Klitzing K, Starke U and Smet J H 2008 Raman spectra of epitaxial graphene on SiC and of epitaxial graphene transferred to SiO2 *Nano letters* 8 4320-5

[67] Ge J J, Xue G, Li F, McCreight K W, Wang S Y, Harris F W, Cheng S Z, Zhuang X, Hong S C and Shen Y 1998 Surface studies of polyimide thin films via surface-enhanced Raman scattering and second harmonic generation *Macromol. Rapid Commun.* 19 619-23

[68] Ishida H, Wellinghoff S T, Baer E and Koenig J L 1980 Spectroscopic studies of poly [N, N'-bis (phenoxyphenyl) pyromellitimide]. 1. Structures of the polyimide and three model compounds *Macromolecules* 13 826-34

[69] Pethe R, Carlin C, Patterson H and Unertl W 1993 Effect of dose stoichiometry on the structure of vapor-deposited polyimide thin films *J. Mater. Res.* 8 3218-28

[70] Childres I, Jauregui L A, Park W, Cao H and Chen Y P 2013 *Raman spectroscopy of graphene and related materials* vol 1

[71] Cançado L G, Jorio A, Ferreira E M, Stavale F, Achete C, Capaz R, Moutinho M, Lombardo A, Kulmala T and Ferrari A C 2011 Quantifying defects in graphene via Raman spectroscopy at different excitation energies *Nano letters* 11 3190-6

[72] Knirsch K C, Englert J M, Dotzer C, Hauke F and Hirsch A 2013 Screening of the chemical reactivity of three different graphite sources using the formation of reductively alkylated graphene as a model reaction *Chemical Communications* 49 10811-3

[73] Teixeira S, Burwell G, Castaing A, Gonzalez D, Conlan R and Guy O 2014 Epitaxial graphene immunosensor for human chorionic gonadotropin *Sensors and Actuators B: Chemical* 190 723-9

[74] Che J, Shen L and Xiao Y 2010 A new approach to fabricate graphene nanosheets in organic medium: combination of reduction and dispersion *Journal of Materials Chemistry* 20 1722-7

[75] Chiu N-F, Fan S-Y, Yang C-D and Huang T-Y 2017 Carboxyl-functionalized graphene oxide composites as SPR biosensors with enhanced sensitivity for immunoaffinity detection *Biosensors and Bioelectronics* 89 370-6

[76] Yang F, Han J, Zhuo Y, Yang Z, Chai Y and Yuan R 2014 Highly sensitive impedimetric immunosensor based on single-walled carbon nanohorns as labels and bienzyme biocatalyzed precipitation as enhancer for cancer biomarker detection *Biosensors and Bioelectronics* 55 360-5

[77] Min J and Baeumner A J 2004 Characterization and Optimization of Interdigitated Ultramicroelectrode Arrays as Electrochemical Biosensor Transducers *Electroanalysis* 16 724-9

[78] Ohno R, Ohnuki H, Wang H, Yokoyama T, Endo H, Tsuya D and Izumi M 2013 Electrochemical impedance spectroscopy biosensor with interdigitated electrode for detection of human immunoglobulin A *Biosensors and Bioelectronics* 40 422-6

[79] Bosch A C, O'Neill B, Sigge G O, Kerwath S E and Hoffman L C 2016 Mercury accumulation in Yellowfin tuna (*Thunnus albacares*) with regards to muscle type, muscle position and fish size *Food Chemistry* 190 351-6

[80] An D, Chen Z, Zheng J, Chen S, Wang L and Su W 2016 Polyoxometalate functionalized tris (2, 2-bipyridyl)

dichlororuthenium (II) as the probe for electrochemiluminescence sensing of histamine *Food chemistry* 194 966-71

[81] Horemans F, Alenus J, Bongaers E, Weustenraed A, Thoelen R, Duchateau J, Lutsen L, Vanderzande D, Wagner P and Cleij T 2010 MIP-based sensor platforms for the detection of histamine in the nano- and micromolar range in aqueous media *Sensors and Actuators B: Chemical* 148 392-8

[82] Khan S, Carneiro L S, Vianna M S, Romani E C and Aucelio R Q 2017 Determination of histamine in tuna fish by photoluminescence sensing using thioglycolic acid modified CdTe quantum dots and cationic solid phase extraction *Journal of Luminescence* 182 71-8

[83] Vanegas D, Patiño L, Mendez C, Oliveira D, Torres A, Gomes C and McLamore E 2018 Laser Scribed Graphene Biosensor for Detection of Biogenic Amines in Food Samples Using Locally Sourced Materials *Biosensors* 8 42

[84] Gumpu M B, Nesakumar N, Sethuraman S, Krishnan U M and Rayappan J B B 2014 Development of electrochemical biosensor with ceria-PANI core-shell nano-interface for the detection of histamine *Sensors and Actuators B: Chemical* 199 330-8

[85] FDA 2019 Chapter 7: Scombrotoxin (Histamine) Formation. In: Fish and Fishery Products Hazards and Controls Guidance. 4th Edition. Food and Drug Administration. Available at: <https://www.fda.gov/media/80637/download>.

[86] EFSA 2015 Scientific and technical assistance on the evaluation of the temperature to be applied to pre-packed fishery products at retail level *EFSA Journal* 13 4162

[87] Keow C M, Bakar F A, Salleh A B, Heng L Y, Wagiran R and Bean L S 2007 An amperometric biosensor for the rapid assessment of histamine level in tiger prawn (*Penaeus monodon*) spoilage *Food chemistry* 105 1636-41

[88] de la Escosura-Muñiz A and Merkoçi A 2011 A nanochannel/nanoparticle-based filtering and sensing platform for direct detection of a cancer biomarker in blood *Small* 7 675-82

[89] Maurer S, Wabnitz G H, Kahle N A, Stegmaier S, Prior B, Giese T, Gaida M M, Samstag Y and Hänsch G M 2015 Tasting *Pseudomonas aeruginosa* biofilms: human neutrophils express the bitter receptor T2R38 as sensor for the quorum sensing molecule N-(3-oxododecanoyl)-l-homoserine lactone *Frontiers in immunology* 6 369

[90] Ahluwalia A, Giusto G and De Rossi D 1995 Nonspecific adsorption on antibody surfaces for immunosensing *Materials Science and Engineering: C* 3 267-71

[91] Farid S, Meshik X, Choi M, Mukherjee S, Lan Y, Parikh D, Poduri S, Baterdene U, Huang C-E and Wang Y Y 2015 Detection of Interferon gamma using graphene and aptamer based FET-like electrochemical biosensor *Biosensors and Bioelectronics* 71 294-9

[92] Lei Y-M, Xiao M-M, Li Y-T, Xu L, Zhang H, Zhang Z-Y and Zhang G-J 2017 Detection of heart failure-related biomarker in whole blood with graphene field effect transistor biosensor *Biosensors and Bioelectronics* 91 1-7

[93] Salam F and Tothill I E 2009 Detection of *Salmonella typhimurium* using an electrochemical immunosensor *Biosensors and Bioelectronics* 24 2630-6

[94] Carinelli S, Marti M, Alegret S and Pividori M I 2015 Biomarker detection of global infectious diseases based on magnetic particles *New biotechnol.* 32 521-32

[95] Du D, Zou Z, Shin Y, Wang J, Wu H, Engelhard M H, Liu J, Aksay I A and Lin Y 2010 Sensitive immunosensor for cancer biomarker based on dual signal amplification strategy of graphene sheets and multienzyme functionalized carbon nanospheres *Analytical chemistry* 82 2989-95

[96] Haji-Hashemi H, Norouzi P, Safarnejad M R and Ganjali M R 2017 Label-free electrochemical immunosensor for direct detection of *Citrus tristeza* virus using modified gold electrode *Sensors and Actuators B: Chemical* 244 211-6

[97] Heinze B C, Gamboa J R, Kim K, Song J-Y and Yoon J-Y 2010 Microfluidic immunosensor with integrated liquid core waveguides for sensitive Mie scattering detection of avian influenza antigens in a real biological matrix *Analytical and bioanalytical chemistry* 398 2693-700

[98] Hong K, Kim S H, Mahajan A and Frisbie C D 2014 Aerosol jet printed p- and n-type electrolyte-gated transistors with a variety of electrode materials: Exploring practical routes to printed electronics *ACS applied materials & interfaces* 6 18704-11

[99] Xiao L, Damien J, Luo J, Jang H D, Huang J and He Z 2012 Crumpled graphene particles for microbial fuel cell electrodes *J. Power Sources* 208 187-92

[100] Shao Y, El-Kady M F, Lin C W, Zhu G, Marsh K L, Hwang J Y, Zhang Q, Li Y, Wang H and Kaner R B 2016 3D freeze-casting of cellular graphene films for ultrahigh-power-density supercapacitors *Adv. Mater.* 28 6719-26

[101] Gupta A A, Bolduc A, Cloutier S G and Izquierdo R 2016 Aerosol Jet Printing for printed electronics rapid prototyping. In: 2016 *IEEE International Symposium on Circuits and systems (ISCAS)*: IEEE) pp 866-9

[102] McNaught A D and Wilkinson A 1997 *Compendium of Chemical terminology: IUPAC recommendations* (Oxford: Blackwell Scientific)

[103] Vanegas D C, Taguchi M, Chaturvedi P, Burrs S, Tan M, Yamaguchi H and McLamore E S 2014 A comparative study of carbon-platinum hybrid nanostructure architecture for amperometric biosensing *Analyst* 139 660-7

Aerosol-Jet-Printed Graphene Electrochemical Histamine Sensors for Food Safety Monitoring
Supplemental Information
Electrochemical Surface Area Calculation:

From the cyclic voltammogram (CV) of the aerosol jet printed (AJP) graphene interdigitated electrode (IDE) (FIG. 22A), the peak separation voltage varies between ~0.6 to 1.2 V. Hence, this system is irreversible ($\Delta E_p > 200$ mV) and first the charge transfer coefficient ($\alpha$) needs to be calculated [1]. The value of $\alpha$ can be calculated from the plot of peak voltages versus logarithm of scan rate (FIG. 22B). For anodic peak voltage, $\alpha$ can be determined from the slope of the line as $$\text{slope} = \frac{2.3\,RT}{(1-\alpha)nF}. \quad [1]$$

From the FIG. 22B, the regression equation obtained was $y = 224.16x + 1021.4$ with $R^2 = 0.96$, which yields an $\alpha = 0.74$. Next, the electrochemical surface area was calculated from the Randles-Ševčík equation and slope of the Randles-Ševčík plot (FIG. 22C) for anodic current using the equation: slope=$2.99 \times 10^5 \alpha^{1/2} A C_o D_o^{1/2}$ [2]. Here, $C_o$ is the concentration of redox probe (5 mM), $D_o$ is the diffusion coefficient of the redox probe ($7.2 \times 10^{-6}$ cm$^2 \cdot$s$^{-1}$), A is the electrochemical surface area of the electrode and the regression equation for the anodic peak current was obtained as $y = 2.76 \times 10^{-4} x + 1.48 \times 10^{-5}$ with $R^2 = 0.99$. The forward (anodic) peak current rather than cathodic peak current for the calculation was used due to the reduced amount of product formation that might hinder the reverse peak values of the CV [3]. The electrochemical surface area of the aerosol jet printed (AJP) interdigitated electrode (IDE) was calculated as 8.01 mm².

Raman Spectroscopy of Kapton® (Polyimide) Substrate:

Raman spectroscopy yields a plot as shown in FIG. 23, due to the large spot size (1 μm) of the laser as compared to the finger width (40 μm) of the AJP graphene IDE. The polyimide bands obtained are restricted to the first order region of graphene spectrum (D and G regions). The resulting background needs to be subtracted from the raw data in order to get the spectrum pertaining to graphene only.

Qualitative Analysis of Antibody Immobilization on AJP Graphene IDE:

The histamine antibody immobilized on the graphene IDE was characterized by AFM. As shown in the FIGS. 24A-B, the micrograph was recorded for an untreated graphene (FIG. 24A) and after the antibody was attached to the graphene via EDC/NHS chemistry (FIG. 24B). As the graphene surface is relatively uneven on the nanometer scale and the size (height) of antibody is only about 4 nm [4], the antibodies can be difficult to visualize against a rough background. Nevertheless, due to the antibody attachment, there is an overall increase in the rough texture of the electrode surface. The boxes indicate areas that show prominent texture development on FIG. 24B as compared to FIG. 24A due to antibody attachment. Furthermore, the change in roughness of the surface as analyzed by the AFM software, Nanoscope Analysis (v. 1.9), was 3.7 nm which correlates with the antibody height.

References for Supplementary Information for Embodiment 3

[1] Laviron E 1979 General expression of the linear potential sweep voltammogram in the case of diffusionless electrochemical systems *J. Electroanal. Chem. Interfacial Electrochem.* 101 19-28
[2] Bard A J, Faulkner L R, Leddy J and Zoski C G 1980 *Electrochemical methods: fundamentals and applications* vol 2: wiley New York)
[3] García-Miranda Ferrari A, Foster C, Kelly P, Brownson D and Banks C 2018 Determination of the electrochemical area of screen-printed electrochemical sensing platforms *Biosensors* 8 53
[4] Ierardi V, Ferrera F, Millo E, Damonte G, Filaci G and Valbusa U 2013 Bioactive surfaces for antibody-antigen complex detection by Atomic Force Microscopy. In: *Journal of Physics: Conference Series*: IOP Publishing) p 012001

VI. Options and Alternatives

A. Applications

Below are non-limiting examples of possible applications for aspects of the invention:
Printable inks
Printable electronic devices
Sensors
Biosensors
Point-of-care diagnostic devices
Wearable devices
Flexible electronics B. Composition The specific ink compositions in the examples are non-limiting. In particular we demonstrate that graphene-nitrocellulose powder was found to form a stable dispersion in 9:1 ethyl lactate:dibutyl phthalate cosolvent system and was amenable to consequent aerosol jet printing. Dibutyl phthalate has a boiling point of 340° C., so it prevents aerosol droplets from evaporating completely before deposition on the substrate. Dibutyl phthalate remains in the printed feature until subsequent baking, and its presence allows graphene nanosheets to "relax" into a flat morphology. Moreover, a graphene ink with 30 mg/mL solids loading was prepared and filtered through a 3.1 μm membrane prior to printing. A 2 mL aliquot of the graphene ink was pipetted into the ink vial of the printer and ultrasonically atomized.

C. Printing

The aerosol jet printing technique can be varied according to need or desire. Also, other printing methods are possible. The printer parameters required to aerosol jet print thin and continuous graphene ink with minimal satellite droplets are also unique to this work. More particularly, sheath flow rates of 40-60 sccm, carrier flow rates of 15-45 sccm, and printing speeds of approximately 5 mm/s were tuned to yield thin and continuous traces of graphene ink with minimal satellite droplets on the substrate (see FIGS. 22A-C). The fluid dynamics of the aerosol jet deposition process is shown in FIG. 17B. Such parameters are unique to aerosol printing graphene inks as opposed to printing other materials (e.g., metal organic inks, metallic nanoparticle inks, polymer-based inks). Details about aerosol printing can be found at Chou et al., US2014/0035995A1, published Feb. 6, 2014, Aerosol Jet Printable Metal Conductive Inks, Glass Coated Metal Conductive Inks And UV-Curable Dielectric Inks And Methods Of Preparing And Printing The Same; and King et al., US2012/0231576A1, published Sep. 13, 2012, Aerosol Jet® Printing System For Photovoltaic Applications, each of which is incorporated by reference herein.

D. Fabrication

Fabrication can be by well-known scalable techniques. Examples are mentioned in the examples. Those skilled in the art know how to apply such various techniques. Details about examples of additive scalable manufacturing, including printing and roll-to-roll processing can be found at El-Terry et al., WO2019005708A2, published Jan. 3, 2019 Methods And Systems For Enabling And Scheduling 3d Printing-Based Fabrication; and U.S. Government, Roll To Roll (R2R) Processing Technology Assessment, A Feb. 13, 2015_roll to roll mfg.pdf.

E. Other

Other envisioned examples would be covalently attaching to the surface of the graphene with a different biorecognition agent than an antibody such as an enzyme, aptamer, DNA strand, lectins, bacteria phage, for the selective sensing of different biological or chemical agents The aerosol printing patterns and functionalization schemes could be use for other sensing modalities such as optical and fluorescent sensing. For example antibodies could be tagged with fluorescent molecules on the surface of the graphene for fluorescent based sensing.

Printing of high resolution graphene lends itself towards making multiple sensors on a small substrate. This would enable multiplexed biosensing where multiple chemical or biological analytes could be monitored from a single test solution.

Sensing is not confined to medical applications but could be used to apply to applications involved with the environment, defense/security, food safety, etc.

The flexible nature of both the graphene circuits and the circuits functionalized with a biorecognition agent lends itself well for attachment and use on curved surface. For example, our next project is to attach this sensor inside of a small cylindrical implant that would fit inside the collagen of an ear of a cattle so that immune responses (IL-10 and IFN-gamma levels) could be monitored in real-time and more rapidly. Other examples of flexibility would be wearable biosensors on human appendages or for monitoring analytes on curved flow cells or in a pipeline.

What is claimed is:

1. A method of fabrication of graphene-based circuits on a substrate comprising:
    a. preparing a printable ink of pristine graphene flakes of graphene or graphene oxide exfoliated from graphite produced and dispersed in solvents from bulk synthesis solution processing in a stable dispersion in an ethyl lactate:dibutyl phthalate cosolvent system with a viscosity in the approximate range of 1-1,000 cP; and
    b. aerosol jet printing one or more patterns in one or more passes by scalable, high-throughput direct write additive manufacturing on a substrate using said printable ink without stenciling or photolithography, the printable ink allowing a line thickness from a range of line thicknesses that includes sub-100 nm thicknesses and a line width resolution from a range of line widths that includes sub-100 µm widths without pre- or post-patterning steps.

2. The method of claim 1 further comprising post-print annealing the circuit effective to convert electrochemically inactive printed graphene into electrochemically active graphene.

3. The method of claim 2 wherein the post-print annealing comprises CO2 annealing.

4. The method of claim 1 further comprising post-print annealing the circuit effective for covalently binding biorecognition agents to the printed graphene for the purpose of electrochemical biosensing.

5. The method of claim 1 wherein the printable ink comprises graphene-nitrocellulose powder.

6. The method of claim 1 wherein the aerosol jet printing comprises:
    a. no contact with 1-5 mm variable standoff from the substrate;
    b. a tightly focused continuous stream of ink with 1-5 micron droplets of a viscosity between 1-1,000 cP;
    c. printer parameters to aerosol jet print thin and continuous graphene ink with minimal satellite droplets comprising:
        i. sheath flow rates of 40-60 sccm,
        ii. carrier flow rates of 15-45 sccm, and
        iii. printing speeds of approximately 5 mm/s were tuned to yield thin and continuous traces of graphene ink with minimal satellite droplets on the substrate.

7. The method of claim 1 wherein the substrate comprises:
    a. a rigid substrate; or
    b. a flexible substrate.

8. The method of claim 1 comprising scalable additive manufacturing.

9. The method of claim 8 wherein the scalable manufacturing comprises roll-to-roll additive manufacturing.

10. The method of claim 1 used for electrochemical sensing.

11. The method of claim 10 wherein the electrochemical sensing comprises biosensing.

12. The method of claim 1 used for at least one of:
    a. printable electronic devices;
    b. sensors;
    c. biosensors;
    d. point-of-care diagnostic devices;
    e. wearable devices;
    f. flexible electronics;
    g. MEMs biosensors;
    h. optoelectrical biosensors;
    i. thermistor biosensors;
    j. over the counter testing kits, or
    k. food safety monitoring.

13. The method of claim 1 used for an immunosensor, wherein the immunosensor comprises at least one of:
    a. monitors both IL-10 and IFN-gamma in an actual bovine sample;
    b. has a biomarkers sensing range of 0.1-10 ng/mL; and
    c. does not require a redox probe (e.g. metal nano particle) or fluorescent label for sensitive or visibility.

14. The method of claim 1 used for food safety monitoring.

15. The method of claim 1 in combination with a post-print annealing subsystem operated effective for one or more of:
    a. converting electrochemically inactive printed graphene into electrochemically active graphene, and
    b. covalently binding biorecognition agents to the printed graphene for the purpose of electrochemical biosensing.

16. The method of claim 1 wherein the cosolvent system comprises a 9:1 ethyl lactate:dibutyl phthalate cosolvent system.

17. The method of claim 1 wherein the printable ink has 30 mg/mL solids loading.

18. The method of claim 1 wherein the printable ink is filtered through a 3.1 µm filter.

19. A method of fabrication of graphene-based circuits on a substrate comprising:
    a. preparing a printable ink of pristine graphene flakes of graphene or graphene oxide exfoliated from graphite produced and dispersed in solvents from bulk synthesis solution processing;
    b. creating one or more patterns in one or more passes by scalable, high-throughput direct write additive manufacturing of the printable ink without stenciling or photolithography, and without pre- or post-patterning steps; and
    c. post-print annealing the one or more patterns in a $CO_2$ environment effective to convert electrochemically inactive printed graphene into electrochemically active graphene.

20. The method of claim 19, wherein the additive printing comprises aerosol jet printing or inkjet printing, and the printable ink comprises graphene-nitrocellulose powder.

21. The method of claim 19, wherein the additive printing is by aerosol jet printing comprising:
    a. no contact with 1-5 mm variable standoff from the substrate;
    b. a tightly focused continuous stream of ink with 1-5 micron droplets of a viscosity between 1-1,000 cP;
    c. printer parameters to aerosol jet print thin and continuous graphene ink with minimal satellite droplets comprising:
        i. sheath flow rates of 40-60 sccm,
        ii. carrier flow rates of 15-45 sccm, and iii. printing speeds of approximately 5 mm/s were tuned to yield thin and continuous traces of graphene ink with minimal satellite droplets on the substrate.

22. The method of claim 19 further comprising post-print annealing the circuit effective for covalently binding biorecognition agents to the printed graphene for the purpose of electrochemical biosensing.

23. The method of claim 19 in combination with a post-print annealing subsystem operated effective for one or more of:
   a. converting electrochemically inactive printed graphene into electrochemically active graphene, and
   b. covalently binding biorecognition agents to the printed graphene for the purpose of electrochemical biosensing.

24. A method of fabrication of graphene-based circuits on a substrate comprising:
   a. preparing a printable ink comprising graphene or graphene oxide exfoliated from graphite from a bulk synthesis process; and
   b. aerosol jet printing a circuit by direct additive manufacturing on a substrate using said printable ink without stenciling or photolithography for an immunosensor, wherein the immunosensor comprises at least one of:
      i. monitors both IL-10 and IFN-gamma in an actual bovine sample;
      ii. has a biomarkers sensing range of 0.1-10 ng/mL; and
      iii. does not require a redox probe (e.g. metal nano particle) or fluorescent label for sensitive or visibility.

25. The method of claim 24 further comprising post-print annealing the circuit effective to convert electrochemically inactive printed graphene into electrochemically active graphene.

26. The method of claim 25 wherein the post-print annealing comprises $CO_2$ annealing.

27. The method of claim 24 further comprising post-print annealing the circuit effective for covalently binding biorecognition agents to the printed graphene for the purpose of electrochemical biosensing.

28. The method of claim 24, wherein the printable ink comprises graphene-nitrocellulose powder.

29. The method of claim 24 wherein the aerosol jet printing comprises:
   a. no contact with 1-5 mm variable standoff from the substrate;
   b. a tightly focused continuous stream of ink with 1-5 micron droplets of a viscosity between 1-1,000 cP;
   c. printer parameters to aerosol jet print thin and continuous graphene ink with minimal satellite droplets comprising:
      i. sheath flow rates of 40-60 sccm,
      ii. carrier flow rates of 15-45 sccm, and
      iii. printing speeds of approximately 5 mm/s tuned to yield thin and continuous traces of graphene ink with minimal satellite droplets on the substrate.

30. The method of claim 24 wherein the substrate comprises:
   a. a rigid substrate; or
   b. a flexible substrate.

31. The method of claim 24 comprising scalable additive manufacturing.

32. The method of claim 24 used for food safety monitoring.

33. The method of claim 24 in combination with a post-print annealing subsystem operated effective for one or more of:
   a. converting electrochemically inactive printed graphene into electrochemically active graphene, and
   b. covalently binding biorecognition agents to the printed graphene for the purpose of electrochemical biosensing.

34. A method of fabrication of graphene-based circuits on a substrate comprising:
   a. preparing a printable ink comprising graphene or graphene oxide exfoliated from graphite from a bulk synthesis process; and
   b. aerosol jet printing a circuit by direct additive manufacturing on a substrate using said printable ink without stenciling or photolithography, wherein the aerosol jet printing comprises:
      i. no contact with 1-5 mm variable standoff from the substrate;
      ii. a tightly focused continuous stream of ink with 1-5 micron droplets of a viscosity between 1-1,000 cP;
      iii. printer parameters to aerosol jet print thin and continuous graphene ink with minimal satellite droplets comprising:
         sheath flow rates of 40-60 sccm,
         carrier flow rates of 15-45 sccm, and
         printing speeds of approximately 5 mm/s tuned to yield thin and continuous traces of graphene ink with minimal satellite droplets on the substrate.

35. The method of claim 34 further comprising post-print annealing the circuit effective to convert electrochemically inactive printed graphene into electrochemically active graphene.

36. The method of claim 35 wherein the post-print annealing comprises $CO_2$ annealing.

37. The method of claim 34 further comprising post-print annealing the circuit effective for covalently binding biorecognition agents to the printed graphene for the purpose of electrochemical biosensing.

38. A method of fabrication of graphene-based circuits on a substrate comprising:
   a. preparing a printable ink comprising graphene or graphene oxide exfoliated from graphite from a bulk synthesis process or otherwise fabricating a graphene-based circuit on a substrate using said printable ink; and
   b. creating the graphene-based circuits by additive printing of the printable ink by direct additive manufacturing without stenciling or photolithography, wherein the additive printing is by aerosol jet printing comprising:
      i. no contact with 1-5 mm variable standoff from the substrate;
      ii. a tightly focused continuous stream of ink with 1-5 micron droplets of a viscosity between 1-1,000 cP;
      iii. printer parameters to aerosol jet print thin and continuous graphene ink with minimal satellite droplets comprising:
         sheath flow rates of 40-60 sccm,
         carrier flow rates of 15-45 sccm, and
         printing speeds of approximately 5 mm/s tuned to yield thin and continuous traces of graphene ink with minimal satellite droplets on the substrate.

39. The method of claim 38 further comprising post-print annealing the circuit effective to convert electrochemically inactive printed graphene into electrochemically active graphene.

40. The method of claim 39 wherein the post-print annealing comprises $CO_2$ annealing.

41. The method of claim 38 further comprising post-print annealing the circuit effective for covalently binding biorecognition agents to the printed graphene for the purpose of electrochemical biosensing.

* * * * *